(12) United States Patent
Babich et al.

(10) Patent No.: US 8,211,401 B2
(45) Date of Patent: *Jul. 3, 2012

(54) TECHNETIUM- AND RHENIUM-BIS(HETEROARYL) COMPLEXES AND METHODS OF USE THEREOF FOR INHIBITING PSMA

(75) Inventors: John W. Babich, Cambridge, MA (US); Craig Zimmerman, Topsfield, MA (US); John Joyal, Melrose, MA (US); Kevin P. Maresca, Tewksbury, MA (US); Genliang Lu, Winchester, MA (US); Shawn Hillier, Danvers, MA (US)

(73) Assignee: Molecular Insight Pharmaceuticals, Inc., Cambridge, MA (US)

( * ) Notice: Subject to any disclaimer, the term of this patent is extended or adjusted under 35 U.S.C. 154(b) by 392 days.

This patent is subject to a terminal disclaimer.

(21) Appl. No.: 12/631,337

(22) Filed: Dec. 4, 2009

(65) Prior Publication Data
US 2010/0178246 A1 Jul. 15, 2010

Related U.S. Application Data

(60) Provisional application No. 61/120,226, filed on Dec. 5, 2008, provisional application No. 61/180,341, filed on May 21, 2009.

(51) Int. Cl.
| | | |
|---|---|---|
| A61K 51/04 | (2006.01) | |
| A61K 31/555 | (2006.01) | |
| A61K 49/00 | (2006.01) | |
| C07D 403/12 | (2006.01) | |
| C07D 401/12 | (2006.01) | |
| C07D 213/56 | (2006.01) | |
| C07F 13/00 | (2006.01) | |
| A61P 25/18 | (2006.01) | |
| A61P 29/00 | (2006.01) | |
| A61P 13/08 | (2006.01) | |
| A61P 35/00 | (2006.01) | |

(52) U.S. Cl. ........ 424/1.65; 424/9.1; 514/184; 514/188; 534/10; 534/14; 540/465; 546/12; 546/175; 546/265; 546/335; 548/104; 548/109; 548/314.4; 548/314.7

(58) Field of Classification Search .................. None
See application file for complete search history.

(56) References Cited

U.S. PATENT DOCUMENTS

| | | | |
|---|---|---|---|
| 2,730,456 A | 1/1956 | Green et al. | |
| 2,730,457 A | 1/1956 | Green et al. | |
| 2,800,457 A | 7/1957 | Green et al. | |
| 3,625,214 A | 12/1971 | Higuchi | |
| 4,272,398 A | 6/1981 | Jaffe | |
| 4,798,734 A | 1/1989 | Kaneda | |
| 4,906,474 A | 3/1990 | Langer et al. | |
| 4,925,673 A | 5/1990 | Steiner et al. | |
| 2003/0235843 A1 | 12/2003 | Babich et al. | |
| 2004/0191174 A1 | 9/2004 | Linder et al. | |
| 2004/0209921 A1 | 10/2004 | Bridger et al. | |
| 2005/0038258 A1 | 2/2005 | Koike et al. | |
| 2006/0057068 A1 | 3/2006 | Supuran et al. | |
| 2008/0227962 A1 | 9/2008 | Mazzanti | |
| 2009/0175794 A1 | 7/2009 | Zimmerman et al. | |
| 2010/0178247 A1 | 7/2010 | Babich et al. | |
| 2010/0183509 A1* | 7/2010 | Babich et al. | 424/1.65 |

FOREIGN PATENT DOCUMENTS

| | | |
|---|---|---|
| EP | 1 389 460 A1 | 2/2004 |
| EP | 1 550 657 A1 | 7/2005 |
| EP | 1 961 744 A1 | 8/2008 |
| JP | 04-342560 | 11/1992 |
| WO | WO-03/013617 A2 | 2/2003 |
| WO | WO-03/077727 A2 | 9/2003 |
| WO | WO-2004/014352 A2 | 2/2004 |
| WO | WO-2004/048544 A2 | 6/2004 |
| WO | WO-2005/056520 A1 | 6/2005 |
| WO | WO-2005/079865 | 9/2005 |
| WO | WO-2006/080993 A2 | 8/2006 |
| WO | WO-2007/090461 A1 | 8/2007 |
| WO | WO-2007/148738 A1 | 12/2007 |

(Continued)

OTHER PUBLICATIONS

Banerjee et al., caplus an 2008:872500.*
Alberto et al., "A Novel Organometallic Aqua Complex of Technetium for the Labeling of Biomolecules: Synthesis of [99Tc(OH2)3(CO3][99mTcO4]- in Aqueous Solution and Its Reaction with a Bifunctional Ligand", Journal of American Chemical Society, American Chemical Society, vol. 120, No. 31, 1998, pp. 7987-7988.
Banerjee et al., "{RE(III)CI3} Core Complexes with Bifunctional Single Amino Acid Chelates", Inorganic Chemistry, American Chemical Society, vol. 41, No. 22, 2002, pp. 5795-5802.

(Continued)

*Primary Examiner* — Sun Jae Loewe
(74) *Attorney, Agent, or Firm* — Gilberto M. Villacorta; Jeffrey R. Lomprey; Foley & Lardner, LLP

(57) ABSTRACT

A compound of Formula I, a pharmaceutically acceptable salt, or solvate thereof:

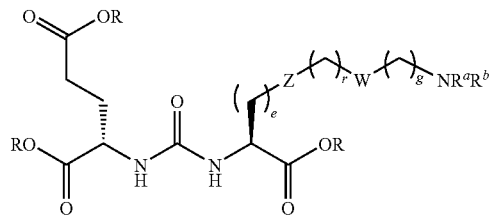

complexes with metals such as rhenium, technetium, and others to provide a complex for imaging tissues or treating disease, particularly where the metal is radioactive. Such complexes are specific to PSMA protein and can therefore be used in imaging or treating cancer of the prostate and other tissue where the protein is expressed.

20 Claims, 4 Drawing Sheets

FOREIGN PATENT DOCUMENTS

| | | |
|---|---|---|
| WO | WO-2008/028000 A2 | 3/2008 |
| WO | WO-2008/058192 A2 | 5/2008 |
| WO | WO-2009/076434 A1 | 6/2009 |
| WO | WO-2009/089383 A2 | 7/2009 |
| WO | WO2010065899 | * 12/2009 |
| WO | WO-2010/036814 A1 | 4/2010 |
| WO | WO-2010/065906 A2 | 6/2010 |

OTHER PUBLICATIONS

Banerjee et al., Bifunctional Single Amino Acid Chelates for Labeling of Biomolecules with the {Tc(CO)3} and {Re(CO)3} Cores. Crystal and Molecular Structures of [ReBr(CO)3(H2NCH2C5H4N)], [Re(Co)3{C5H4NCH2)2NH}Br, [Re(CO)3{C5H4NCH2)2NCH2CO2H}Br, [Re(CO)3{X(Y)NCH2CO2CH2CH3}Br(X=Y=2-pyridylmethyl; X=2-pyridylmethyl, Y=2-(1-methylimidazolyl)methyl, [ReBr(CO)3{C5H4NCH2)NH(CH2C4H3S)}], and [Re(CO)3{C5H4NCH2)N(CH2C4H3S)(CH2CO2)}], Inorganic Chemistry, vol. 41, No. 24, 2002, pp. 6417-6425.

Banerjee et al., "Synthesis and Evaluation of Technetium-99m- and Rhenium-Labeled Inhibitors of the Prostate-Specific Membrane Antigen (PSMA)", Journal of Medicinal Chemistry, vol. 15, pp. 4504-4517, 2008.

Benita, S. et al., "Characterization of Drug-Loaded Poly(d,l-lactide) Microspheres," Journal of Pharmaceutical Sciences, vol. 73, No. 12, Dec. 1984, pp. 1721-1724.

Berge et al., "Pharmaceuticals Salts," J. Pharm. Sci, vol. 66, No. 1, pp. 1-19., 1977.

Bonomi et al., Renato, "Phosphate Diester and DNA Hydrolysis by a Multivalent, Nanoparticle-Based Catalyst", Journal of the American Chemical Society, vol. 130, 2008, pp. 15744-15745.

Casini, Angela et al., "Carbonic Anhydrase Inhibitors: Synthesis of Water Soluble Sulfonamides Incorporating a 4-sulfamoylphenylmethylthiourea Scaffold, with Potent Intraocular Pressure Lowering Properties," Journal of Enzyme Inhibition and Medicinal Chemistry, 2002, vol. 17, No. 5, pp. 333-343.

Cecchi et al., Alessandro, "Carbonic Anhydrase Inhibitors. Design of Fluorescent Sulfonamides as Probes of Tumor-assoicated Carbonic Anhydrase IX that Inhibit Isozyme IX-Mediated Acidification of Hypoxic Tumores," Journal of Medicinal Cheimistry, vol. 48, No. 15, Jul. 2005, pp. 4834-4841.

Database Beilstein [Online]; Beilstein Institute for Organic Chemistry, 1958, Database Accession No. Citation No. 990210, XP002577062.

Deasy, Patrick et al., Microencapsulation and Related Drug Processes, 1984, School of Pharmacy, University of Dublin, Marcel Dekker, Inc.

Feng et al., Guoqiang, "Comparing a mononuclear Zn(II)complex with hydrogen bond donors with a dinuclear Zn(II) complex for catalysing phosphate ester cleavage", The Royal Society of Chemistry, 2006, pp. 1845-1847.

Greene, T. W. et al., Protective Groups in Organic Synthesis, Second Edition, Wiley, New York, 1991.

Greene, T. W. et al., Protective Groups in Organic Synthesis, Third Edition, Wiley, New York, 1999.

Gregoriadis, G., et al., Drug Carriers in Biology and Medicine, Chapter 14: Liposomes, pp. 287-341.

Henson et al., Mark J., "Resonance Raman Investigation of Equatorial Ligand Donor Effects on the Cu2O22 Core in End-On and Side-On u-Perozo-Dicopper(II) and Bis-u-oxo-Dicopper(III) Complexes", Journal of American Chemical Society, vol. 125, 2003, pp. 5186-5192.

International Search Report and Written Opinion mailed Jun. 26, 2009 in International Application No. PCT/US2009/030487.

International Search Report and Written Opinion mailed Oct. 14, 2010 in International Application No. PCT/US2009/066832.

International Search Report and Written Opinion mailed Dec. 28, 2010 in International Application No. PCT/US2009/066836.

Invitation to Pay Additional Fees mailed May 17, 2010 in International Application No. PCT/US2009/066832.

Invitation to Pay Additional Fees mailed May 17, 2010 in International Application No. PCT/US2009/066836.

Invitation to Pay Additional Fees mailed May 17, 2010 in International Application No. PCT/US2009/066842.

Jalil, R. et al., "Biodegradable poly(lactic acid) and poly(lactide-co-glycolide) microcapsules: problems associated with preparative techniques and release properties", J. Microencapsulation, 1990, vol. 7, No. 3, pp. 297-325.

Kojima et al., "Synthesis and Characterization of Mononuclear Ruthenium (III) Pyridylamine Complexes and Mechanistic Insights into Their Catalytic Alkane Functionalization with m-Chloroperbenzoic Acid", Chemistry, vol. 13, 2007, pp. 8212-8222.

Krebs, H.A., "Inhibition of Carbonic Anhydrase by Sulphonamides," The Biochemical Journal, vol. 43, 1948, pp. 525-528.

Kularatne, S.A. et al., "Design, Synthesis, and Preclinical Evaluation of Prostate-Specific Membrane Antigen Targeted 99mTc-Radioimaging Agents," Molecular Pharmaceutics, vol. 6, No. 3, pp. 790-800.

Lewis et al., "Maleimidocysteineamido-DOTA Derivatives: New Reagents for Radiometal Chelate Conjugation to Antibody Sulfhydryl Groups Undergo pH-Dependent Cleavage Reactions", Bioconjugate Chemistry, American Chemical Society, vol. 9, No. 1, 1998, pp. 72-86.

Lim, Franklin et al, "Microencapsulation of Living Cells and Tissues," Journal of Pharmaceutical Sciences, Apr. 1981, vol. 70, No. 4, pp. 351-354.

Mathiowitz, E. et al., "Mophology of Polyanhydride Miscrosphere Delivery Systems," Scanning Microscopy, 1990, vol. 4, No. 2, pp. 329-340.

Mathiowitz, E. et al., "Polyanhydride Microspheres as Drug Carriers. II. Microencapsulation by Solvent Removal," Journal of Applied Polymer Science, 1988, vol. 35, pp. 755-774.

Nakano, M. et al., "Sustained Urinary Excretion of Sulfamethizole Following Oral Administration of Enteric Coated Microcapsules in Humans," International Journal of Pharmaceutics, 1980, vol. 4, pp. 291-298.

Nonat et al., Aline, "Structure, Stability, Dynamics, High-Field Relaxivity and Ternary-Complex Formation of a New Tris(aquo) Gadolinium Complex", Chemistry, vol. 13, 2007, pp. 8489-8506.

Roy et al, Bidham C., "Two-Prong Inhibitors for Human Carbonic Anhydrase II", Journal of American Chemical Society, vol. 126, 2004, pp. 13206-13207.

Salib, N. et al., "Utilization of Sodium Alginate in Drug Microencapsulation," Pharm. Ind., vol. 40, No. 11a, 1978, pp. 1230-1234.

Sawhney, A. et al., "Bioerodible Hydrogels Based on Photopolymerized Poly(ethylene glycol)-co-poly(a-hydroxy acid) Diacrylate Macromers," Macromolucules, vol. 26, 1993, pp. 581-587.

Thallaj, Nasser K., "A Ferrous Center as Reaction Site for Hydration of a Nitrile Group into a Carboxamide in Mild Conditions", Journal of American Chemical Society, vol. 130, 2007, pp. 2414-2415.

Thiry et al., "Targeting Tumor-Associated Carbonic Anhydrase IX in Cancer Therapy," Trends in Pharmacological Sciences, vol. 27, No. 11, Nov. 2006, pp. 566-573.

Yao, Zhen et al., Synthesis of Porphyrins Bearing 1-4 hydroxymethyl Groups and other One-carbon oxygenic Substituents in Distinct Patterns, Tetrahedron, vol. 63, 2007, pp. 10657-10670.

Dubois, L., et al., "Imaging the hypoxia surrogate marker CA IX requires expression and catalytic activity for binding fluorescent sulfonamide inhibitors," 2007, Radiotherapy and Oncology, vol. 83, pp. 367-373.

Pastorekov, S., et al., "Carbonic anhydrase IX (CA IX) as potential target for cancer therapy," 2004, Cancer Therapy, vol. 2. (19 pages).

Restriction Requirement received for U.S. Appl. No. 12/350,894 dated Jun. 10, 2011.

EPA, Commonly Encountered Radionuclides, 2011, http://www.epa.gov/radiation/radionuclides/ (2 pgs.).

Steffens MG, et al., "Targeting of Renal Cell Carcinoma with Iodine-131-Labeled Chimeric Monoclonal Antibody G250," J. Clin. Oncol., 15(4), 1997, pp. 1529-1537. (abstract).

Office Action mailed Sep. 8, 2011 in U.S. Appl. No. 12/350,894.

Hanada et al., "Preparation of 2,8-diazaspiro[4.5]decane containing bis(imidazol-2-ylmethyl_amines as CXCR4 antagonists for treatment of inflammation and immune disease", caplus an 2008:159048, 5 pages.

Kusumi et al., "Preparation of heterocycle compounds having (un)protected acidic group as CXCR4 antagonists", caplus an 2007:1332283, 8 pages.

Saitou et al., "Preparation of N-arylmethyl or N-hererocyclylmethyl-N-(imidazol-2-ymethyl)amines as antagonists of chemokine receptor CXCR4", caplus an 2005:1004718, 6 pages.

Notice of Allowance received for U.S. Appl. No. 12/631,343 dated Mar. 12, 2012.

Non-final Office Action received for U.S. Appl. No. 12/631,312 dated Mar. 6, 2012.

* cited by examiner

TECHNETIUM- AND RHENIUM-BIS(HETEROARYL) COMPLEXES AND METHODS OF USE THEREOF FOR INHIBITING PSMA

CROSS-REFERENCE TO RELATED PATENT APPLICATIONS

This application claims the benefit of U.S. Provisional Patent Applications 61/120,226 filed on Dec. 5, 2008, and 61/180,341, filed on May 21, 2009, both of which are incorporated herein by reference in their entirety, for any and all purposes.

BACKGROUND OF THE INVENTION

The present invention relates generally to the field of radiopharmaceuticals and their use in nuclear medicine as tracers, imaging agents and for the treatment of various disease states. It is well known that tumors may express unique proteins associated with their malignant phenotype or may over-express normal constituent proteins in greater number than normal cells. The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins provide an attractive route for imaging and treating tumors under non-invasive conditions. In particular, the present inventors have found that radiolabeled ligands to the PSMA protein, often over expressed on many cancer cells provide an attractive route for non-invasive imaging and selective targeting of cancer cells.

At least 1 million men suffer from prostate cancer and it's estimated that the disease will strike one in six U.S. men between the ages of 60 and 80. There are more than 300,000 new cases of prostate cancer diagnosed each year. Prostate cancer will affect one in six men in the United States, and the mortality from the disease is second only to lung cancer. An estimated $2 billion is currently spent worldwide on surgical, radiation, drug therapy and minimally invasive treatments, $1 billion of the spending in the U.S. There is presently no effective therapy for relapsing, metastatic, androgen-independent prostate cancer. New agents that will enable rapid visualization of prostate cancer and specific targeting to allow radiotherapy present are needed.

N-acetylated alpha-linked acidic dipeptidase (NAALADase), also known as glutamate carboxypeptidase II (GCPII) is a neuropeptidase which cleaves N-acetylaspartylglutamate (NAAG) into N-acetylaspartate and glutamate in the nervous system, see below, depicting hydrolytic cleavage of NAAG by NAALDase through the tetrahedral intermediate. The enzyme is a type II protein of the co-catalytic class of metallopeptidases, containing two zinc atoms in the active site.

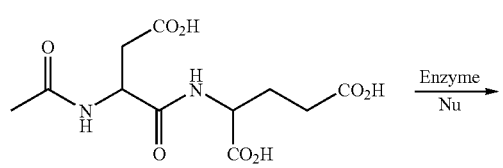

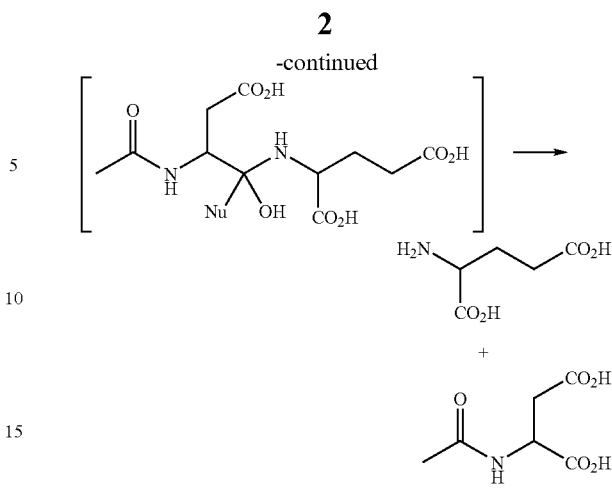

Independent of its characterization in the nervous system, one form of NAALADase was shown to be expressed at high levels in human prostatic adenocarcinomas and was designated the prostate-specific membrane antigen (PSMA). The NAALADase/PSMA gene is known to produce multiple mRNA splice forms and based on previous immunohistochemical evidence, it has been assumed that the human brain and prostate expressed different isoforms of the enzyme.

Human prostate-specific membrane antigen (PSMA), also known as folate hydrolase I (FOLH1), is a trans-membrane, 750 amino acid type II glycoprotein which is primarily expressed in normal human prostate epithelium but is upregulated in prostate cancer, including metastatic disease. PSMA is a unique exopeptidase with reactivity toward poly-gamma-glutamated folates, capable of sequentially removing the poly-gamma-glutamyl termini. Since PSMA is expressed by virtually all prostate cancers and its expression is further increased in poorly differentiated, metastatic and hormone-refractory carcinomas, it is a very attractive target for prostate imaging and therapy. Developing ligands that interact with PSMA and carry appropriate radionuclides may provide a promising and novel targeting option for the detection, treatment and management of prostate cancer.

The radio-immunoconjugate form of the anti-PSMA monoclonal antibody (mAb) 7E11, known as the PROSTASCINT scan, is currently being used to diagnose prostate cancer metastasis and recurrence. More recently, monoclonal antibodies have been developed that bind to the extracellular domain of PSMA and have been radiolabeled and shown to accumulate in PSMA-positive prostate tumor models in animals.

While monoclonal antibodies hold promise for tumor detection and therapy, there have been limited clinical successes outside of lymphoma because of their low permeability in solid tumors. Low molecular weight mimetics, with higher permeability in solid tumors will have a definite advantage in obtaining high percent per gram and a high percentage of specific binding.

The selective targeting of cancer cells with radiopharmaceuticals, either for imaging or therapeutic purposes is challenging. A variety of radionuclides are known to be useful for radio-imaging, including Ga-67, Tc-99m, In-111, I-123, and I-131. The preferred radioisotope for medical imaging is Tc-99m, because it has a short (6 hour) half life, is readily available at relatively low cost and emits gamma-photons of 140 keV. Moreover, Tc-99m complexes, such as, water and

SUMMARY OF THE INVENTION

In one aspect, a compound of Formula I or a pharmaceutically acceptable salt, or solvate thereof is provided:

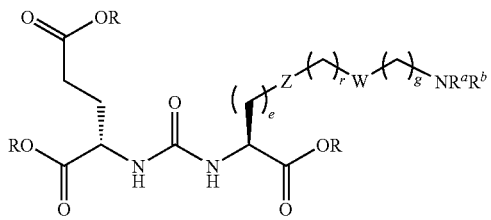

I where: R is H, an ammonium ion, an alkylammonium ion, an alkaline earth metal ion, a rare earth metal ion, or an alkyl group; W is a bond, —NHC(O)—, —CH(NH$_2$)—, —NH—C(O)—NH—, —C(O)—NH—, —C(O)—NH—CH(COOH)—, —O—(CH$_2$)$_n$—O—(CH$_2$)$_n$—, —(CH$_2$)$_n$O(CH$_2$)$_n$O(CH$_2$)$_n$—, —CH(NHFmoc)-; Z is a bond, —CO(O)—, —NH—, —NHC(O)—, —NH—C(O)—NH—, —NH—C(O)—(CH$_2$)$_n$—, —NH—C(O)—CH(NH$_2$)—, —C(O)—NH—CH(COOH)—; or —NH—C(O)—C$_6$H$_4$—(CH$_2$)$_n$—NH—; NR$^a$R$^b$ is a chelator group of Formula:

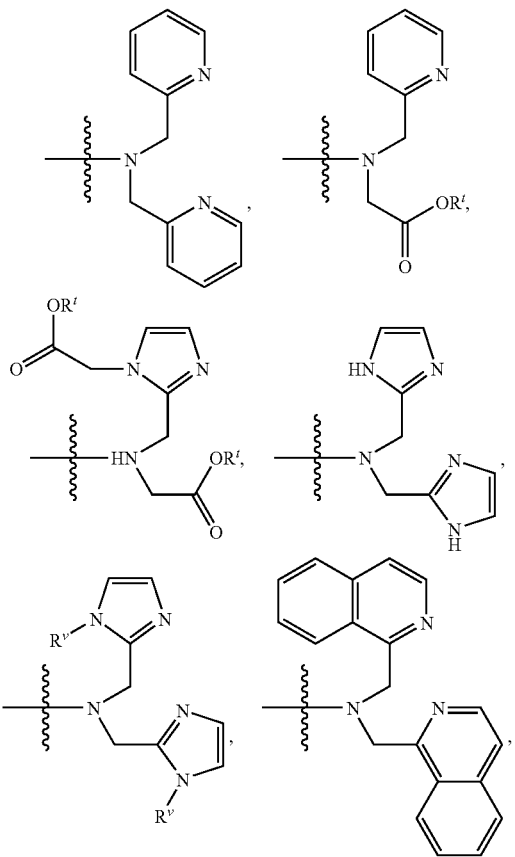

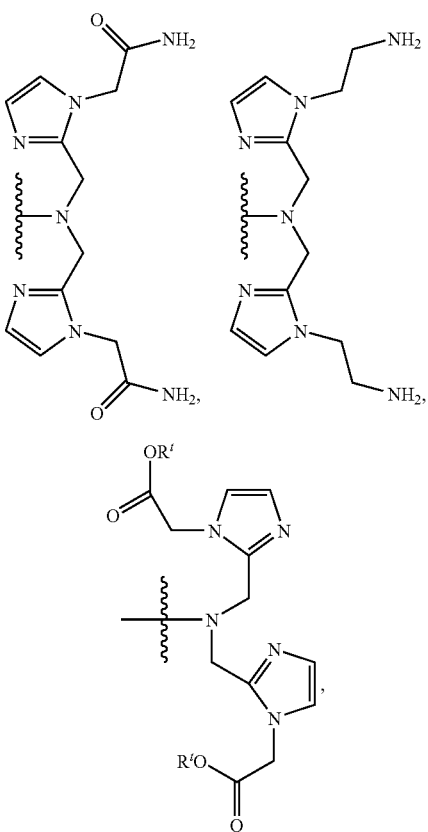

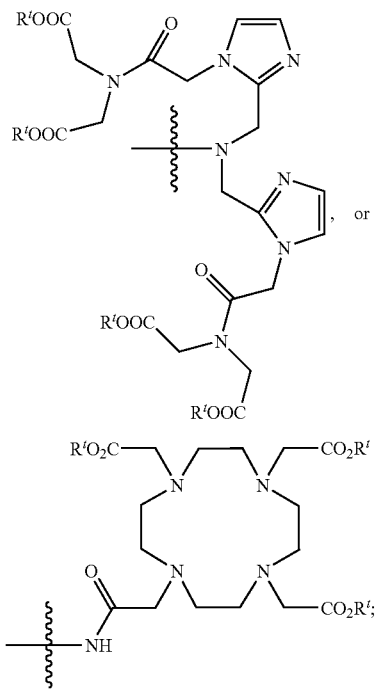

R$^t$ is H, a C$_1$-C$_8$ alkyl group, an ammonium ion, an alkylammonium ion, or an alkali or alkaline earth metal ion; R$^v$ is alkyl alkyl, substituted aminoalkyl, aminoalkyl, or, acetamidoalkyl; e is an integer from 0 to 15; f is an integer from 0 to 15; g is an integer from 0 to 15; and n is an integer from 0 to 10; with the proviso that where NR$^a$R$^b$ is:

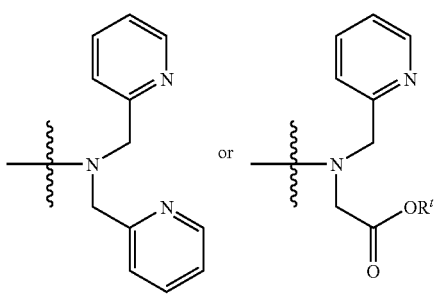

then where W is a bond, Z are other than a bond, —C(O)—NH—, or —NHC(O)—; and where Z is a bond, W is other than a bond, —C(O)—NH—, or —NHC(O)—.

In some embodiments, $R^v$ is methyl, ethyl, n-propyl, isopropyl, n-butyl, iso-butyl, tert-butyl, aminoalkyl, hydroxyalkyl, or carboxyalkyl. In some embodiments, $R^v$ is methyl. In some embodiments, each $R^t$ is independently H or tert-butyl. In some embodiments, $R^t$ is H. In some embodiments, e is an integer from 0 to 4, f is an integer from 0 to 10, and g is an integer from 0 to 6. In some embodiments, W is —C(O)—NH—.

In some embodiments, the compound of Formula I is:

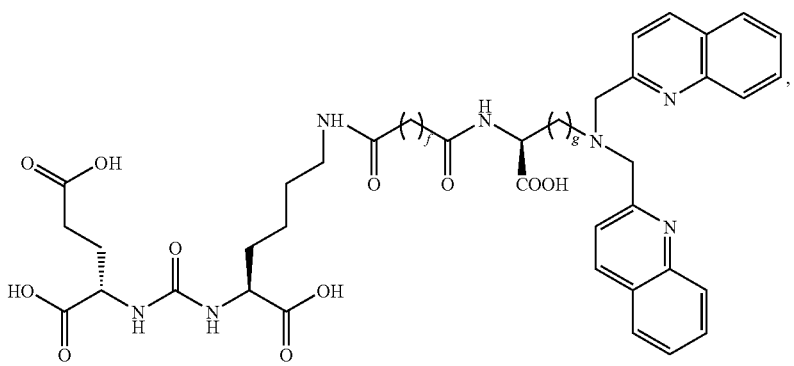

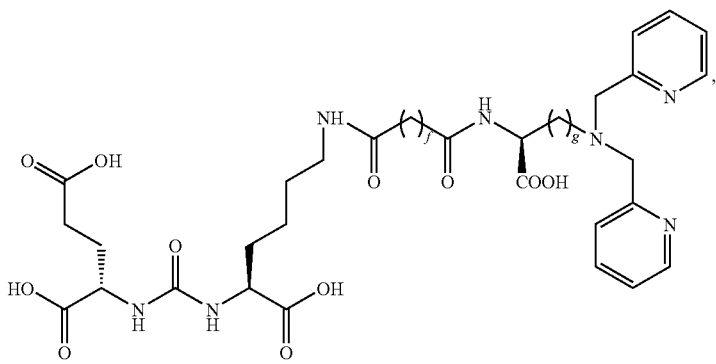

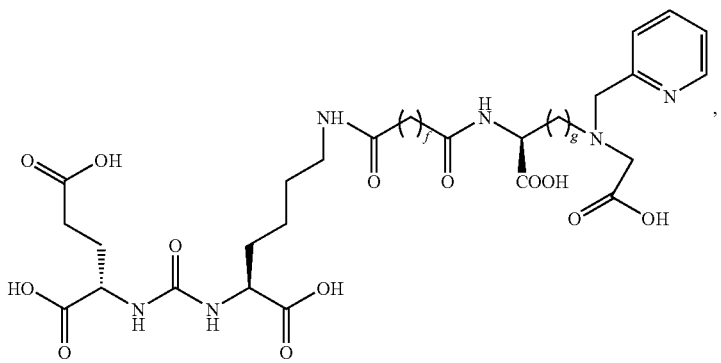

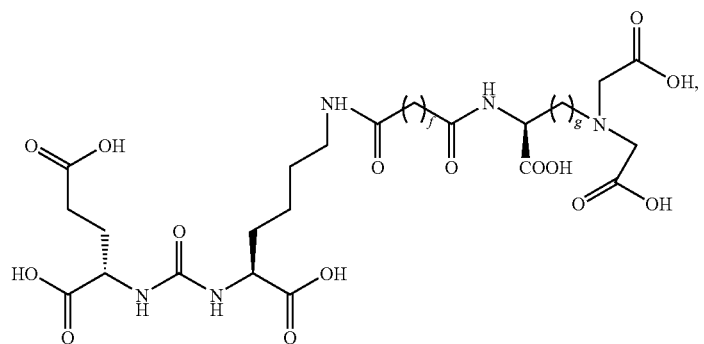
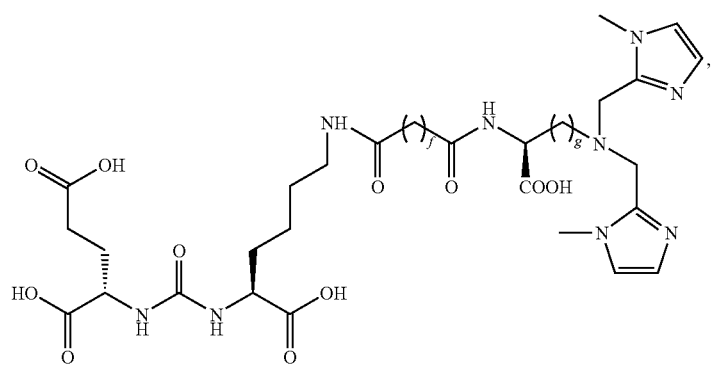
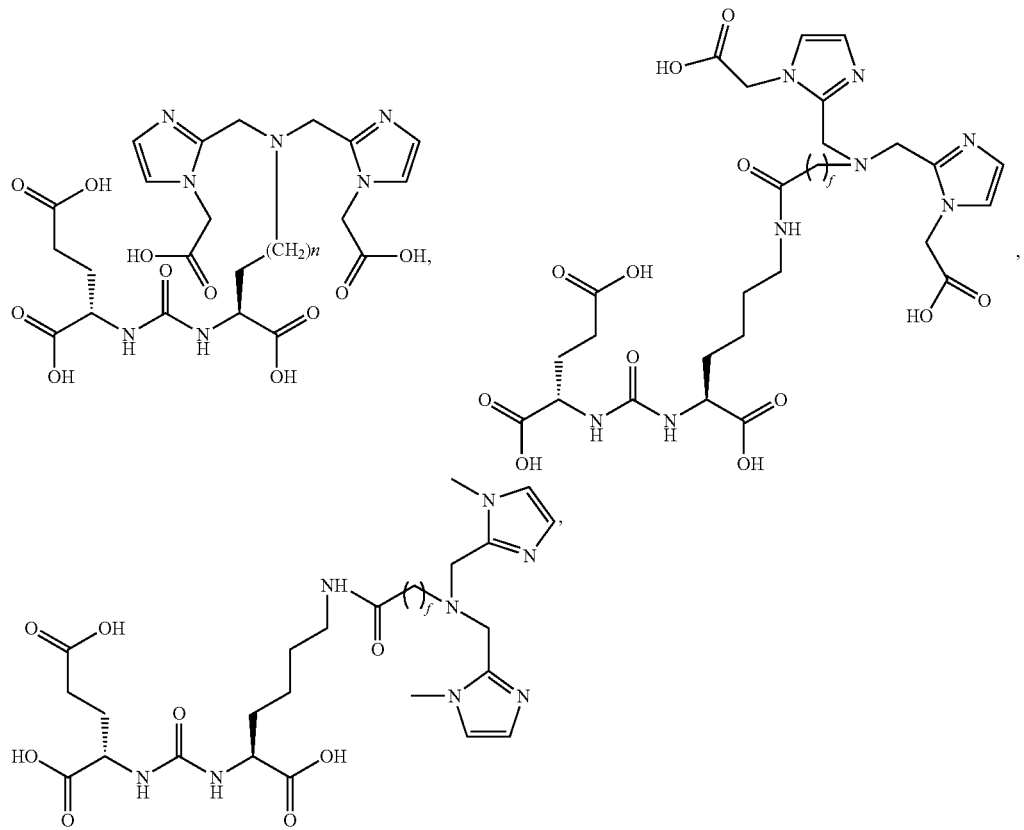

-continued
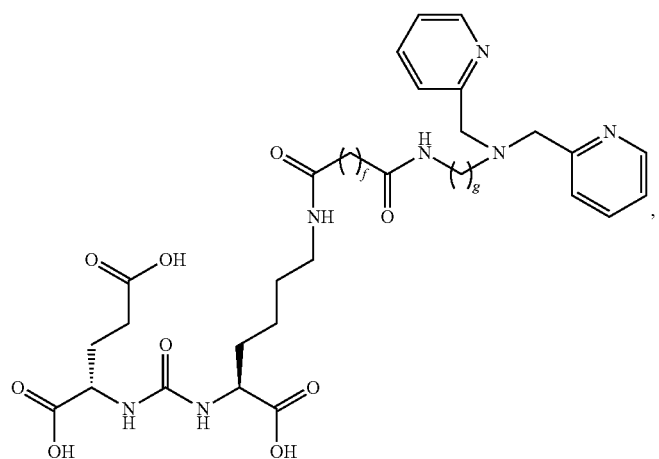
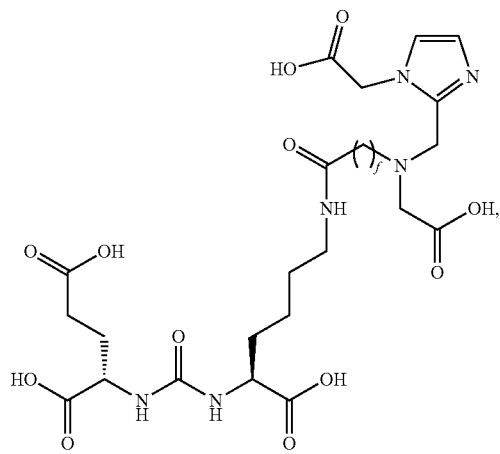
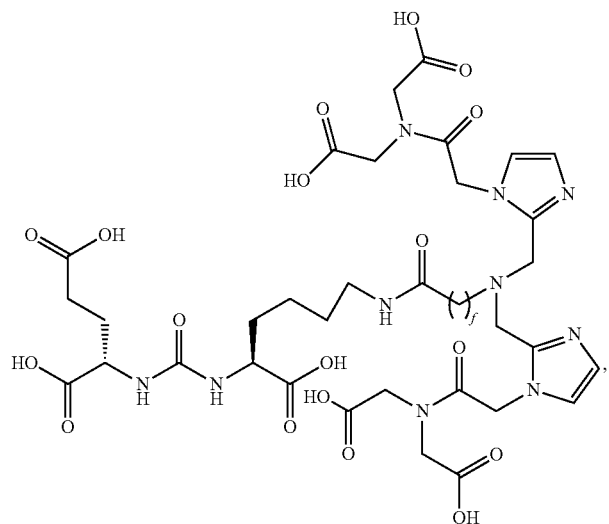
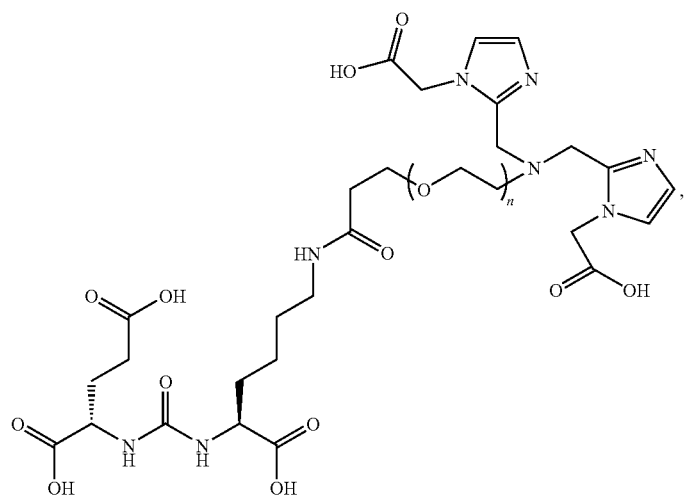

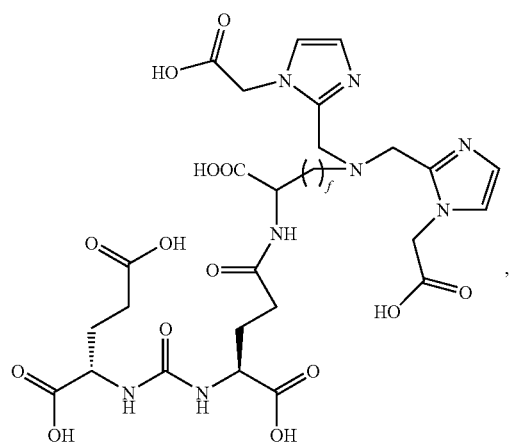
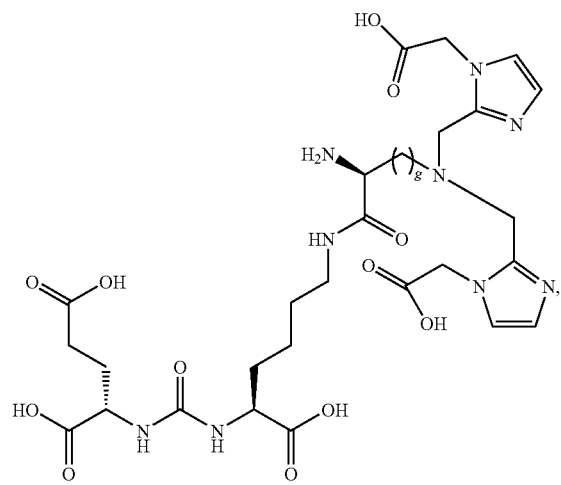
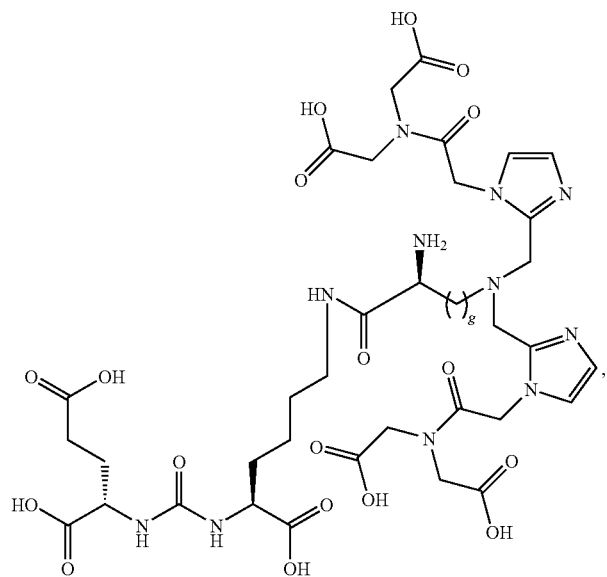
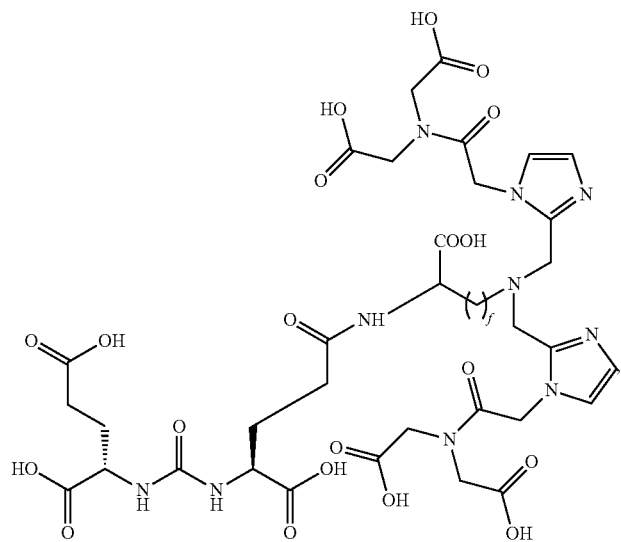

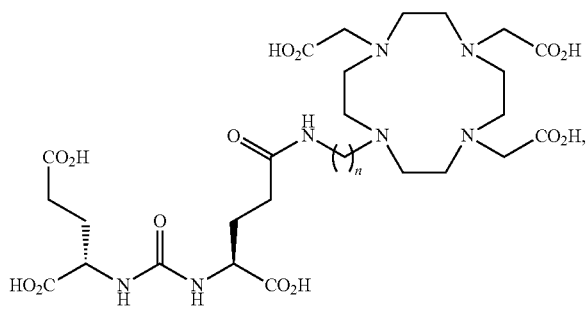

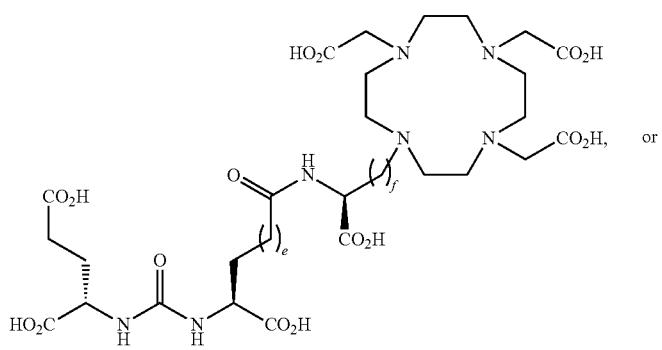

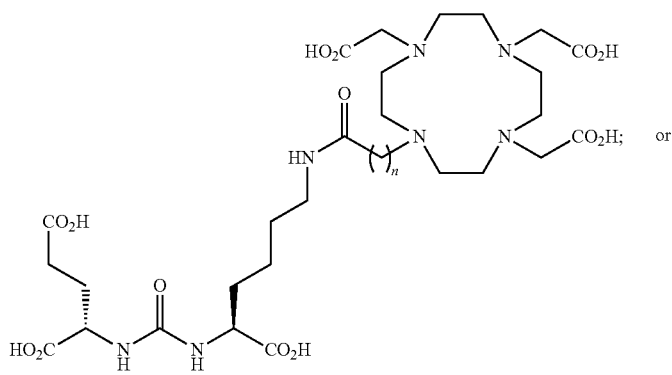

a pharmaceutically acceptable salt, or solvate thereof; e is an integer from 0 to 10; f is an integer from 0 to 10; g is an integer from 0 to 10; and n is an integer from 0 to 10.

In some embodiments, Z is —NH—C(O)—. In some embodiments, Z is —C(O)—NH—CH(COOH)—. In some embodiments, Z is —NH—C(O)—CH($NH_2$)—.

In another aspect a complex is provided including a metal a metal and a compound of Formula I. In some embodiments, the metal is Re, Tc, Y, Lu, Ga, In, or Cu. In some embodiments, the metal is a radionuclide. In some embodiments, the metal is technetium-99m, rhenium-186, or rhenium-188.

In some embodiments, the metal in the complex is Y, Lu, Ga, In, or Cu where the complex includes $NR^aR^b$ as being a group of formula

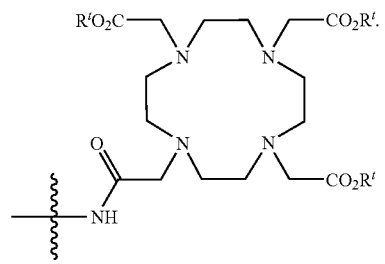

In some embodiments, the complex is:
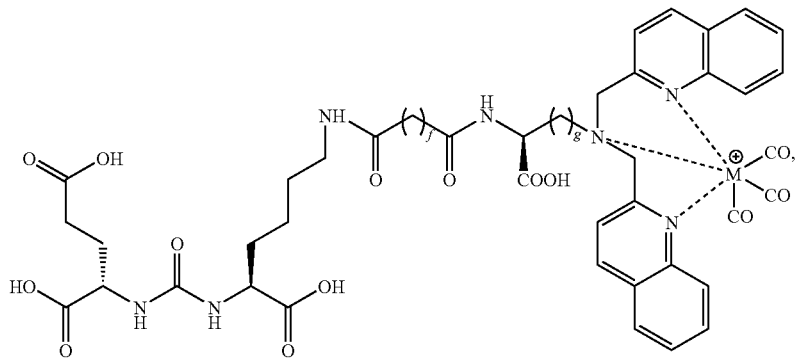
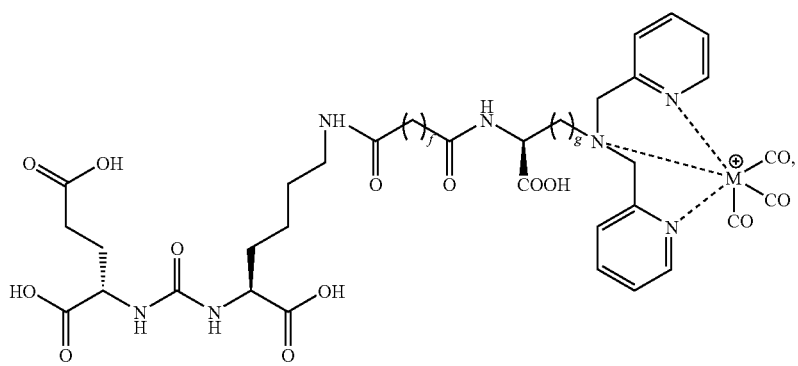
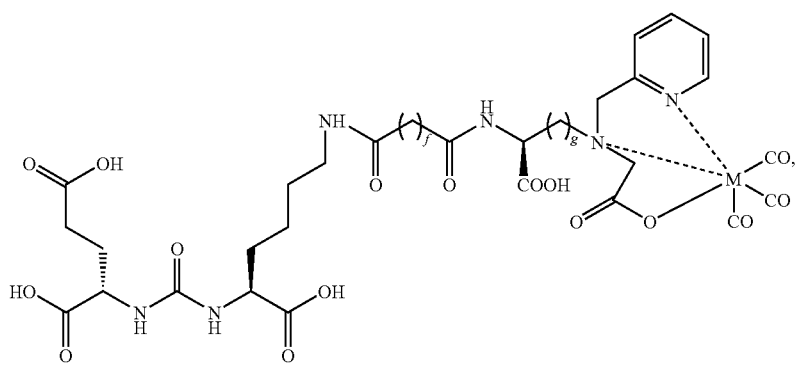
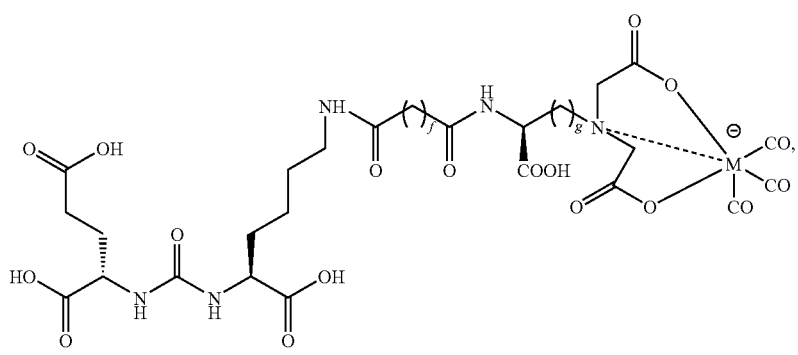

-continued
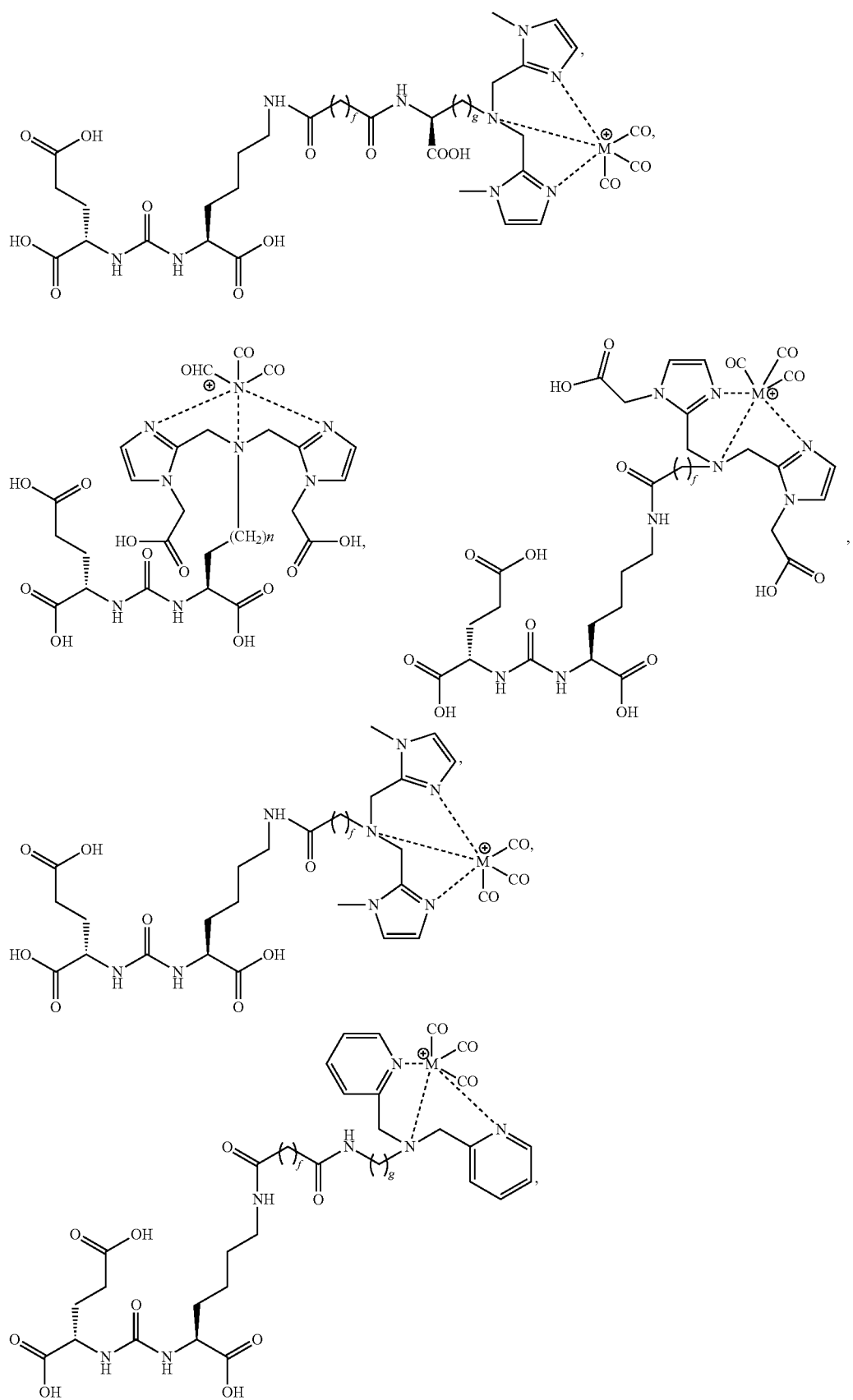

-continued
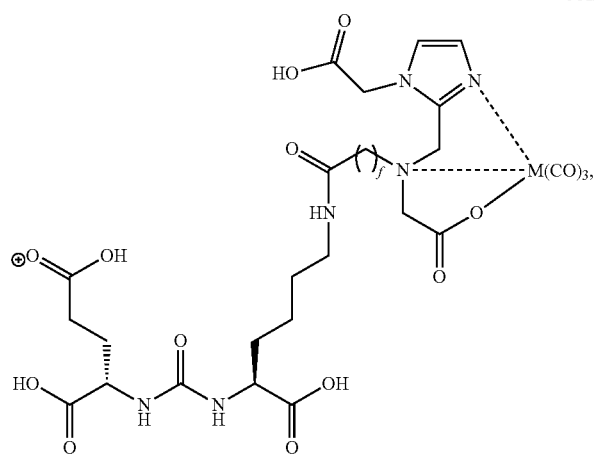
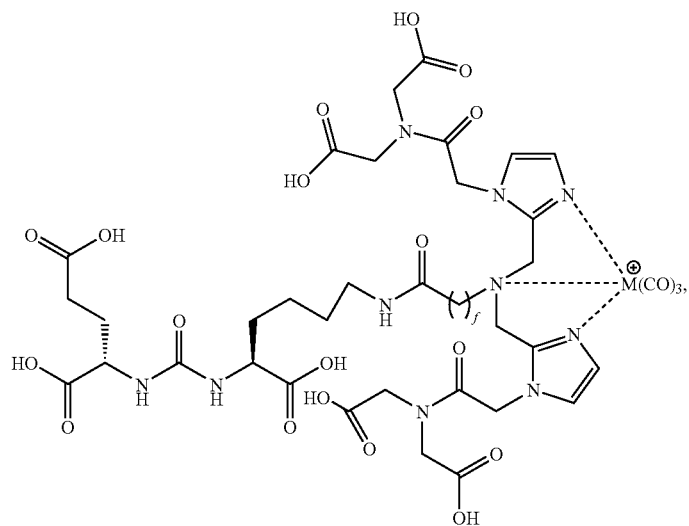
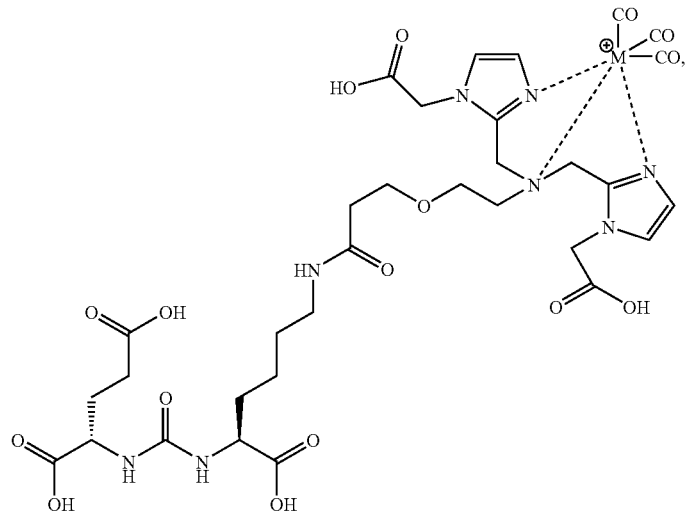

21
22
-continued
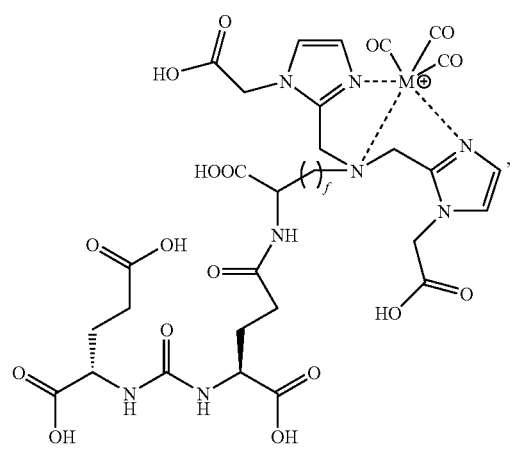
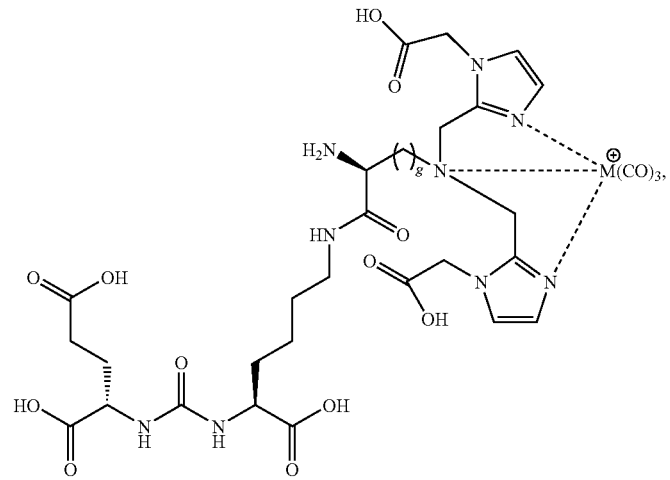
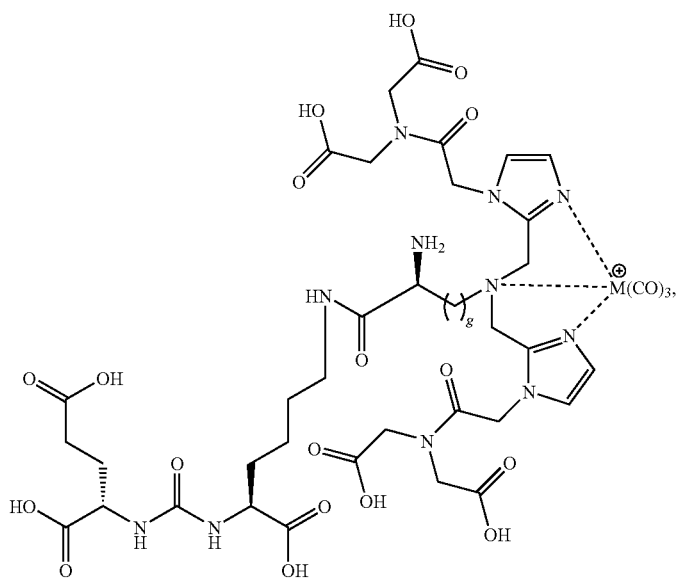
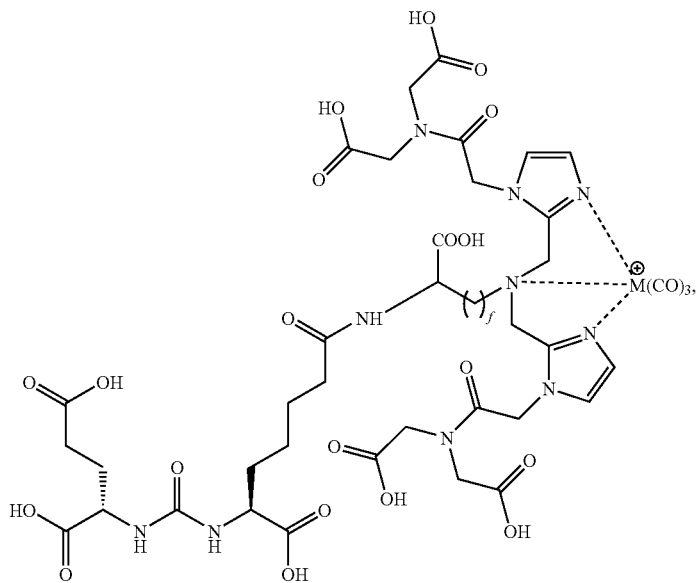

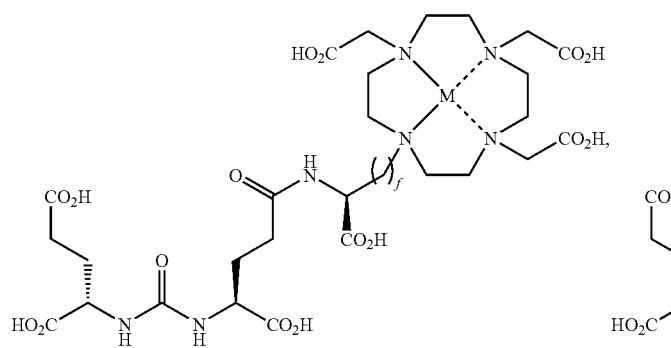
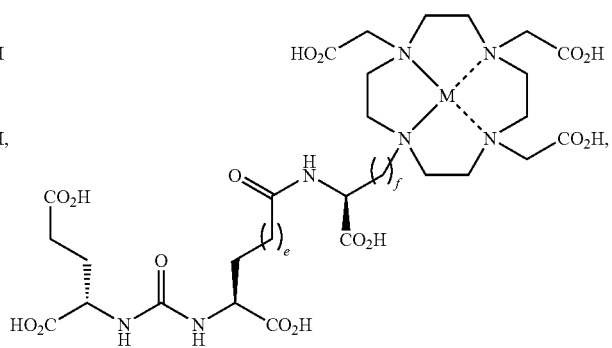

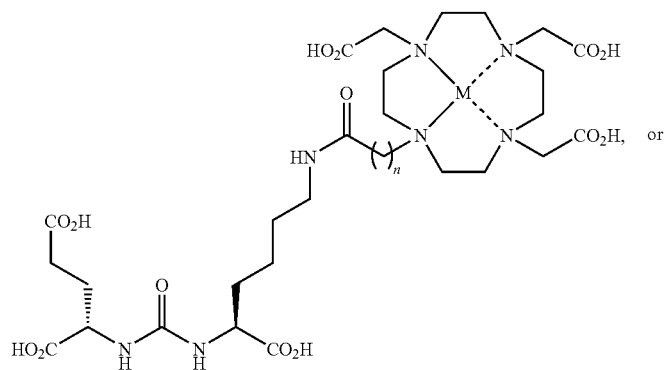

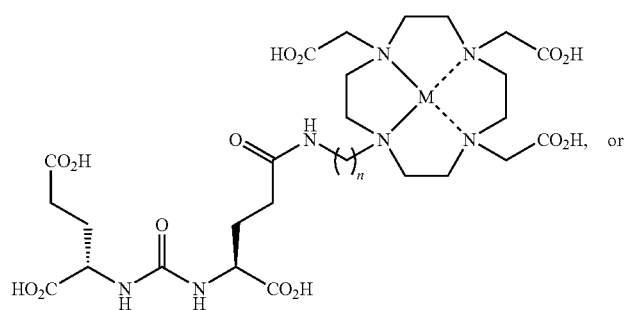

a pharmaceutically acceptable salts and solvates thereof; Re, Tc, Y, Lu, Ga, Cu; e is an integer from 0 to 10; f is an integer from 0 to 10; g is an integer from 0 to 10; and n is an integer from 0 to 10.

In another aspect, a pharmaceutical formulation is provided including the compound of Formula I, a pharmaceutically acceptable salt or solvate thereof, and a pharmaceutically acceptable excipient.

In another aspect, a method of imaging a region in a patient is provided including administering to a patient a diagnostically effective amount of a compound of Formula I, a pharmaceutically acceptable salt or solvate thereof, and obtaining an image of the region of the patient.

In another aspect, a method of imaging tissue such as spleen tissue, kidney tissue, or PSMA-expressing tumor tissue is provided including contacting the tissue with a complex including a radioactive metal and a compound including a group of formula:

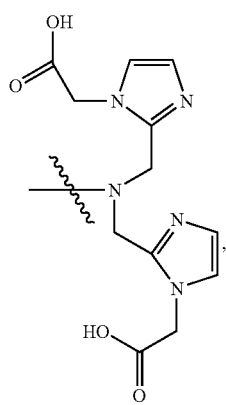

-continued

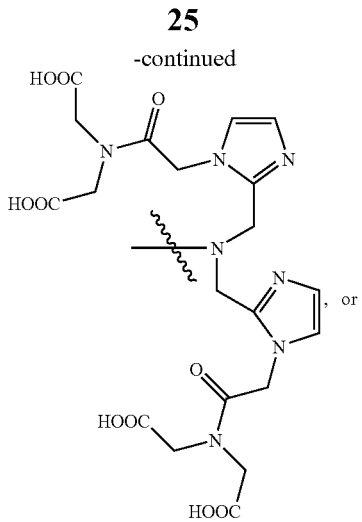

a pharmaceutically acceptable salt or solvate thereof. In some embodiments, the tissue is PSMA-expressing tumor tissue. In other embodiments, the PSMA-expressing tumor tissue is prostate cancer.

DETAILED DESCRIPTION OF THE PREFERRED EMBODIMENTS

Figure 1:
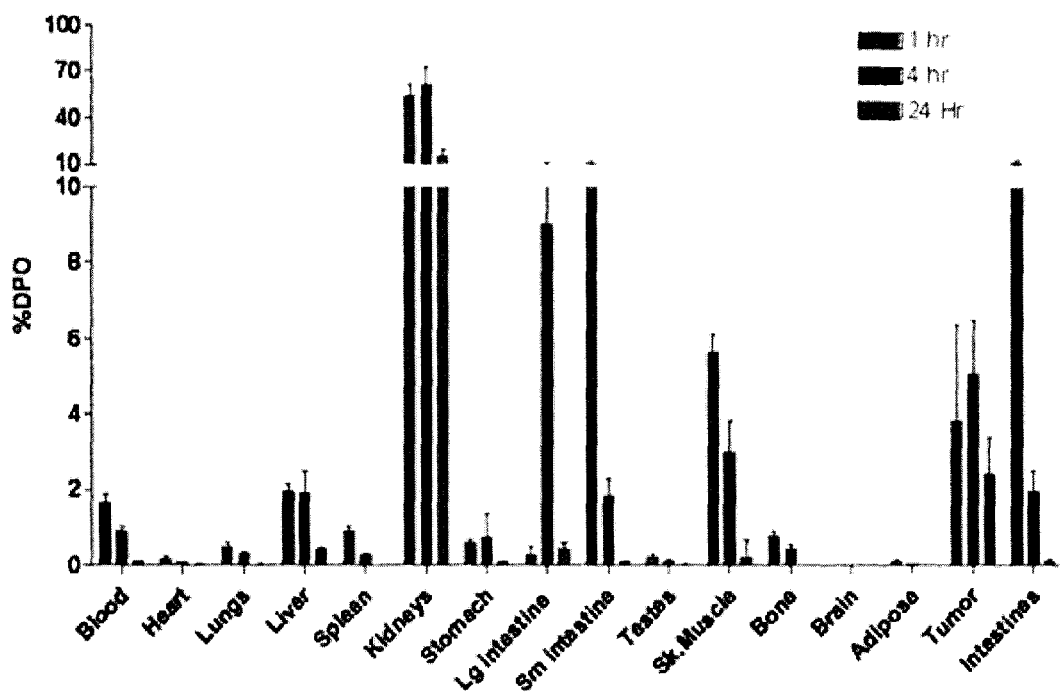
FIG. 1 is a graph of tissue distribution for a $^{99m}$Tc complex of the compound of Example 3 in LNCaP Xenograft mice in % DPO.
Figure 2:
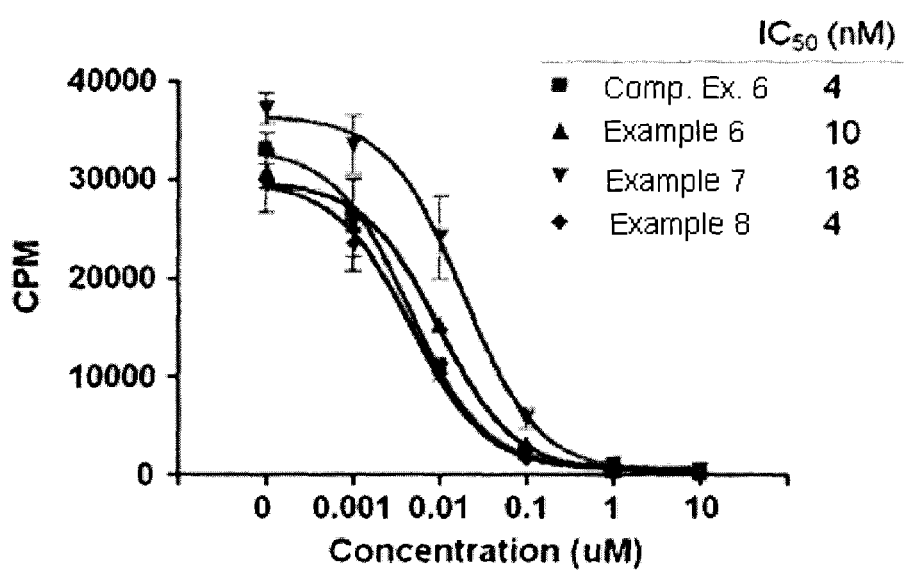
FIG. 2 shows competition binding curves for comparative and illustrative compounds according to Formula I for PSMA protein.
Figure 3:
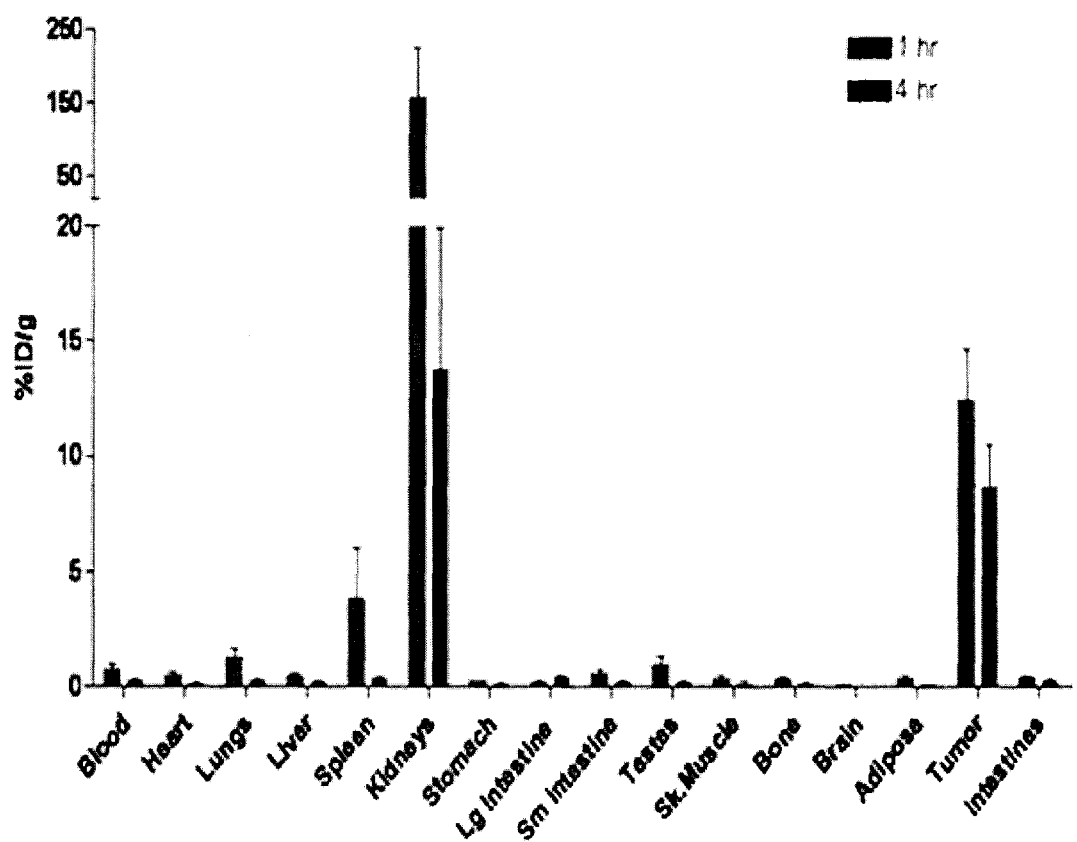
FIG. 3 is a graph of the tissue biodistribution of a $^{99m}$Tc complex of the compound of Example 8, expressed as % ID/g.
Figure 4:
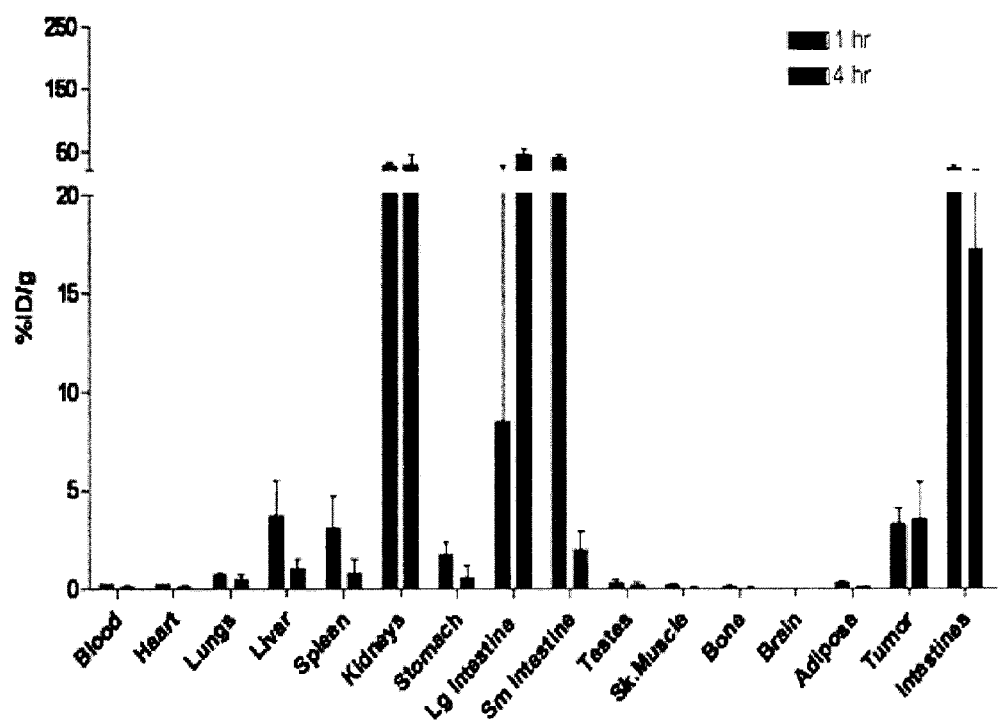
FIG. 4 is a graph of the tissue biodistribution of a $^{99m}$Tc complex of the compound of Example 7, expressed as % ID/g.

The are two categories of radiopharmaceuticals: (i) those with biological distribution determined strictly by blood flow, or perfusion, and targeting high capacity systems such as glomerular filtration, phagocytosis, hepatocyte clearance and bone absorption and (ii) those with distribution determined by specific enzymatic or receptor binding interactions, which are low-capacity sites. The inventive radiopharmaceuticals belong to the second category and are synthesized by conjugating the radionuclide coordination complex to a biologically active molecule selective for a particular protein or receptor of interest.

While a variety of biologically active molecules (BAM) can be used as the carriers, small molecules and small peptides have advantages over antibodies or proteins. For example, small molecules and small peptides exhibit enhanced diffusion, faster blood clearance, and lower background radiation. These carrier allow the facile synthesis of analogs in a high-throughput manner. Additionally, small peptides can be readily converted into peptide mimetics or small molecular analogs that have enhanced stability and improved affinity for the target enzyme or receptor.

In one aspect, the synthesis and methods for using PSMA selective technetium and rhenium complexes according to Formulae I-IV, as novel radiopharmaceuticals for the treatment and imaging of cancer cells, are provided. Specifically, the compounds can be used to target carcinoma of the prostate.

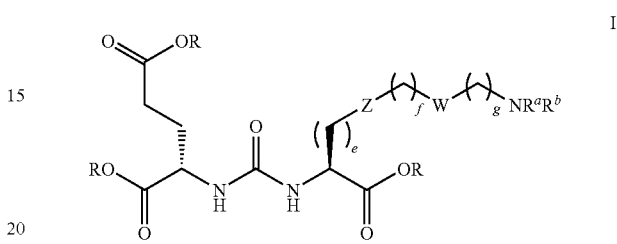

Definitions

For convenience, certain terms employed herein and within the appended claims are collected here.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The use of the terms "a" and "an" and "the" and similar referents in the context of describing the elements (especially in the context of the following claims) are to be construed to cover both the singular and the plural, unless otherwise indicated herein or clearly contradicted by context.

The terms "lipophilic group" and "lipophilic moiety" as used herein refer to a group, moiety or substituent that has a greater affinity for non-polar or non-aqueous environments versus polar or aqueous environments. For example, Merriam Webster's online dictionary defines "lipophilic" as "having an affinity for lipids (as fats)." Exemplary lipophilic moieties include aliphatic hydrocarbon radicals, e.g., alkyl radicals, aromatic hydrocarbon radicals, and long-chain acyl radicals; all of them have increasing lipophilicity as the number of constituent carbons increases. In general, addition of a lipophilic moiety to a particular compound will increase the compound's affinity for octanol in the standard octanol/water partition-coefficient-determination protocol; this protocol may be used to gauge a compound's relative hydrophobicity (lipophilicity) and hydrophilicity.

The terms "Lewis base" and "Lewis basic" refer to a chemical moiety capable of donating a pair of electrons under certain reaction conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. In certain examples, a Lewis base may consist of a single atom, such as oxide ($O_2^-$). In certain, less common circumstances, a Lewis base or ligand may be positively charged. A Lewis base, when coordinated to a metal ion, is often referred to as a ligand.

The term "ligand" refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The term "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" refers to an interaction in which one multi-electron pair donor coordinatively bonds (is "coordinated") to one metal ion.

The term "complex" refers to a compound formed by the union of one or more electron-rich and electron-poor molecules or atoms capable of independent existence with one or more electronically poor molecules or atoms, each of which is also capable of independent existence.

Fmoc is an abbreviation for the chemical group: fluorenylmethyloxycarbonyl.

The phrase "therapeutically-effective amount" as used herein means that amount of a compound, material, or composition comprising a compound which is effective for producing some desired therapeutic effect in at least a sub-population of cells in an animal at a reasonable benefit/risk ratio applicable to any medical treatment.

As used herein, the terms "treating" or "treatment" is intended to encompass also diagnosis, prophylaxis, therapy and cure. The patient receiving this treatment is any animal in need, including primates, in particular humans, and other mammals such as equines, cattle, swine and sheep; and poultry and pets in general.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "amino acid" refers to all compounds, whether natural or synthetic, which include both an amino functionality and an acid functionality, including amino acid analogs and derivatives.

The term "heteroatom" refers to an atom of any element other than carbon or hydrogen. Illustrative heteroatoms include boron, nitrogen, oxygen, phosphorus, sulfur and selenium.

In general, "substituted" refers to an alkyl or alkenyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "alkylcarbonyl" denotes an —($C_1$-$C_8$)alkyl-C(O) group in which one or more methylenes in the $C_1$-$C_8$ alkyl group is replaced with a C(O) group. Representative examples include, but are not limited to, acetyl, propionyl, and $CH_3(CH_2)_2C(O)$— group.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. Cycloalkyl groups may be substituted or unsubstituted. Cycloalkyl or cyclic alkyl groups include mono-, bi- or tricyclic alkyl groups having from 3 to 14 carbon atoms in the ring(s), or, in some embodiments, 3 to 12, 3 to 10, 3 to 8, or 3 to 4, 5, 6 or 7 carbon atoms. Exemplary monocyclic cycloalkyl groups include, but not limited to, cyclopropyl, cyclobutyl, cyclopentyl, cyclohexyl, cycloheptyl, and cyclooctyl groups. Bi- and tricyclic ring systems include both bridged cycloalkyl groups and fused rings, such as, but not limited to, bicyclo[2.1.1]hexane, adamantyl, decalinyl, and the like.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to vinyl, allyl, —CH═CH($CH_3$), —CH═C($CH_3$)$_2$, —C($CH_3$)═$CH_2$, —C($CH_3$)═CH($CH_3$), —C($CH_2CH_3$)═$CH_2$, cyclohexenyl, cyclopentenyl, cyclohexadienyl, butadienyl, pentadienyl, and hexadienyl, among others. Alkenyl groups may be substituted or unsubstituted. Representative substituted alkenyl groups may be mono-substituted or substituted more than once, such as, but not limited to, mono-, di- or tri-substituted with substituents such as those listed above.

Alkynyl groups include straight and branched chain and cycloalkyl groups as defined above, except that at least one triple bond exists between two carbon atoms. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Aryl group includes both substituted and unsubstituted aryl groups. Substituted aryl groups may be monosubstituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms.

Heterocyclyl groups includes non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, monoalkylamino, dialkylamino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" refers to an aromatic or non-aromatic ring in which each atom of the ring is carbon.

The term "nitro" refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The term "amine or amino" refers to an —NR$^c$R$^d$ group wherein R$^c$ and R$^d$ each independently refer to a hydrogen, (C$_1$-C$_8$)alkyl, aryl, heteroaryl, and heterocycloalkyl group. When R$^c$ and R$^d$ are attached to the same nitrogen atom, they can be combined with the nitrogen atom to form a 5-, 6- or 7-membered ring. For example, —NR$^c$R$^d$ is meant to include 1-pyrrolidinyl, pyridinyl or a 4-morpholinyl ring.

The term "amido" is art recognized as an amino-substituted carbonyl and includes a moiety that may be represented by the general formula, —C(O)NR$^c$R$^d$ group wherein R$^c$ and R$^d$ are as defined above. According to some embodiments, the amide does not include imides which may be unstable.

The terms "carboxyl" and "carboxylate" are include such moieties as may be represented by the general formulas:

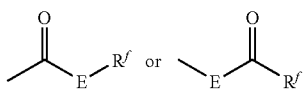

wherein E is a bond or represents O or S, and R$^f$ and R$^{f'}$ individually is H, alkyl, alkenyl, aryl, or a pharmaceutically acceptable salt. Where E is O, and R$^f$ is as defined above, the moiety is referred to herein as a carboxyl group, and particularly when R$^f$ is a hydrogen, the formula represents a "carboxylic acid". In general, where the expressly shown oxygen is replaced by sulfur, the formula represents a "thiocarbonyl" group.

The terms "alkoxyl" or "alkoxy" refer to an alkyl group, as defined above, having an oxygen radical attached thereto. Representative alkoxyl groups include methoxy, ethoxy, propoxy, butyoxy, tert-butoxy and the like. An "ether" is two hydrocarbons covalently linked by an oxygen. "Ether" also encompasses polyethers where more than one ether group, or linkage, may be present in a given group. "Ether" also encompasses cyclic ethers, and crown ethers, where the ether linkage is within a cyclic group.

The term "sulfonate" refers to a moiety that may be represented by the general formula, —S(O)$_2$OR$^g$, in which R$^g$ is an electron pair, hydrogen, alkyl, cycloalkyl, or aryl. The term "sulfate" includes a moiety that may be represented by the general formula, —OS(O)$_2$OR$^g$, in which R$^g$ is as defined above. The term "sulfonamido" includes a moiety that may be represented by the general formula: —N(R$^f$)S(O)$_2$OR$^{f'}$, in which R$^f$ and R$^{f'}$ are as defined above. The term "sulfamide" refers to a moiety that may be represented by the general formula, —S(O)$_2$NR$^e$R$^f$, in which in which R$^e$ and R$^f$ are hydrogen, (C$_1$-C$_8$)alkyl or aryl. The term "sulfonyl" refers to a moiety that may be represented by the general formula: —S(O)$_2$R$^h$, in which R$^h$ is one of the following: hydrogen, alkyl, alkenyl, alkynyl, cycloalkyl, heterocyclyl, aryl or heteroaryl.

The definition of each expression, e.g. alkyl, m, n, and the like, when it occurs more than once in any structure, is intended to be independent of its definition elsewhere in the same structure.

The terms triflyl, tosyl, mesyl, and nonaflyl refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain the groups, respectively. The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in the compositions may exist in particular geometric or stereoisomeric forms. In addition, compounds may also be optically active. The compounds may also include cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. If, for instance, a particular enantiomer of compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 3$^{rd}$ ed.; Wiley: New York, 1999).

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

Chelator Compounds and their Synthesis

In one aspect, a compound of Formula I, its pharmaceutically acceptable salts and solvates are provided:

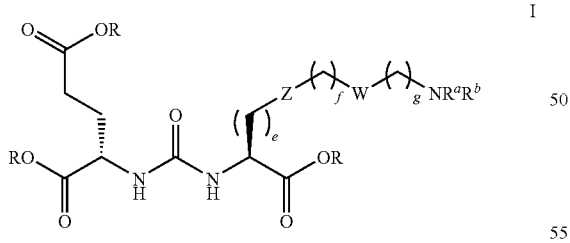

I where, R is H, an ammonium ion, an alkylammonium ion, an alkaline earth metal ion, a rare earth metal ion, or an alkyl group; W is a bond, —NHC(O)—, —CH(NH$_2$)—, —NH—C(O)—NH—, —C(O)—NH—, —C(O)—NH—CH(COOH)—, —O—(CH$_2$)$_n$—O—(CH$_2$)$_n$—, —(CH$_2$)$_n$O(CH$_2$)$_n$O(CH$_2$)$_n$—, —CH(NHFmoc)-; Z is a bond, —CO(O)—, —NH—, —NHC(O)—, —NH—C(O)—NH—, —NH—C(O)—(CH$_2$)$_n$—, —NH—C(O)—CH(NH$_2$)—, —C(O)—NH—CH(COOH)—; or —NH—C(O)—C$_6$H$_4$—(CH$_2$)$_n$—NH—; NR$^a$R$^b$ is absent or is a chelator group of Formula:

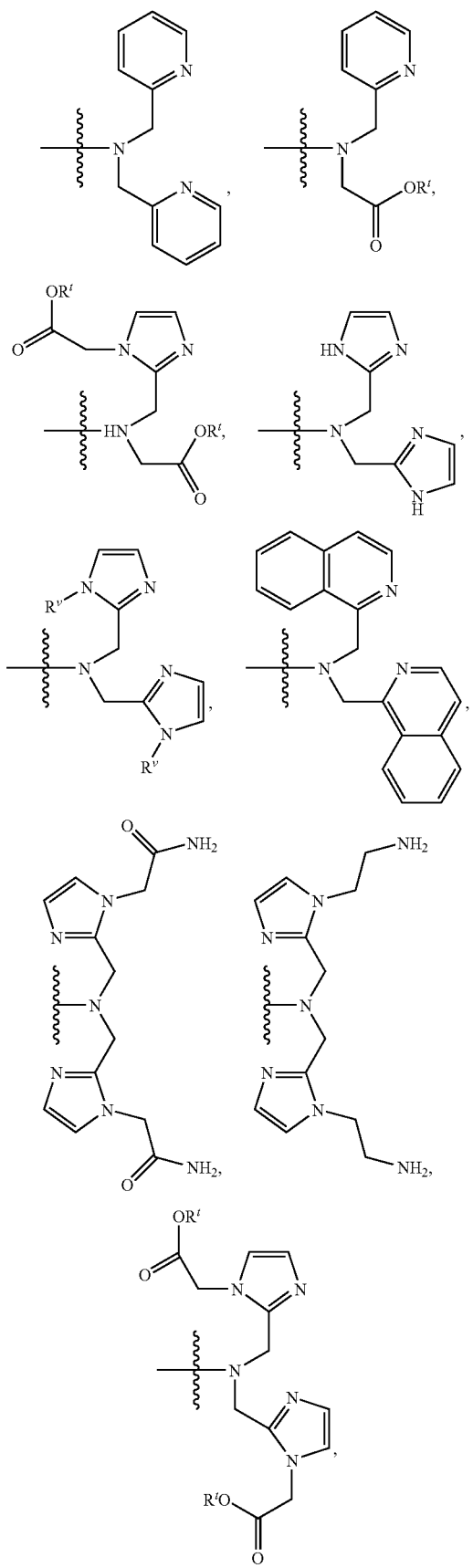

-continued

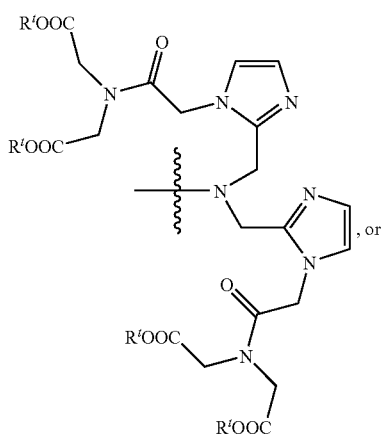

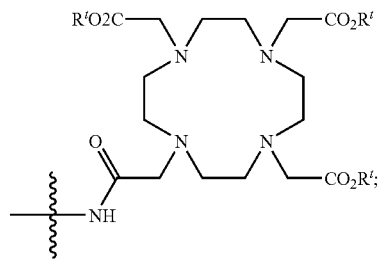

$R^t$ is H, a $C_1$-$C_8$ alkyl group, an ammonium ion, an alkylammonium ion, or an alkali or alkaline earth metal ion; $R^v$ is alkyl; e is an integer from 0 to 15; f is an integer from 0 to 15; g is an integer from 0 to 15; and n is an integer from 0 to 10; with the proviso that where $NR^aR^b$ is:

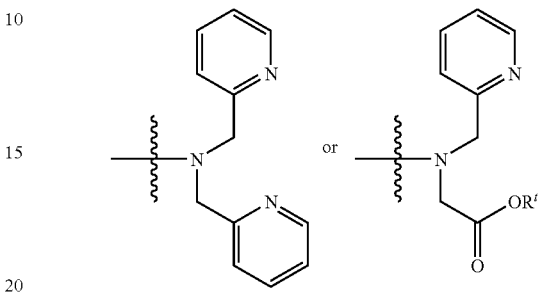

then where W is a bond, Z are other than a bond, —C(O)—NH—, or —NHC(O)—; and where Z is a bond, W is other than a bond, —C(O)—NH—, or —NHC(O)—. In some embodiments, R is alkyl. In other embodiments, $R^v$ is methyl, ethyl, n-propyl, iso-propyl, n-butyl, iso-butyl, or tert-butyl. In yet other embodiments, $R^v$ is methyl. In yet other embodiments, each $R^t$ is independently H or tert-butyl. In yet other embodiments, $R^t$ is H.

Example compounds according to Formula I, include, but are not limited to:

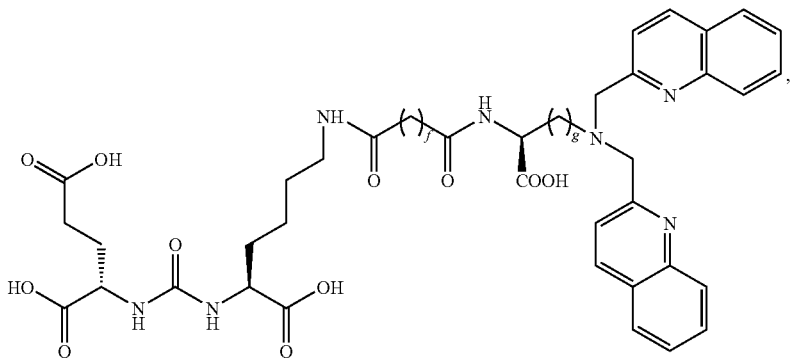

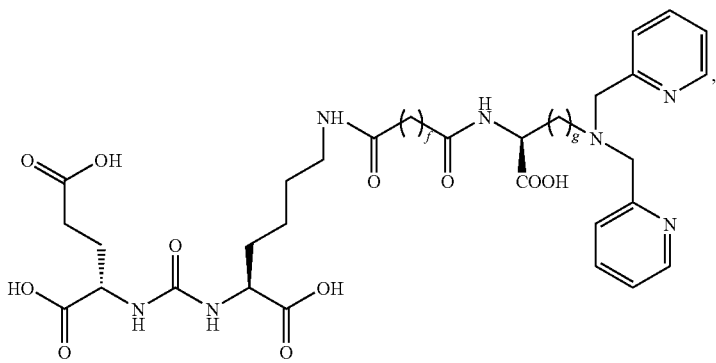

-continued
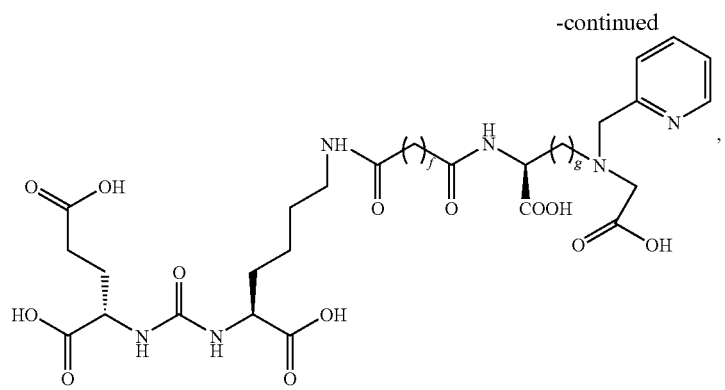
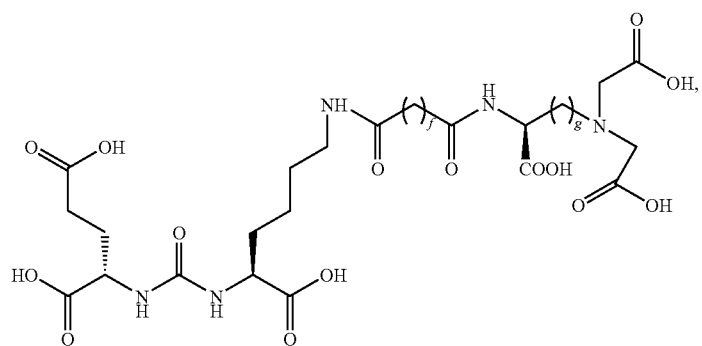
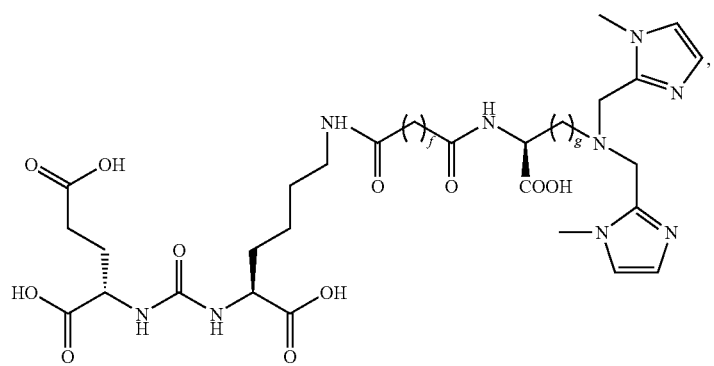
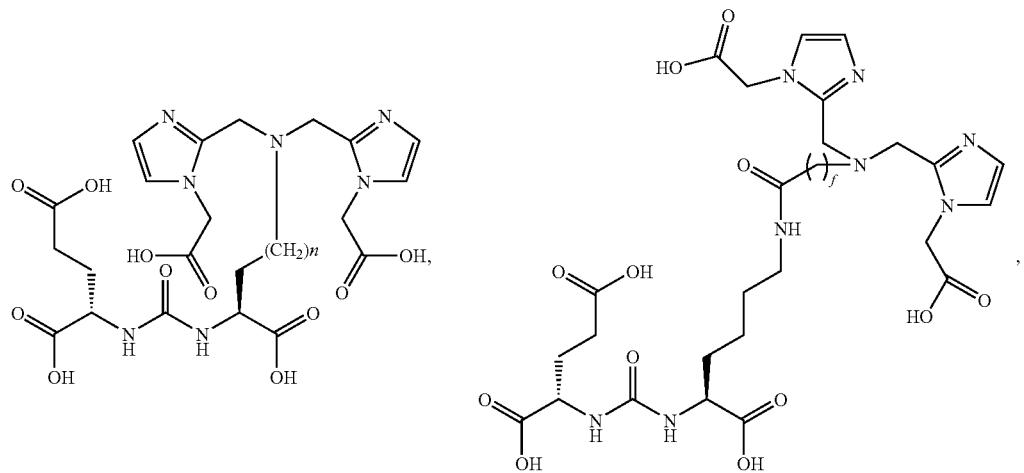

-continued
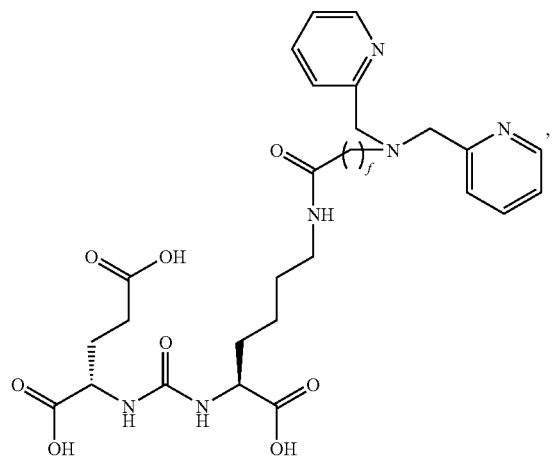
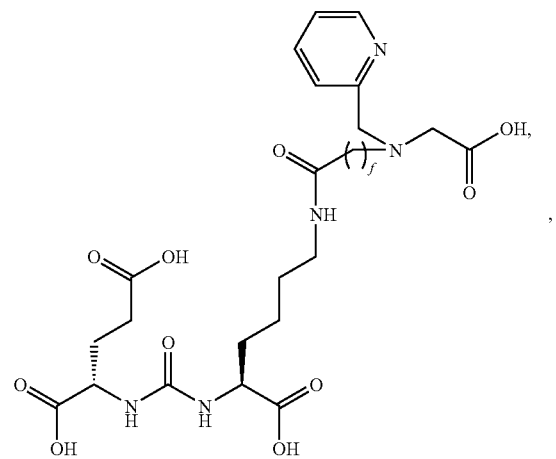
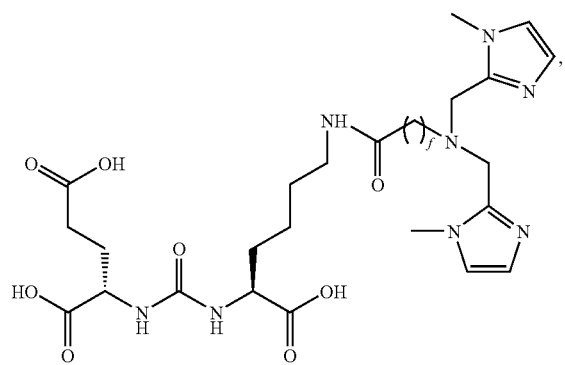
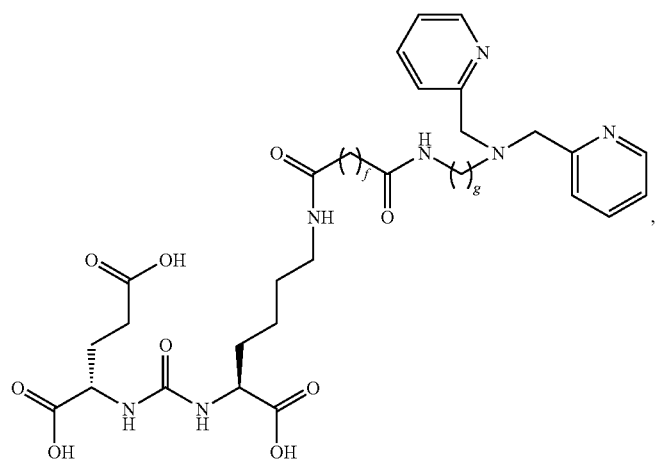
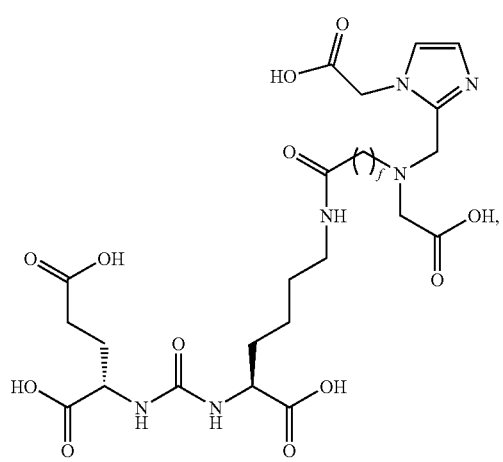

-continued
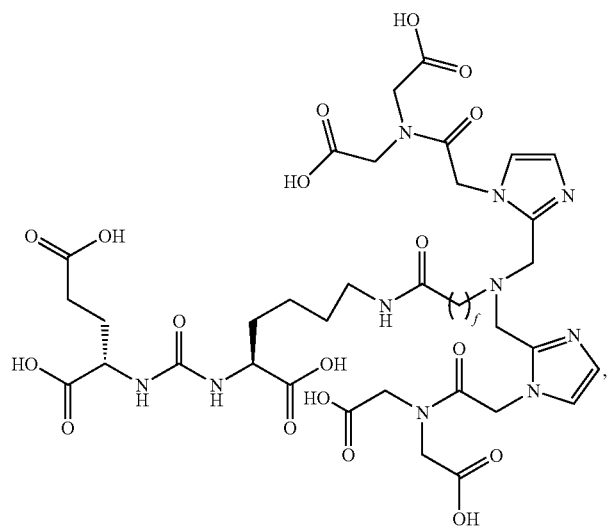
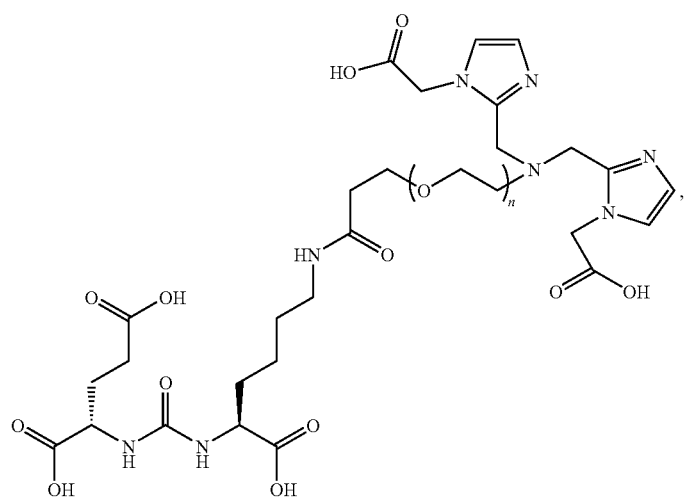
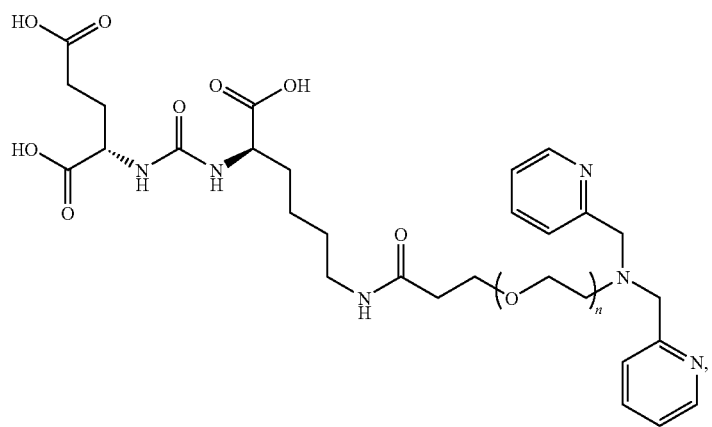

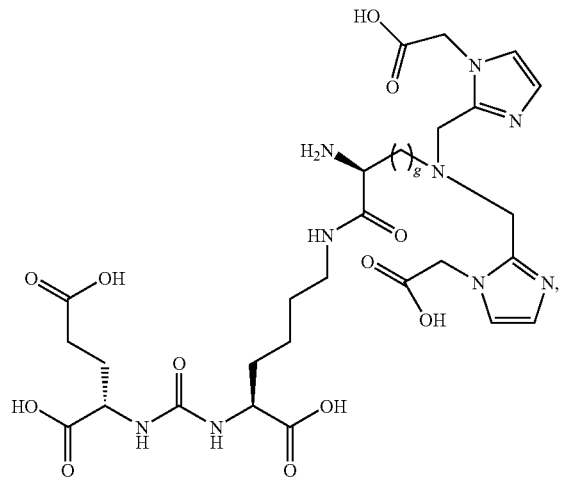
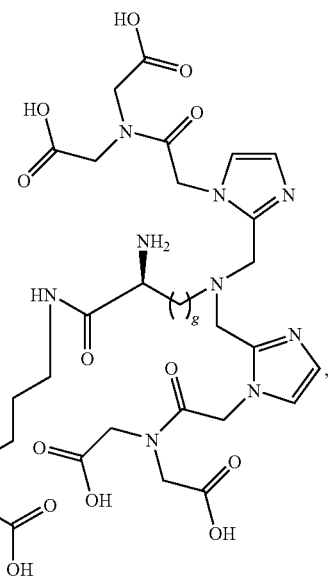
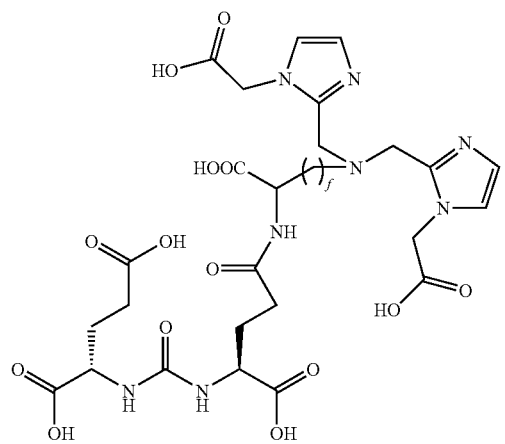
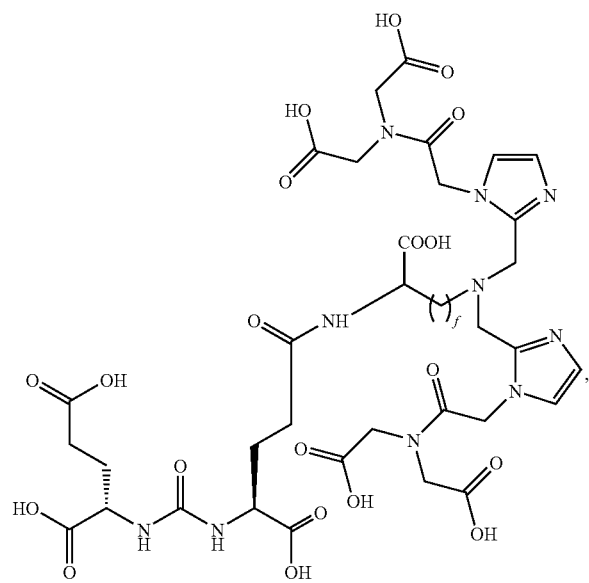
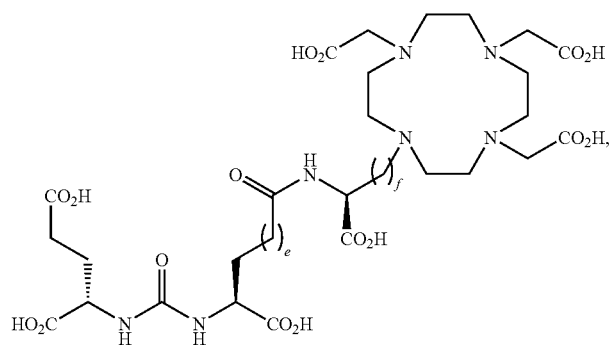

-continued

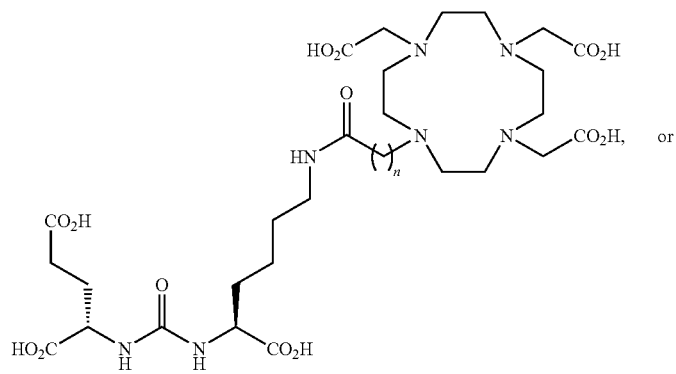

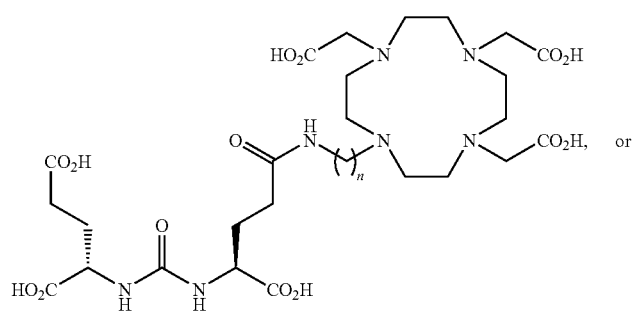

pharmaceutically acceptable salts and solvates thereof; where e is an integer from 0 to 10; f is an integer from 0 to 10; g is an integer from 0 to 10; and n is an integer from 0 to 10.

According to various embodiments, the $NR^aR^b$ group of the compound may further be chelated to a metal. In some embodiments, the metal is a radioactive nuclide. For example, the metal may be technetium-99m, or rhenium-186 m/188m. Complexes such as $[NEt_4]_2[MBr_3(CO)_3]$; M is Tc or Re, may be reacted with a compound of Formula I in an alcoholic solvent. Such a reaction provides the chelated complex of Formula I-M, as further described below:

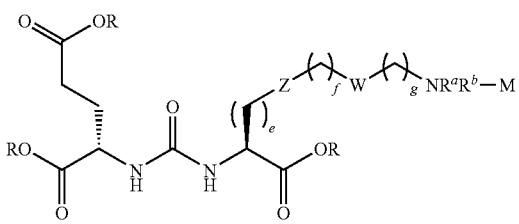

I-M

Illustrative compounds according to Formula I-M, include, but are not limited to any one of the following:

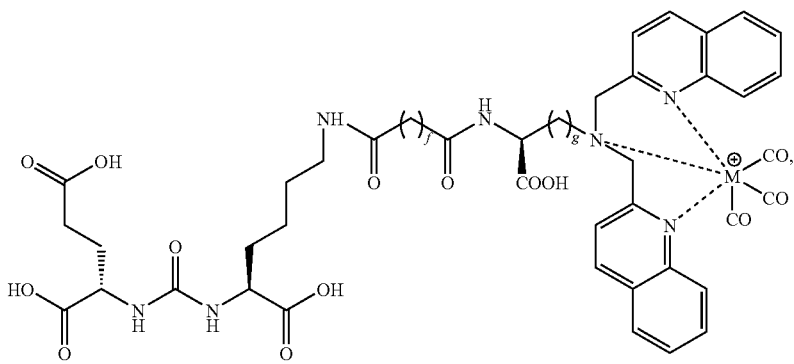

-continued
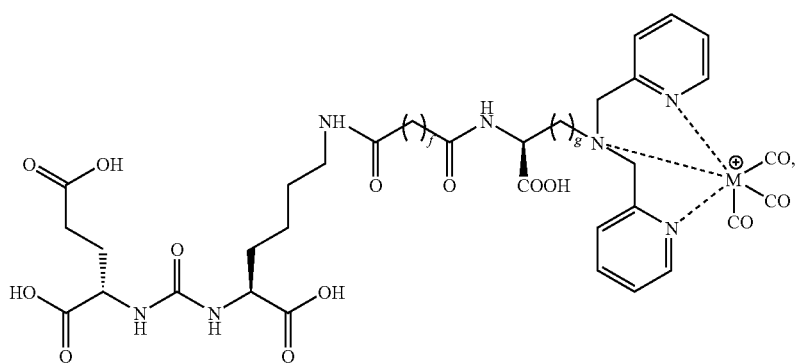
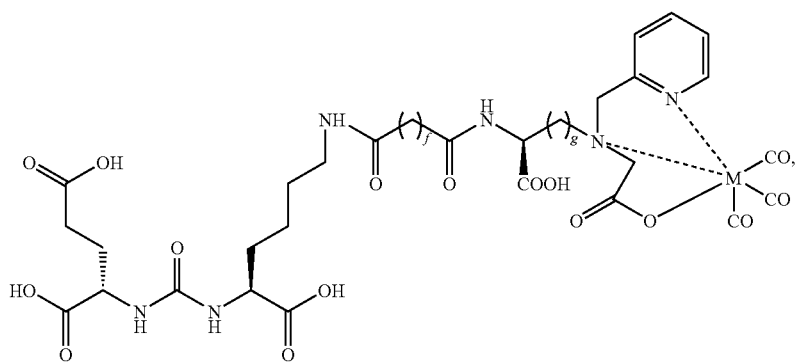
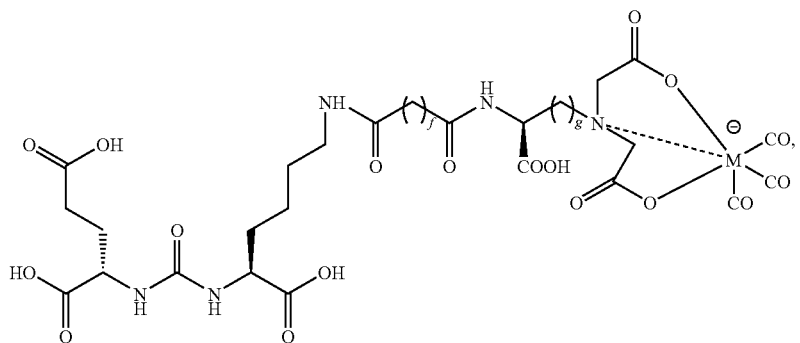
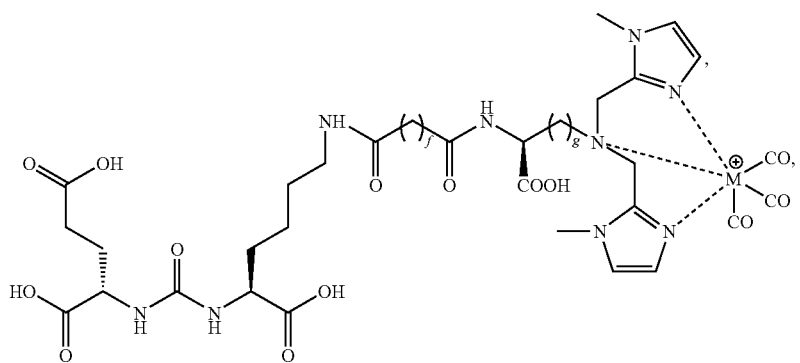

-continued
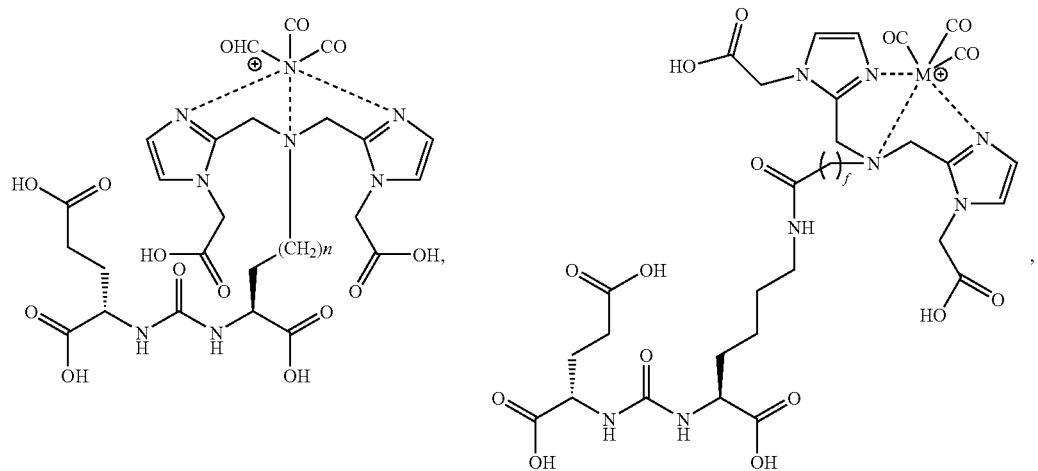
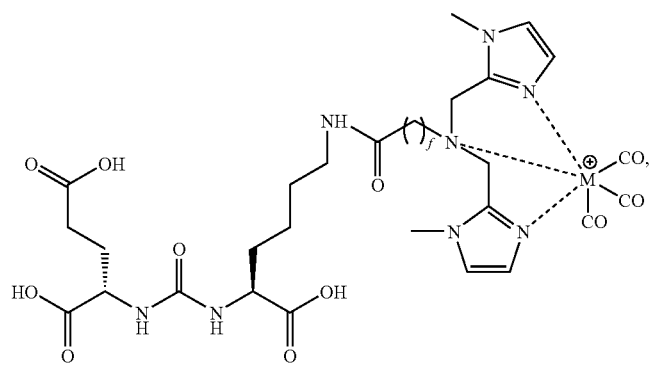
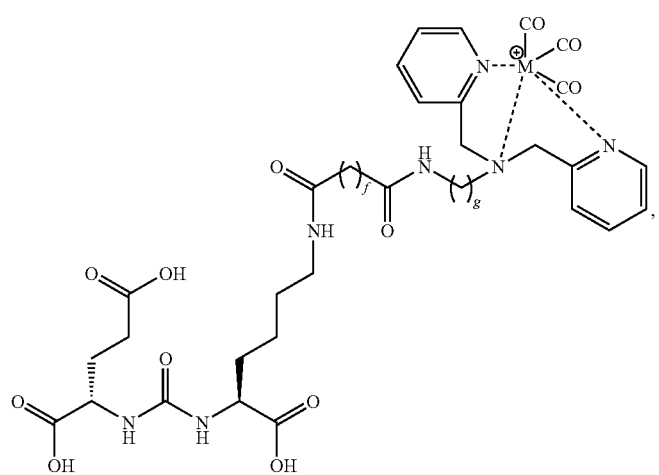

-continued
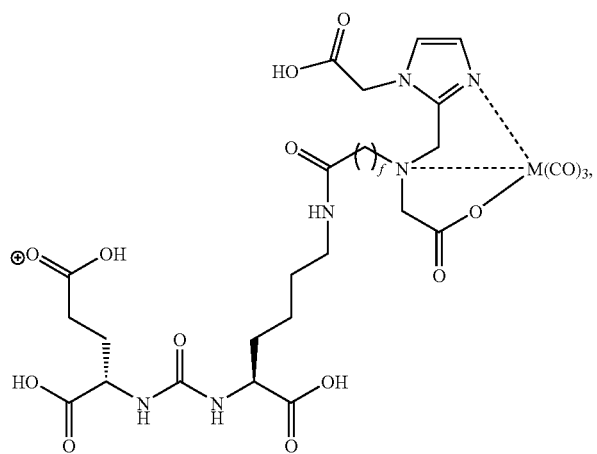
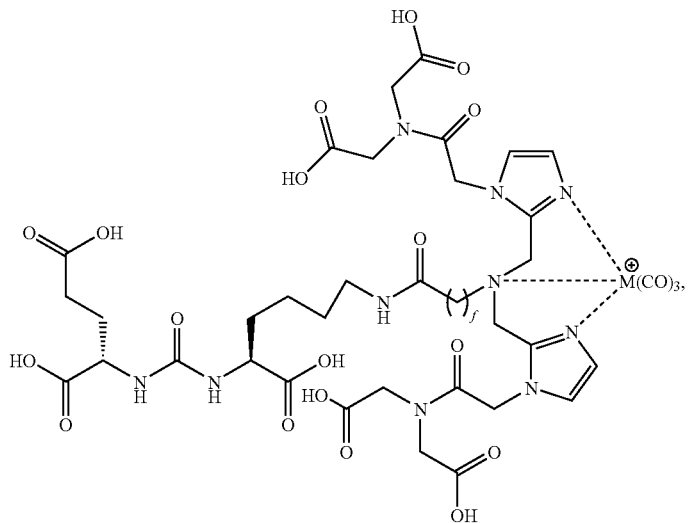
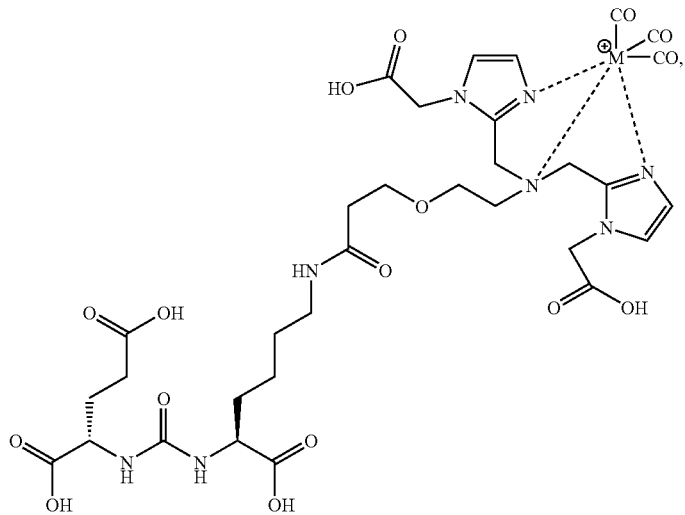

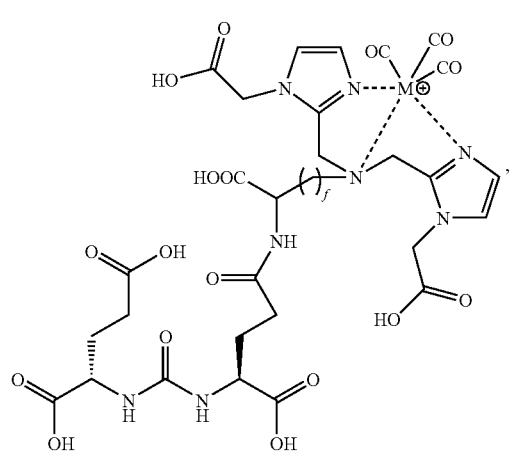
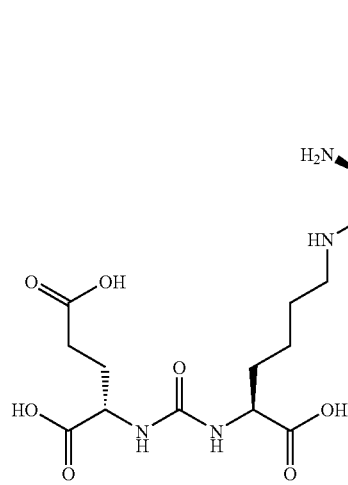
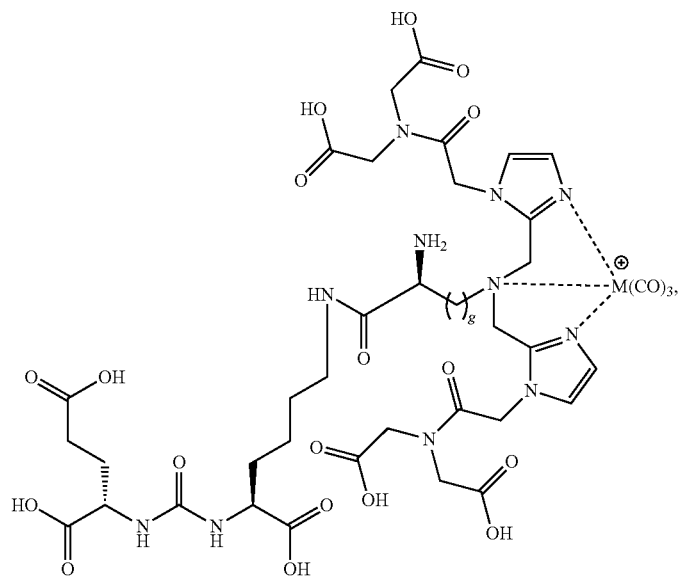
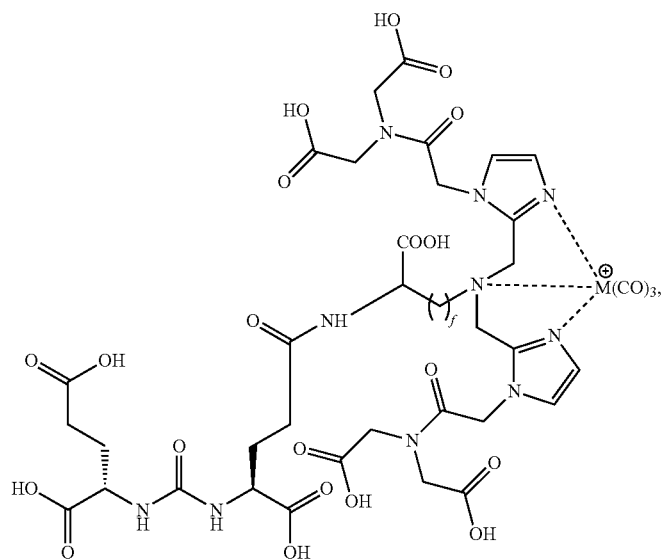

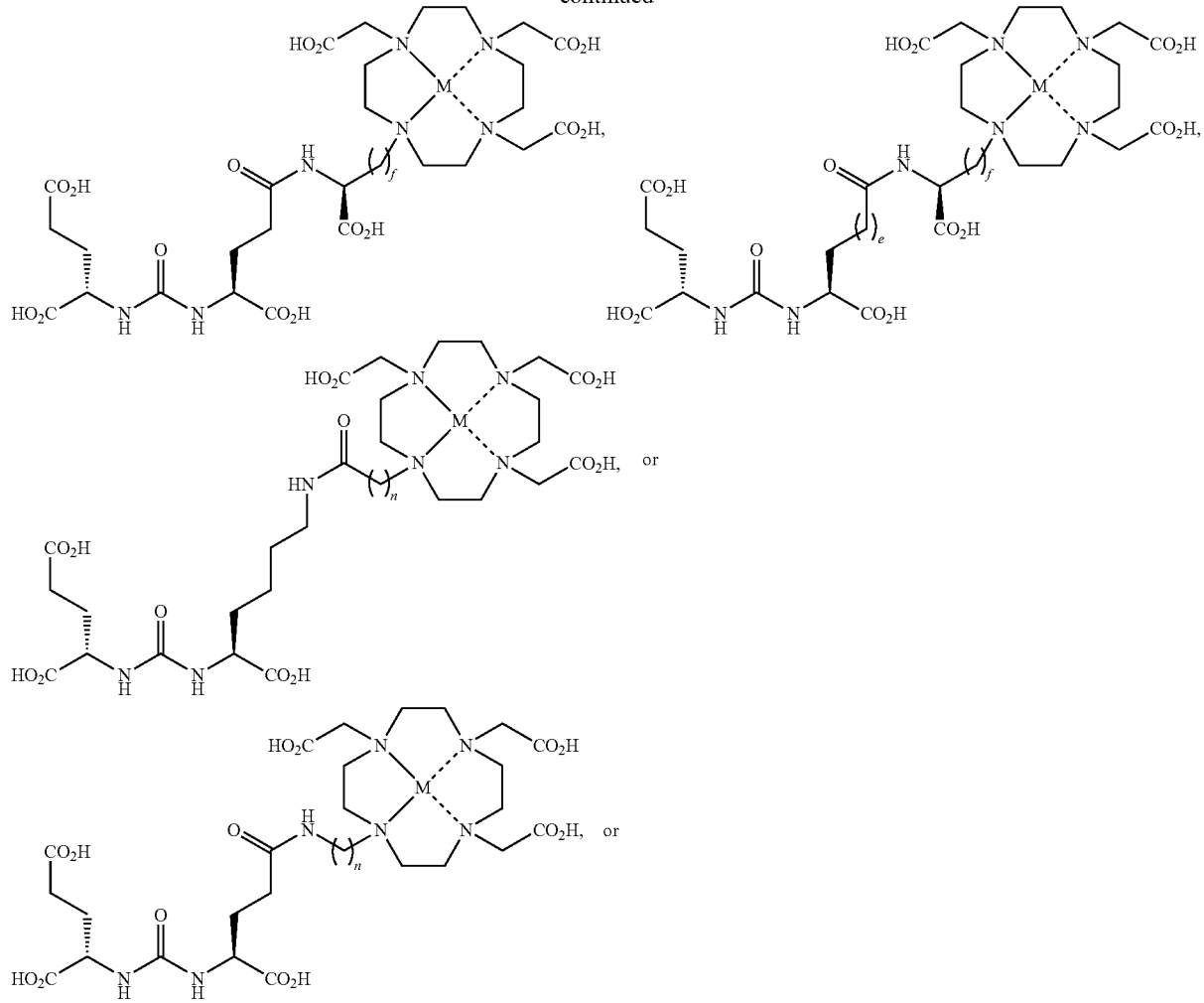

pharmaceutically acceptable salts and solvates thereof; where, M is Re or Tc; e is an integer from 0 to 10; f is an integer from 0 to 10; g is an integer from 0 to 10; and n is an integer from 0 to 10.

In some embodiments, the compounds include not only pharmaceutically acceptable salts and solvates thereof, but also stereoisomers, tautomers, and prodrugs of such compounds.

As noted above, complexes of the compound of Formula I may contain one or more a radionuclides which are suitable for use as radio-imaging agents and as therapeutics for the treatment of rapidly proliferating cells. Accordingly, in one embodiment, a pharmaceutical composition is provided including a complex that includes a metal and the compound of Formula I a salt, solvate, stereoisomer, or tautomer thereof, and a pharmaceutically acceptable carrier.

In general, metal complexes of the compound Formula I or pharmaceutical compositions thereof, may be administered orally, or via a parenteral route, usually by injection. Parenteral routes include, but are not limited to, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. In some embodiments, the compound, or pharmaceutical composition thereof, is administered orally. Such compositions may take the form of tablets, pills, capsules, semisolids, powders, solutions, suspensions, elixirs, aerosols, or any other appropriate compositions.

According to another aspect, a pharmaceutical composition is provided, which is suitable for in vivo imaging. Such suitable imaging pharmaceutical compositions contain an imaging agent that has a radionuclide either as an element, i.e. radioactive iodine, or a radioactive metal chelate complex of the compound of Formula I in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl)aminomethane (and its salts), phosphate, citrate, bicarbonate, etc; sterile water; physiological saline; and balanced ionic solutions containing chloride and or dicarbonate salts or normal blood plasma cations such as calcium, potassium, sodium, and magnesium.

The concentration of the imaging agent in the radiological vehicle should be sufficient to provide satisfactory imaging. For example, when using an aqueous solution, the dosage is about 1.0 to 50 millicuries. The imaging agent should be administered so as to remain in the patient for about 1 to 24 hours, although both longer and shorter time periods are acceptable. Therefore, convenient ampoules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera. In certain embodiments, a method of imaging a region in a patient includes the steps of: administering to a patient a diagnostically effective amount of a compound complexed with a radionuclide; exposing a region of the patient to radiation; and obtaining an image of the region of the patient. In certain embodiments of the region imaged is the head or thorax. In other embodiments, the compounds and complexes of Formula I target the PSMA protein.

Figure 5:
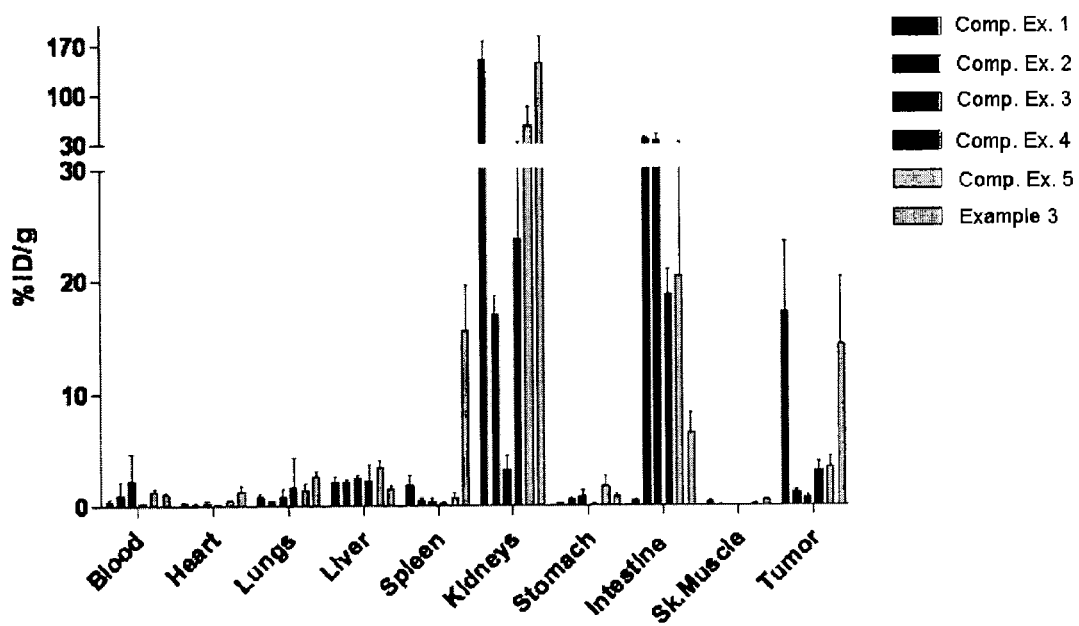
FIG. 5 is a graph comparing the tissue biodistribution for $^{99m}$Tc complexes in LNCaP Xenograft mice in % ID/g.

Thus, in some embodiments, a method of imaging tissue such as spleen tissue, kidney tissue, or PSMA-expressing tumor tissue is provided including contacting the tissue with a complex including a radioactive metal and a compound including a group of formula:

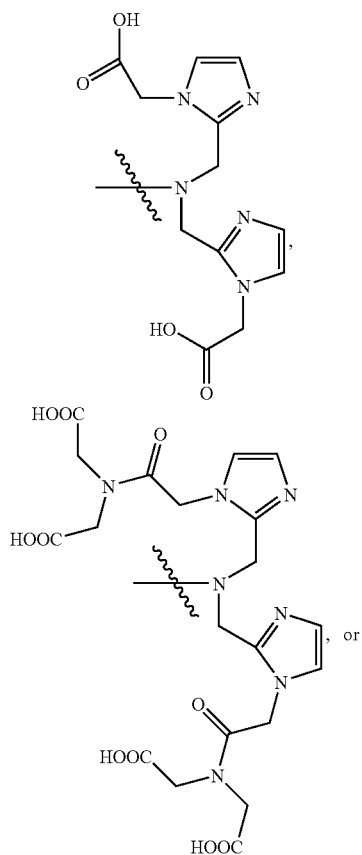

a pharmaceutically acceptable salt or solvate thereof. In some embodiments, the tissue is PSMA-expressing tumor tissue. The specificity of such compounds, are illustrated in FIG. 5.

The present invention, thus generally described, will be understood more readily by reference to the following examples, which are provided by way of illustration and are not intended to be limiting of the present invention.

EXAMPLES

General Synthetic Methods

General procedure for complexation of the compounds with a metal. As exemplified herein, rhenium is used as the metal in consideration of the availability of non-radioactive isotopes and the safety of workers. However, as is to be understood, similar synthetic procedures may be followed using the technetium analogs, as technetium and rhenium have similar reaction chemistry and are of a similar size due to the lanthanide contraction. Therefore, where Re may be specifically shown, it is understood to include Tc complexes as well.

General Experimental Conditions for the Formation of the Rhenium Complexes

The rhenium/technetium complexes of the compounds of Formula I are conveniently isolated from the reactions of the readily available precursor $[NEt_4]_2[Re(CO)_3Br_3]$ with the compound. Since the donor sets provided by the SAAC terminus are well documented as effective chelators for the $\{M(CO)_3\}^{+1}$ core and have been designed to adopt the required facial arrangement about the metal site, the preparations of the complexes are unexceptional.

The $\{Re(I)(CO)_3\}^+$ system follows similar reaction chemistry to that of the $^{99m}$Tc-tricarbonyl core. The use of $[NEt_4]_2[ReBr_3(CO)_3]$, as the starting material leads to facile formation of the fac-$\{Re(CO)_3(L)_3\}$ core. The $[NEt_4]_2[ReBr_3(CO)_3]$ is readily derived from the $[ReBr(CO)_5]$. The synthesis of the Re(I) complexes is accomplished by reacting $[NEt_4]_2[ReBr_3(CO)_3]$ with the appropriate chelating ligand in the ratio of 1:1.2 in 10 ml of methanol. The reaction mixture is allowed to heat at 80° C. for 4 hours. After cooling all of the reaction products are all purified using C18 Sep Pak columns with yields ranging from 20-50%.

Unless otherwise noted the synthesis of the Re(I) complexes was accomplished by reacting $[NEt_4]_2[ReBr_3(CO)_3]$ (or, $[^{99m}Tc(CO)_3(H_2O)_3]^+$) with the appropriate ligand ($10^{-6}$ M-$10^{-4}$ M) in the ratio of 1:1.2 in 10 ml of methanol. The sealed vial was heated at was allowed to heat at 100° C. for 4 hours. Upon cooling the reaction was analyzed for purity via RP-HPLC (reverse phase-HPLC) and the product was purified using a silica column using methanol as the eluent. The radiochemical purity (RCP) after HPLC purification, resulting in "carrier free" products, was determined via HPLC and shown to be consistently ≧95%. Although initial results demonstrated radiolabeling at concentrations as low as $10^{-6}$ M RCY was ≦0.80%. RCY is an abbreviation for radiochemical yield. To achieve a RCY>95% at 75° C., the reaction concentration needed to be increased to $10^{-4}$ M. In many cases, the corresponding Tc complexes are prepared and tested as the Re complexes in order to prepare non-radioactive analogs for testing and handling purposes.

Radiolabeling of the Compounds.

Radiolabeling of the compounds of Formula I was accomplished to form complexes on either the free α-amino acids or as the appropriately N-protected amino acid derivative utilizing similar methodology. The $^{99m}Tc(I)(CO)_3^+$ radiolabeling was accomplished in two steps using the commercially available IsoLink™ kits (Covidien) to form the $[^{99m}Tc(CO)_3(H_2O)_3]^+$ intermediate, which was reacted with the appropriate compound of Formula I ($10^{-6}$ M-$10^{-4}$ M) in an equal volume mixture of 1:1 acetonitrile and phosphate buffer. The sealed vial was heated at 100° C. for 30 minutes. Upon cooling, the reaction was analyzed for purity via RP-HPLC. The radiochemical purity (RCP) after HPLC purification, resulting in "carrier free" products, was determined via HPLC and shown to be consistently ≧95%. Although initial results demonstrated radiolabeling at concentrations as low as $10^{-6}$ M RCY was ≦80%. To achieve a RCY>95% at 75° C., the reaction concentration needed to be increased to $10^{-4}$ M. In many cases, the corresponding Re complexes are prepared and tested as the Tc complexes in order to prepare non-radioactive analogs for testing and handling purposes. Therefore, where Re may be specifically shown, it is understood to include Tc complexes as well.

Synthesis of Exemplary Formula I Compounds

Scheme 1 is an illustration of the general synthetic route for Glu-urea-imidazole based compounds. The first step, depicted in Scheme 1, is performed at 0° C. under inert conditions using the di-t-butyl ester of Glutamic acid with CDI in the presence of base to form the intermediate Glu-urea-imidazole derivative 2. This intermediate is activated with MeoTf under basic conditions to afford the methylated imidazole, which under inert conditions reacts readily with amines. The tert-butyl ester protecting groups are removed using 20% TFA in DCM for 1 to 4 hour at room temperature. Upon completion of the deprotection, the reaction mixture is concentrated on a rotary evaporator or blown dry with nitrogen and purified on a silica column or recrystallized.

Scheme 1

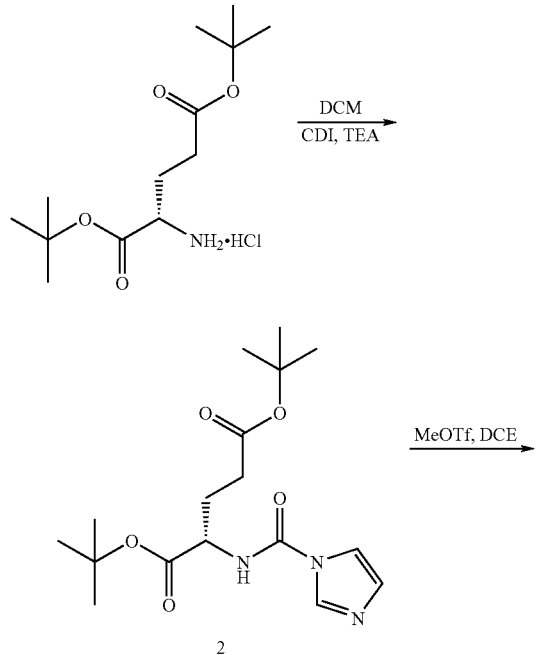

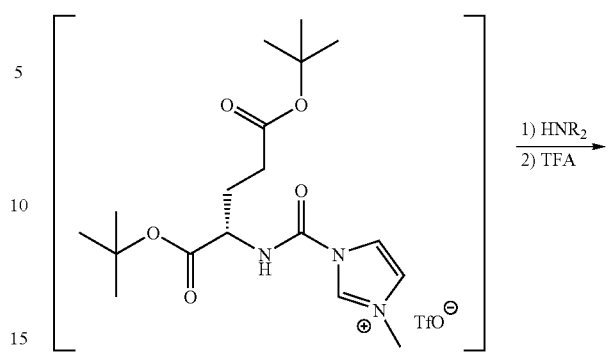

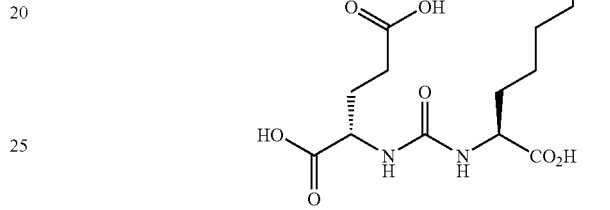

The compounds of the general structure E were prepared in overall yields ranging from 10-50% using the general route depicted in Scheme 2. The key synthetic intermediate was formed by reaction of the appropriate aldehyde at room temperature for one hour to form the intermediate Schiff base. The Schiff's base was not isolated but was reduced in situ with sodium triacetoxyborohydride to form the bis-derivatized amine (B). The derivatized amine was coupled to 2-[3-(5-Amino-1-tert-butoxycarbonyl-pentyl)-ureido]-pentanedioic acid di-tert-butyl ester (A) using the terminal carboxylic acid, HATU (2-(1H-7-Azabenzotriazol-1-yl)-1,1,3,3-tetramethyl uronium hexafluorophosphate Methanaminium) and base to form the protected intermediate C. The synthesis of the Re(I) complexes (D) was accomplished by reacting [NEt$_4$]$_2$[ReBr$_3$(CO)$_3$] with the appropriate ligand in the ratio of 1:1.2 in 10 ml of methanol. The reaction was allowed to heat at 80° C. for 4 hours. After cooling all of the following reaction products were all purified using C18 Sep Pak columns with yields ranging from 20-50%.

Scheme 2. General pathway for the synthesis of M-Glu-Urea-Lys-X analogs (E).

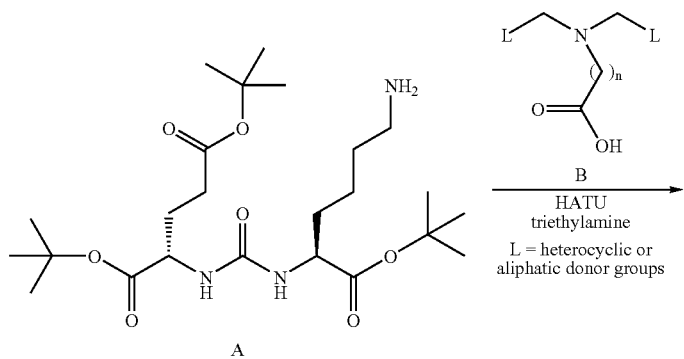

-continued

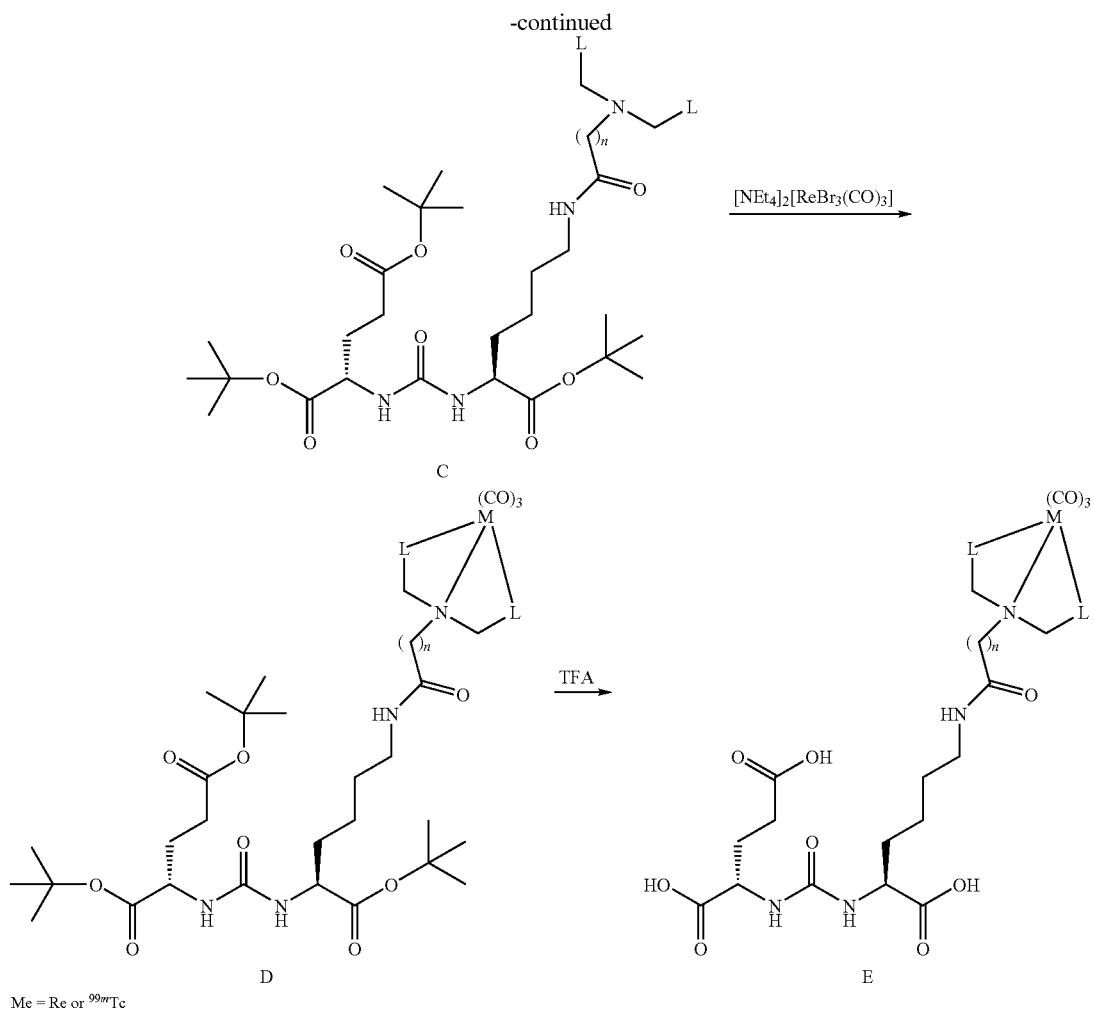

Me = Re or $^{99m}$Tc

The tert-butyl ester protecting groups were removed using 50% TFA in DCM for 12 hours at room temperature. Upon completion of the deprotection, the reactions were concentrated on a rotary evaporator and purified by HPLC or flash chromatography to afford the desired products (E) in 10-50% yield.

Example 1

[Re(CO)$_3${(S)-2-(3-((R)-5-(bis((1-(carboxymethyl)-1H-imidazol-2-yl)methyl)amino)-1-carboxypentyl)ureido)pentanedioic acid}]

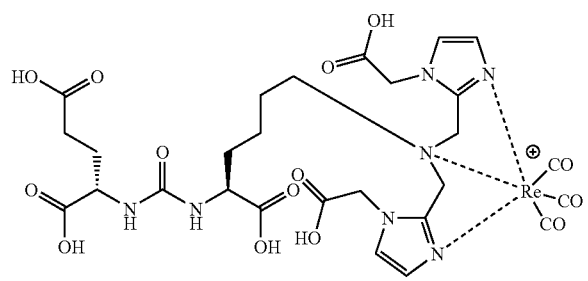

(S)-2-(3-((R)-5-(bis((1-(carboxymethyl)-1H-imidazol-2-yl)methyl)amino)-1-carboxypentyl)ureido)pentanedioic acid was prepared employing the same general procedure as shown in Scheme 1, using 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods employing TFA to yield the desired product (4.0 mg, 29%) as an off-white solid. $^1$H NMR (400 MHz, DMSO-d$_6$) δ 7.2 (s, 2H), 7.0 (s, 2H), 6.3 (s, 2H), 4.85 (s, 4H), 4.55 (d, 2H), 4.4 (d, 2H), 4.10 (s, 2H), 3.5 (s, 2H), 2.2 (m, 2H), 1.7 (m, 6H), 1.25 (m, 2H). ESMS m/z: 866 (M+H)$^+$.

Example 2

[Re(CO)$_3${(14R,18S)-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid}]

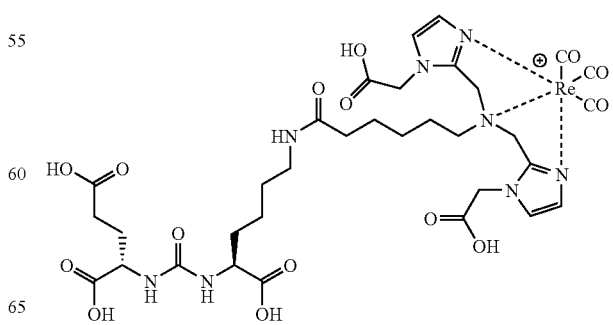

(14R,18S)-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid was prepared employing the same general procedure as shown in Scheme 1, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods employing TFA to yield the desired product (8.0 mg, 13%) as an off-white solid. $^1$H NMR (400 MHz, DMSO-$d_6$) δ 7.9 (s, H), 7.2 (s, 2H), 7.0 (2, 2H), 6.3 (s, 2H), 4.85 (s, 4H), 4.55 (d, 2H), 4.4 (d, 2H), 4.1 (m, 2H), 3.5 (s, 2H), 2.9 (s, 4H), 2.2 (m, 2H), 2.05 (m, 2H), 1.85 (m, 2H), 1.6 (m, 6H), 1.3 (m, 4H). ESMS m/z: 979 (M+H)$^+$.

Example 3

[Re(CO)$_3${(19R,23S)-1-(1-(carboxymethyl)-1H-imidazol-2-yl)-2-((1-(carboxymethyl)-1H-imidazol-2-yl)methyl)-13,21-dioxo-2,14,20,22-tetraazapentacosane-19,23,25-tricarboxylic acid}]

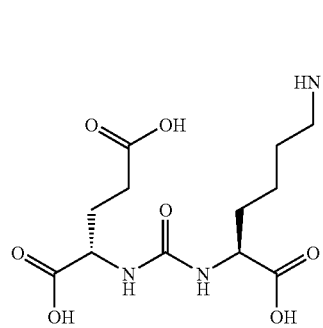
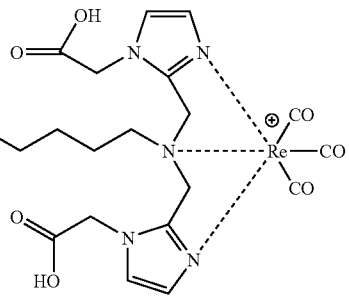

(19R,23S)-1-(1-(carboxymethyl)-1H-imidazol-2-yl)-2-((1-(carboxymethyl)-1H-imidazol-2-yl)methyl)-13,21-dioxo-2,14,20,22-tetraazapentacosane-19,23,25-tricarboxylic acid was prepared employing the same general procedure as shown in Scheme 1, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods employing TFA to yield the desired product (7.0 mg, 24%) as an off-white solid. $^1$H NMR (400 MHz, DMSO-$d_6$) δ 7.8 (s, H), 7.2 (s, 2H), 7.0 (2, 2H), 6.3 (s, 2H), 4.8 (s, 4H), 4.55 (d, 2H), 4.4 (d, 2H), 4.1 (m, 2H), 3.5 (m, 2H), 2.9 (m, 2H), 2.2 (m, 2H), 2.05 (m, 4H), 1.9 (m, 4H), 1.6 (m, 4H), 1.4 (m, 2H) 1.3 (m, 16H). ESMS m/z: 525 (M/2).

Example 4

[Re(CO)$_3${(17R,21S)-1-(1-(carboxymethyl)-1H-imidazol-2-yl)-2-((1-(carboxymethyl)-1H-imidazol-2-yl)methyl)-11,19-dioxo-5,8-dioxa-2,12,18,20-tetraazatricosane-17,21,23-tricarboxylic acid}]

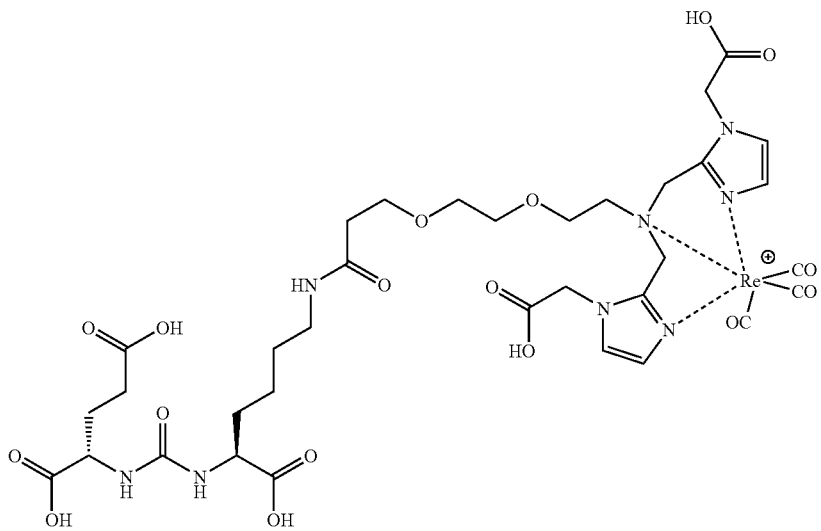

(17R,21S)-1-(1-(carboxymethyl)-1H-imidazol-2-yl)-2-((1-(carboxymethyl)-1H-imidazol-2-yl)methyl)-11,19-dioxo-5,8-dioxa-2,12,18,20-tetraazatricosane-17,21,23-tricarboxylic acid was prepared employing the same general procedure as shown in Scheme 1, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods employing TFA to yield the desired product (6.0 mg, 38%) as an off-white solid. $^1$H NMR (400 MHz, DMSO-$d_6$) δ 7.9 (s, H), 7.2 (s, 2H), 7.0 (s, 2H), 6.3 (s, 2H), 4.85 (s, 4H), 4.6 (d, 2H), 4.5 (d, 2H), 3.80 (m, 12H), 3.5 (m, 10H), 2.4 (m, 4H). ESMS m/z: 738 (M+H)$^+$.

Example 5

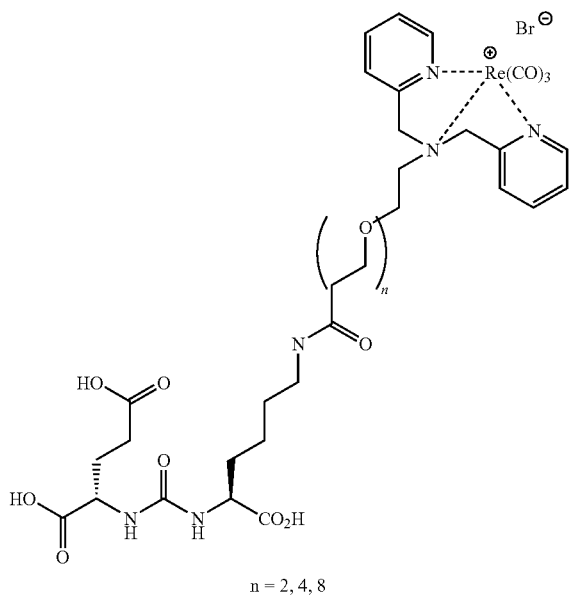

n = 2, 4, 8

Example 5a (n=2)

Glu-urea-Lys-PEG2-ReDP: [Re(CO)$_3${(17R,21S)-11,19-dioxo-1-(pyridin-2-yl)-2-(pyridin-2-ylmethyl)-5,8-dioxa-2,12,18,20-tetraazatricosane-17,21,23-tricarboxylic acid}][Br]. (17R,21S)-11,19-dioxo-1-(pyridin-2-yl)-2-(pyridin-2-ylmethyl)-5,8-dioxa-2,12,18,20-tetraazatricosane-17,21,23-tricarboxylic acid was prepared employing the same general procedure as described in Scheme 1, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product (2 mg, 20%) as an off-white solid. $^1$H NMR (400 MHz, DMSO-$d_6$) δ 8.8 (d), 8.00 (dd), 7.55 (d), 7.42 (dd), 6.45 (s), 3.95 (m), 3.4-3.6 (m), 2.45 (m), 1.25 (m), 1.1 (m), 0.8 (m). ESMS m/z: 931 (M+H)$^+$.

Example 5b (n=4)

Glu-urea-Lys-PEG4-ReDP: [Re(CO)$_3${(23R,27S)-17,25-dioxo-1-(pyridin-2-yl)-2-(pyridin-2-ylmethyl)-5,8,11,14-tetraoxa-2,18,24,26-tetraazanonacosane-23,27,29-tricarboxylic acid}][Br]. (23R,27S)-17,25-dioxo-1-(pyridin-2-yl)-2-(pyridin-2-ylmethyl)-5,8,11,14-tetraoxa-2,18,24,26-tetraazanonacosane-23,27,29-tricarboxylic acid was prepared employing the same general procedure that for Example 6a, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product. (5.1 mg, 29.6%) as a white solid. ESMS m/z: 1019 (M+H)$^+$.

Example 5c (n=8)

Glu-urea-Lys-PEG8-ReDP: [Re(CO)$_3${(35R,39S)-29,37-dioxo-1-(pyridin-2-yl)-2-(pyridin-2-ylmethyl)-5,8,11,14,17,20,23,26-octaoxa-2,30,36,38-tetraazahentetracontane-35,39,41-tricarboxylic acid}][Br]. The PEG8 dipyridyl compound, (35R,39 S)-29,37-dioxo-1-(pyridin-2-yl)-2-(pyridin-2-ylmethyl)-5,8,11,14,17,20,23,26-octaoxa-2,30,36,38-tetraazahentetracontane-35,39,41-tricarboxylic acid was prepared employing the same general procedure as for Example 6a, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product (8.0 mg, 30.4%) as a white solid. ESMS m/z: 1195 (M+H)$^+$.

Example 6

[Re(CO)₃][(19S,23S)-2-((1-(carboxymethyl)-1H-imidazol-2-yl)methyl)-13,21-dioxo-2,14,20,22-tetraazapentacosane-1,19,23,25-tetracarboxylic acid]

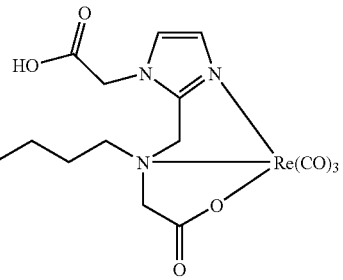

Step 1. 11-((2-tert-butoxy-2-oxoethyl)((1-(2-tert-butoxy-2-oxoethyl)-1H-imidazol-2-yl)-methyl)amino)undecanoic acid

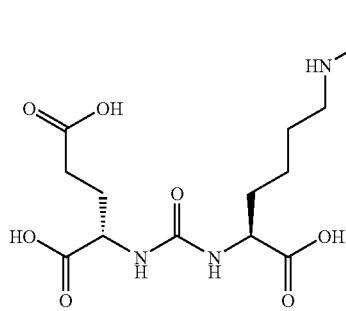

A suspension of 11-aminoundecanoic acid (603 mg, 3.0 mmol), 2-pyridinecarboxaldehyde (630 mg, 3.0 mmol) and AcOH (0.20 mL) in DCE (20 mL) was refluxed for 30 min under nitrogen. The reaction mixture was cooled to 0° C., and treated sequentially with NaBH(OAc)₃ (1.908 g, 9.0 mmol) and crude tert-butyl glyoxalate (1.50 g, 11.5 mmol). The reaction mixture was stirred at room temperature for overnight and decomposed with water. The reaction mixture was extracted with DCM. The organic layer was dried and concentrated under reduced pressure. The residue was purified by biotage over silica gel column to afford 11-((2-tert-butoxy-2-oxoethyl)((1-(2-tert-butoxy-2-oxoethyl)-1H-imidazol-2-yl)methyl)amino)undecanoic acid (343 mg, 22%) as a yellow oil. ¹H NMR (400 MHz, CDCl₃) 7.01 (d, J=1.2 Hz, 0.46H), 6.99 (d, J=1.2 Hz, 0.54H), 6.88 (d, J=1.2 Hz, 0.54H), 6.86 (d, J=1.2 Hz, 0.46H), 5.30 (s, 1.08 H), 5.07 (s, 0.92 H), 4.67 (s, 2 H), 4.66 (s, 2 H), 3.83 (s, 0.92 H), 3.17 (s, 1.08 H), 2.41-2.32 (m, 2 H), 1.66-1.63 (m, 2 H), 1.47 (s, 9 H), 1.45 (s, 9 H), 1.42-1.10 (m, 14 H); MS (ESI), 510 (M+H)⁺.

Step 2. (19S,23S)-tetra-tert-butyl 2-((1-(2-tert-butoxy-2-oxoethyl)-1H-imidazol-2-yl)-methyl)-13,21-dioxo-2,14,20,22-tetraazapentacosane-1,19,23,25-tetracarboxylate

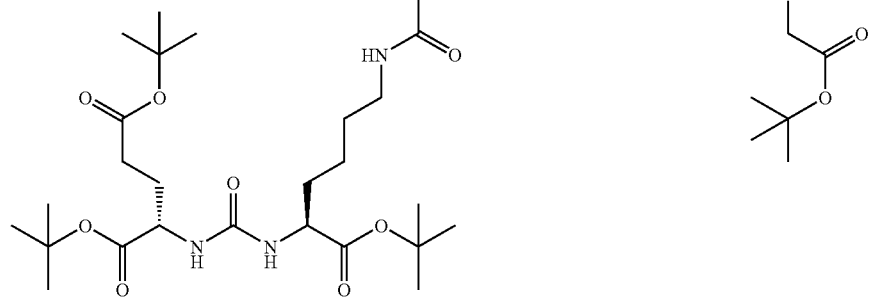

A solution of (S)-di-tert-butyl 2-(3-((S)-6-amino-1-tert-butoxy-1-oxohexan-2-yl)ureido)pentanedioate (85 mg, 0.175 mmol), 11-((2-tert-butoxy-2-oxoethyl)((1-(2-tert-butoxy-2-oxoethyl)-1H-imidazol-2-yl)methyl)amino)undecanoic acid (89 mg, 0.175 mmol), EDCI (1-ethyl-3-(3-dimethylaminopropyl)carbodiimide) (38 mg, 0.20 mmol), HOBt (1-Hydroxybenzotriazole) (26 mg, 0.20) and DIPEA (0.30 mL) in DCM (5.0 mL) was stirred at rt for 3 days. The reaction mixture was purified by biotage eluting with 1% to 10% MeOH in DCM to afford (19S,23S)-tetra-tert-butyl 2-((1-(2-tert-butoxy-2-oxoethyl)-1H-imidazol-2-yl)methyl)-13,21-dioxo-2,14,20,22-tetraazapentacosane-1,19,23,25-tetracarboxylate (111 mg, 65%) as a yellow oil. MS (ESI), 490.5 (M/2+H)$^+$.

Step 3. [Re(CO)$_3$][(19S,23S)-2-((1-(carboxymethyl)-1H-imidazol-2-yl)methyl)-13,21-dioxo-2,14,20,22-tetraazapentacosane-1,19,23,25-tetracarboxylic acid] (221)

A solution of (19 S,23S)-tetra-tert-butyl 2-((1-(2-tert-butoxy-2-oxoethyl)-1H-imidazol-2-yl)methyl)-13,21-dioxo-2,14,20,22-tetraazapentacosane-1,19,23,25-tetracarboxylate (18.8 mg, 0.019 mmol) in TFA (1.0 mL)/DCM (1.0 mL) was stirred at room temperature for overnight. The solvent was evaporated to give 19S,23S)-2-((1-(carboxymethyl)-1H-imidazol-2-yl)methyl)-13,21-dioxo-2,14,20,22-tetraazapentacosane-1,19,23,25-tetracarboxylic acid as a colorless oil. To a solution of the above deprotected product in water (1.0 mL) that was adjusted to pH=9 by 2 N NaOH was added Re(CO)$_3$(H2O)OTf (0.50 mL, 0.10 mL/mmol). The reaction mixtures were stirred at room temperature for overnight and purified by HPLC to afford the title compound (4.0 mg, 19%) as a white solid. $^1$H NMR (400 MHz, DMSO-d$_6$) 7.70 (t, J=5.6 Hz, 1H), 7.33 (s, 1 H), 7.13 (s, 2 H), 6.29 (d, J=8.4 Hz, 1 H), 6.26 (d, J=8.4 Hz, 1H), 4.96 (d, J=4.8 Hz, 2 H), 4.56 (d, J=16.4 Hz, 1 H), 4.12 (d, J=16.8 Hz, 1 H), 4.07-3.90 (m, 2 H), 3.70 (d, J=17.2 Hz, 1 H), 3.40 (d, J=17.2 Hz, 1 H), 2.98-2.94 (m, 4 H), 2.21 (q, J=7.73, 2 H), 1.99 (t, J=7.6 Hz, 2 H), 1.70-1.22 (m, 24 H); MS (ESI), 485.2 (M/2+H)$^+$.

Example 7

[Re(CO)$_3$][(7S,14S,18S)-7-amino-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid]

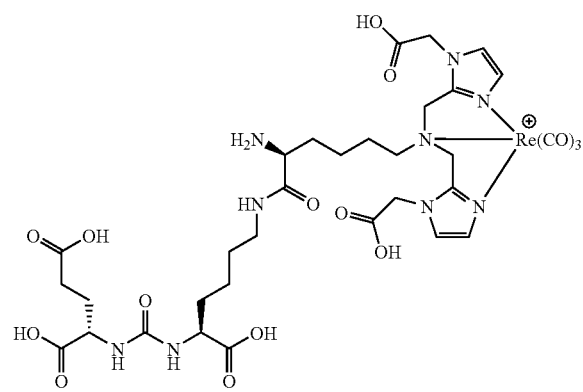

Step 1. (5S,12S,16S)-tri-tert-butyl 5-(4-(bis((1-(2-tert-butoxy-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate

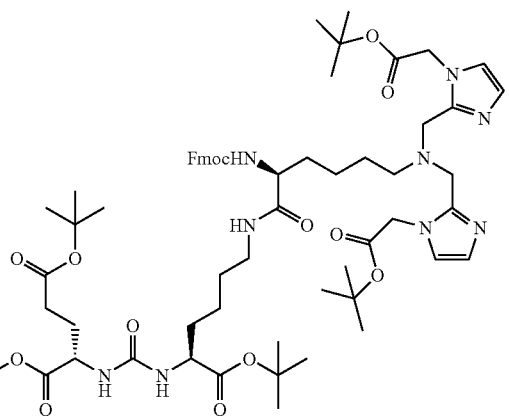

A solution of (S)-di-tert-butyl 2-(3-((S)-6-amino-1-tert-butoxy-1-oxohexan-2-yl)ureido)pentanedioate (97 mg, 0.20 mmol), Compound 2 (151 mg, 0.20 mmol), EDCI (38 mg, 0.20 mmol), HOBt (26 mg, 0.20) and DIPEA (0.30 mL) in DCM (5.0 mL) was stirred at rt for overnight. The reaction mixture was purified by biotage eluting with 1% to 10% MeOH in DCM to afford (5S,12S,16S)-tri-tert-butyl 5-(4-(bis((1-(2-tert-butoxy-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate (85.7 mg, 35%) as a white solid. $^1$H NMR (400 MHz, CDCl$_3$) 7.75 (d, J=7.6 Hz, 2 H), 7.64 (d, J=7.6 Hz, 2 H), 7.38 (t, J=7.4 Hz, 2 H), 7.29 (dd, J=7.6, 4.4 Hz, 2 H), 7.02 (brs, 1 H), 6.93 (s, 2 H), 6.80 (s, 2 H), 6.08 (d, J=8.0 Hz, 1 H), 5.75 (d, J=8.8 Hz, 1 H), 5.67 (d, J=7.6 Hz, 1 H), 4.58 (s, 2 H), 4.56 (s, 2 H), 4.55-4.52 (m, 1 H), 4.36-4.29 (m, 3 H), 4.21 (d, J=7.0 Hz, 1 H), 4.13 (t, J=6.8 Hz, 1 H), 3.63 (s, 4 H), 3.48-3.46 (m, 1 H), 3.05-3.01 (m, 1 H), 2.53 (t, J=7.2 Hz, 2 H), 2.33-2.26 (m, 2 H), 2.07-2.00 (m, 2 H), 1.77-1.26 (m, 55 H); MS (ESI), 614.0 (M/2+H)$^+$.

Step 2. (7S,14S,18S)-tri-tert-butyl 7-amino-1-(1-(2-tert-butoxy-2-oxoethyl)-1H-imidazol-2-yl)-2-((1-(2-tert-butoxy-2-oxoethyl)-1H-imidazol-2-yl)methyl)-8,16-dioxo-2,9,15,17-tetraazaicosane-14,18,20-tricarboxylate

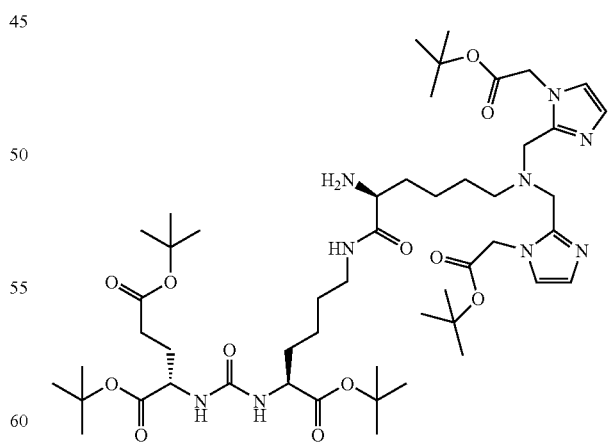

To a solution of (5S,12S,16S)-tri-tert-butyl 5-(4-(bis((1-(2-tert-butoxy-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate (84 mg, 0.069 mmol) in DMF (0.50 mL) was added piperidine (0.50 mL). The mixture was stirred at room temperature for 2 hrs. Solvent was evaporated under reduce pressure to afford a residue, which was purified by biotage eluting with 5% MeOH to 25% MeOH in DCM to afford (7S,14S,18S)-tri-tert-butyl 7-amino-1-(1-(2-tert-butoxy-2-oxoethyl)-1H-imidazol-2-yl)-2-((1-(2-tert-butoxy-2-oxoethyl)-1H-imidazol-2-yl)methyl)-8,16-dioxo-2,9,15,17-tetraazaicosane-14,18,20-tricarboxylate (59 mg, 86%). $^1$H NMR (400 MHz, CDCl$_3$) 6.96 (d, J=0.8 Hz, 2 H), 6.85 (d, J=0.8 Hz, 2 H), 5.55 (brs, 1 H), 5.43 (brs, 1 H), 4.59 (s, 4 H), 4.37-4.28 (m, 2 H), 3.61 (s, 4 H), 3.35-3.27 (m, 2 H), 3.18-3.12 (m, 1 H), 2.53 (t, J=7.4 Hz, 2 H), 2.34-2.28 (m, 2 H), 2.10-2.00 (m, 2 H), 1.85-1.26 (m, 55H); MS (ESI), 503.0 (M/2+H)$^+$.

Step 3. [Re(CO)$_3$][(7S,14S,18S)-7-amino-1-(1-(carboxymethyl)-1H-imidazol-2-yl)-2-((1-(carboxymethyl)-1H-imidazol-2-yl)methyl)-8,16-dioxo -2,9,15,17-tetraazaicosane-14,18,20-tricarboxylic acid]

A solution of (7S,14S,18S)-tri-tert-butyl 7-amino-1-(1-(2-tert-butoxy-2-oxoethyl)-1H-imidazol-2-yl)-2-((1-(2-tert-butoxy-2-oxoethyl)-1H-imidazol-2-yl)methyl)-8,16-dioxo-2, 9,15,17-tetraazaicosane-14,18,20-tricarboxylate (42 mg, 0.042 mmol) and [NEt$_4$]$_2$[Re(CO)$_3$Br$_3$] (42 mg, 0.055 mmol) in MeOH (5 mL) at a pressure tube was stirred at 90° C. for 4 hrs. The solvent was evaporated to give a residue, which was directly used for next step. A solution of the above product in TFA (3.0 mL)/DCM (3.0 mL) was stirred at room temperature for overnight. The solvent was evaporated to give a crude product, which was purified by HPLC to give the tile compound (27.9 mg, 67% over 2 steps) as a white solid. $^1$H NMR (400 MHz, DMSO-d$_6$) 8.42 (brs, 1 H), 8.10 (brs, 2 H), 7.18 (s, 2 H), 7.04 (s, 2 H), 6.32 (d, J=8.4 Hz, 1 H), 6.29 (d, J=8.0 Hz, 1 H), 4.02 (s, 4 H), 4.56-4.37 (m, 4 H), 4.08-4.01 (m, 2 H), 3.68-3.61 (m, 3 H), 3.11-3.08 (m, 2 H), 2.23-1.29 (m, 16 H); MS (ESI), 497.7 (M/2+H)$^+$.

Example 8

[Re(CO)$_3$][(19S,23S)-1-(1-(2-(bis(carboxymethyl) amino)-2-oxoethyl)-1H-imidazol-2-yl)-2-((1-(2-(bis (carboxymethyl)amino)-2-oxoethyl)-1H-imidazol-2-yl)methyl)-13,21-dioxo-2,14,20,22-tetraazapentacosane-19,23,25-tricarboxylic acid]

Step 1. tert-butyl 2,2'-(2-bromoacetylazanediyl)diacetate

To a solution of tert-butyl 2,2'-azanediyldiacetate (3.00 g, 12.24 mmol) and 2-bromoacetyl bromide (1.39 mL, 3.23 g, 16.00 mmol) in DCM (100 mL) was added Et$_3$N (2.0 mL) at room temperature. The reaction mixtures were stirred at room temperature for 2 hrs. The reaction mixtures were diluted with DCM (300 mL), washed with water, and dried over Na$_2$SO$_4$. Solvent was evaporated under reduce pressure to afford a residue, which was purified by biotage eluting with 10% hexanes in EtOAc to 50% hexanes in EtOAc to tert-butyl 2,2'-(2-bromoacetylazanediyl)diacetate (4.68 g, 100%). $^1$H NMR (400 MHz, CDCl$_3$) 4.09 (s, 2 H), 4.07 (s, 2 H), 3.86 (s, 2 H), 1.49 (s, 9 H), 1.46 (s, 9 H); MS (ESI), 388, 390 (M+Na)$^+$.

Step 2. tert-butyl 2,2'-(2-(2-formyl-1H-imidazol-1-yl) acetylazanediyl)diacetate

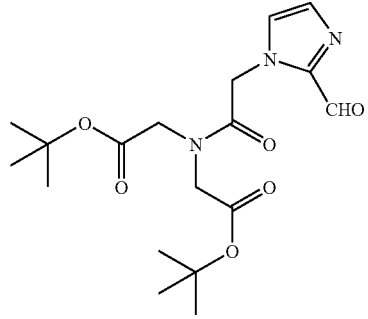

A solution of tert-butyl 2,2'-(2-bromoacetylazanediyl)diacetate (4.55 g, 12.43 mmol), 1H-imidazole-2-carbaldehyde (1.536 g, 16.0 mmol), DIPEA (5.0 mL), and KI (0.64 g, 4.0 mmol) was stirred at 80° C. for overnight. After the solvent was evaporated under reduced pressure, the reaction mixture was diluted with DCM, washed with water and dried. Solvent was evaporated under reduce pressure to afford a residue, which was purified by biotage eluting with DCM to 3% MeOH in DCM to tert-butyl 2,2'-(2-(2-formyl-1H-imidazol-1-yl)acetylazanediyl)diacetate (3.96 g, 84%). $^1$H NMR (400 MHz, CDCl$_3$) 9.76 (s, 1 H), 7.31 (s, 1 H), 7.25 (s, 1 H), 5.30

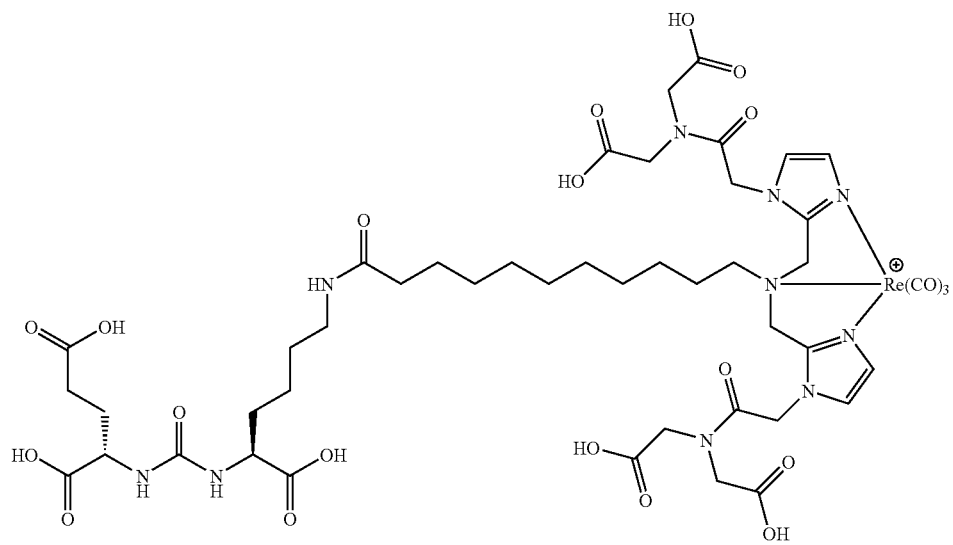

(s, 2 H), 4.14 (s, 2 H), 4.07 (s, 2 H), 1.51 (s, 9 H), 1.43 (s, 9 H); MS (ESI), 382 (M+H)+.

Step 3. 11-(bis((1-(2-(bis(2-tert-butoxy-2-oxoethyl)amino)-2-oxoethyl)-1H-imidazol-2-yl)methyl)amino)undecanoic acid dazol-2-yl)methyl)amino)undecanoic acid (368 mg, 79%). $^1$H NMR (400 MHz, DMSO-$d_6$) 6.93 (s, 2 H), 6.76 (s, 2 H), 5.02 (s, 4 H), 4.29 (s, 4 H), 3.93 (s, 4 H), 3.44 (s, 4 H), 2.30 (t, J=7.6 Hz, 2 H), 2.09 (t, J=7.6 Hz, 2 H), 1.43 (s, 18 H), 1.35 (s, 18 H), 1.29-1.00 (m, 16 H); MS (ESI), 466.9 (M/2+H)+.

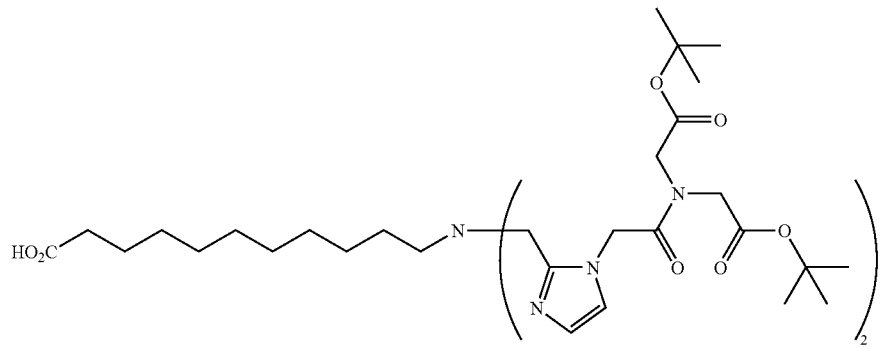

Step 4. (19S,23S)-tri-tert-butyl 1-(1-(2-(bis(2-tert-butoxy-2-oxoethyl)amino)-2-oxoethyl)-1H-imidazol-2-yl)-2-((1-(2-(bis(2-tert-butoxy -2-oxoethyl)amino)-2-oxoethyl)-1H-imidazol-2-yl)methyl)-13,21-dioxo-2,14,20,22-tetraazapentacosane-19,23,25-tricarboxylate

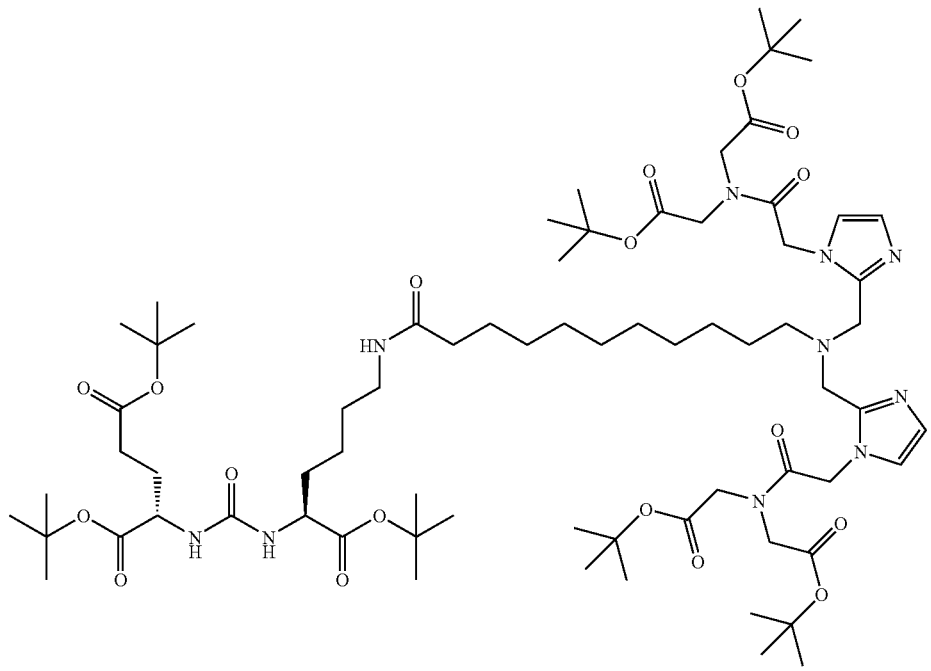

A solution of 11-aminoundecanoic acid (100 mg, 0.50 mmol), tert-butyl 2,2'-(2-(2-formyl-1H-imidazol-1-yl)acetylazanediyl)diacetate (381 mg, 1.0 mmol) and AcOH (0.02 mL) in DCE (30 mL) was stirred at 75° C. for 30 min under nitrogen. The reaction mixture was cooled to 0° C., and treated with NaBH(OAc)$_3$ (0.3165 g, 1.5 mmol). The reaction mixture was stirred at room temperature for overnight and decomposed with water. Solvent was evaporated under reduce pressure to afford a residue, which was purified by biotage eluting with 1-10% MeOH in DCM 11-(bis((1-(2-(bis(2-tert-butoxy-2-oxoethyl)amino)-2-oxoethyl)-1H-imi- A solution of (S)-di-tert-butyl 2-(3-((S)-6-amino-1-tert-butoxy-1-oxohexan-2-yl)ureido)pentanedioate (85 mg, 0.174 mmol), 11-(bis((1-(2-(bis(2-tert-butoxy-2-oxoethyl)amino)-2-oxoethyl)-1H-imidazol-2-yl)methyl)amino)undecanoic acid (118 mg, 0.127 mmol), EDCI (38 mg, 0.20 mmol), HOBt (26 mg, 0.20) and DIPEA (0.30 mL) in DCM (5.0 mL) was stirred at rt for overnight. The reaction mixture was purified by biotage eluting with 1% to 10% MeOH in DCM to afford (19S,23S)-tri-tert -butyl 1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-

1H-imidazol-2-yl)methyl)-13,21-dioxo-2,14,20,22-tetraazapentacosane-19,23,25-tricarboxylate (38 mg, 21%) as a colorless oil. ¹H NMR (400 MHz, CDCl₃) 6.95 (d, J=1.2 Hz, 2 H), 6.83 (d, J=0.80 Hz, 2H), 5.97 (s, 1 H), 5.28 (d, J=7.6 Hz, 1 H), 5.23 (d, J=8.4 Hz, 1 H), 4.94 (s, 4 H), 4.33-4.25 (m, 2H), 4.12 (s, 4 H), 4.03 (s, 4 H), 3.63 (s, 4 H), 3.25-3.16 (m, 2 H), 2.53 (t, J=7.4 Hz, 2 H), 2.33-2.24 (m, 2 H), 2.15 (t, J=7.6 Hz, 2 H), 2.08-2.03 (m, 2 H), 2.02-1.20 (m, 85 H); MS (ESI), 701.6 (M/2+H)⁺.

Step 5. [Re(CO)₃][(19S,23S)-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-13,21-dioxo-2,14,20,22-tetraazapentacosane-19,23,25-tricarboxylic acid] (223)

A solution of (19S,23S)-tri-tert-butyl 1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-13,21-dioxo-2,14,20,22-tetraazapentacosane-19,23,25-tricarboxylate (28 mg, 0.02 mmol) and [NEt₄]₂[Re(CO)₃Br₃] (30 mg, 0.039 mmol) in MeOH (5 mL) at a pressure tube was stirred at 90° C. for overnight. The solvent was evaporated to give a residue, which was directly used for next step. A solution of the above product in TFA (3.0 mL)/DCM (3.0 mL) was stirred at room temperature for 3 hrs. The solvent was evaporated to give a crude product, which was purified by HPLC to give the title compound (17.6 mg, 69% over 2 steps) as a white solid. ¹H NMR (400 MHz, DMSO-d₆) 7.70 (t, J=4.8 Hz, 1 H), 7.10 (s, 2 H), 7.03 (s, 2 H), 6.29 (d, J=8.4 Hz, 1H), 6.26 (d, J=8.4 Hz, 1 H), 5.02 (s, 4 H), 4.37-3.97 (m, 14 H), 3.60-3.57 (m, 2 H), 3.01-2.94 (m, 2 H), 2.24-1.22 (m, 28 H); MS (ESI), 640.3 (M/2+H)⁺.

Example 9

[Re(CO)₃][(7S,14S,18S)-7-amino-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-8,16-dioxo-2,9,15,17-tetraazaicosane-14,18,20-tricarboxylic acid]

Step 1. 2-(((9H-fluoren-9-yl)methoxy)carbonylamino)-6-(bis((1-(2-(bis(2-tert-butoxy-2-oxoethyl)amino)-2-oxoethyl)-1H-imidazol-2-yl)methyl)amino)hexanoic acid

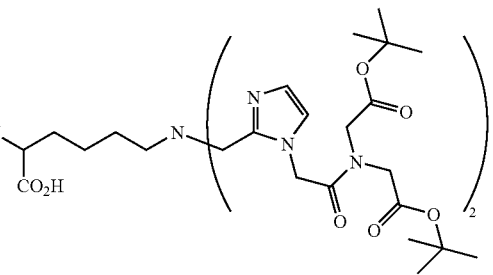

To a suspension of L-Fmoc-Lysine-OH (0.202 g, 0.50 mmol), tert-butyl 2,2'-(2-(2-formyl-1H-imidazol-1-yl)acetylazanediyl)diacetate (0.381 g, 1.00 mmol) in DCE (30 mL) was heated at 80° C. for 30 min. The reaction mixture was cooled to 0° C., and treated with NaBH(OAc)₃ (0.3165 g, 1.50 mmol). The reaction stirred at room temperature for 12 hours and decomposed with water. The reaction mixture was extracted with DCM. The organic layer was dried and concentrated under reduced pressure. The residue was purified by a Biotage SP4 with a gradient method of 5-25% methanol in DCM to afford 2-(((9H-fluoren-9-yl)methoxy)carbonylamino)-6-(bis((1-(2-(bis(2-tert-butoxy-2-oxoethyl)amino)-2-oxoethyl)-1H-imidazol-2-yl)methyl)amino)hexanoic acid as a white solid (0.408 g, 74% yield). ¹H NMR (400 MHz, CDCl₃) 7.74 (d, J=7.6 Hz, 2 H), 7.67 (t, J=6.0 Hz, 2 H), 7.38 (t, J=7.4 Hz, 2 H), 7.29 (d, J=7.6 Hz, 2 H), 6.92 (s, 2 H), 6.29 (s, 2 H), 6.19 (brs, 1 H), 5.09-5.04 (m, 2 H), 4.81-4.79 (m, 1 H), 4.39-4.30 (m, 4 H), 4.23 (t, J=7.2 Hz, 1 H), 4.22-3.58 (m, 10 H), 3.48 (s, 2 H), 2.34-2.30 (m, 2 H), 1.67-1.26 (m, 6H), 1.50 (s, 18 H), 1.42 (s, 18 H). ESMS m/z: 550.5 (M/2+H)⁺.

Step 2. (7S,14S,18S)-tri-tert-butyl 7-amino-1-(1-(2-(bis(2-tert-butoxy-2-oxoethyl)amino)-2-oxoethyl)-1H-imidazol-2-yl)-2-((1-(2-(bis(2-tert-butoxy -2-oxoethyl)amino)-2-oxoethyl)-1H-imidazol-2-yl)methyl)-8,16-dioxo-2,9,15,17-tetraazaicosane-14,18,20-tricarboxylate

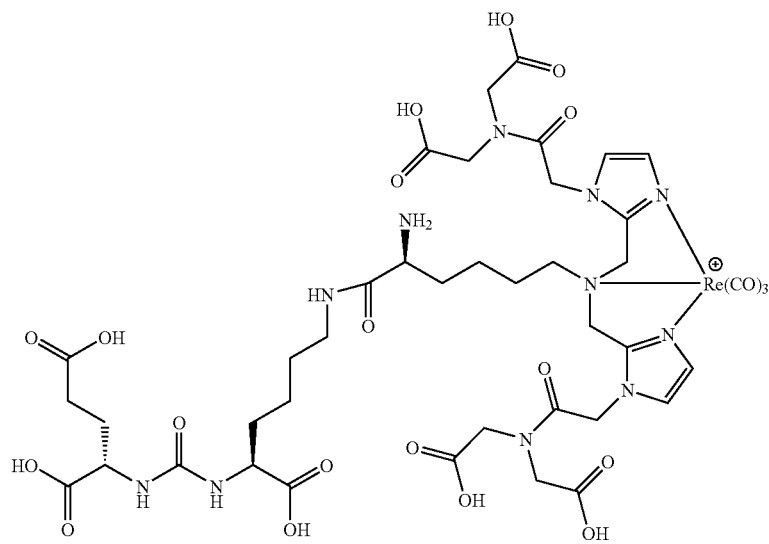

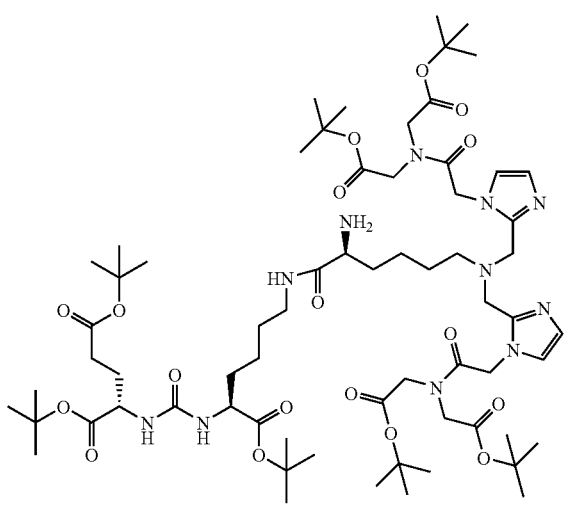

A solution of (S)-di-tert-butyl 2-(3-((S)-6-amino-1-tert-butoxy-1-oxohexan-2-yl)ureido)pentanedioate (97 mg, 0.20 mmol), 2-(((9H-fluoren-9-yl)methoxy)carbonylamino)-6-(bis((1-(2-(bis(2-tert-butoxy-2-oxoethyl)amino)-2-oxoethyl)-1H-imidazol-2-yl)methyl)amino)hexanoic acid (132 mg, 0.12 mmol), EDCI (38 mg, 0.20 mmol), HOBt (26 mg, 0.20) and DIPEA (0.30 mL) in DCM (5.0 mL) was stirred at rt for 2 days. The reaction mixture was purified by biotage eluting with 1% MeOH in DCM to afford (5S,12S,16S)-tri-tert-butyl 5-(4-(bis((1-(2-(bis(2-tert-butoxy-2-oxoethyl)amino)-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate (impure) as an oil.

To a solution of the above product, (5S,12S,16S)-tri-tert-butyl 5-(4-(bis((1-(2-(bis(2-tert-butoxy-2-oxoethyl)amino)-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate in DMF (1.0 mL) was added piperidine (0.50 mL). The mixture was stirred at room temperature for 2 hrs. Solvent was evaporated under reduce pressure to afford a residue, which was purified by biotage eluting with 5% MeOH to 50% MeOH in DCM to afford (7S,14S,18S)-tri-tert-butyl 7-amino-1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-8,16-dioxo-2,9,15,17-tetraazaicosane-14,18,20-tricarboxylate (40 mg, 25%) as a white solid. $^1$H NMR (400 MHz, CDCl$_3$) 6.96 (s, 2 H), 6.83 (d, 2 H), 6.37 (brs, 1 H), 6.33 (brs, 1 H), 5.05 (s, 4 H), 4.87 (brs, 2 H), 4.27-4.24 (m, 2 H), 4.18 (s, 4 H), 4.10 (s, 4 H), 3.88 (d, J=15.2 Hz, 2 H), 3.62 (d, J=15.2 Hz, 2 H), 3.14-3.12 (m, 1 H), 2.30-1.24 (m, 83 H); MS (ESI), 674.1 (M/2+H)$^+$.

Step 3. [Re(CO)$_3$][(7S,14S,18S)-7-amino-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-8,16-dioxo-2,9,15,17-tetraazaicosane-14,18,20-tricarboxylic acid] (224)

A solution of (7S,14S,18S)-tri-tert-butyl 7-amino-1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-8,16-dioxo-2,9,15,17-tetraazaicosane-14,18,20-tricarboxylate (19 mg, 0.014 mmol) and [NEt$_4$]$_2$[Re(CO)$_3$Br$_3$] (19 mg, 0.024 mmol) in MeOH (3 mL) at a pressure tube was stirred at 90° C. for 3 hrs. The solvent was evaporated to give a residue, which was directly used for next step. A solution of the above product in TFA (3.0 mL)/DCM (3.0 mL) was stirred at room temperature for overnight. The solvent was evaporated to give a crude product, which was purified by HPLC to give [Re(CO)$_3$][(7S,14S,18S)-7-amino-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-8,16-dioxo-2,9,15,17-tetraazaicosane-14,18,20-tricarboxylic acid] (14.1 mg, 82% over 2 steps) as a white solid. $^1$H NMR (400 MHz, DMSO-d$_6$) 8.43 (brs, 1 H), 8.09 (brs, 3 H), 7.10 (s, 2 H), 7.03 (s, 2 H), 6.51 (brs, 1 H), 6.31 (d, J=8.0 Hz, 1 H), 6.28 (d, J=8.4 Hz, 1 H), 5.00 (s, 4 H), 4.40-4.01 (m, 14 H), 3.70-3.64 (m, 3 H), 3.11-3.08 (m, 2 H), 2.26-1.29 (m, 16 H); MS (ESI), 612.8 (M+H)/2$^+$.

Example 10

Re(CO)$_3$][(7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid]

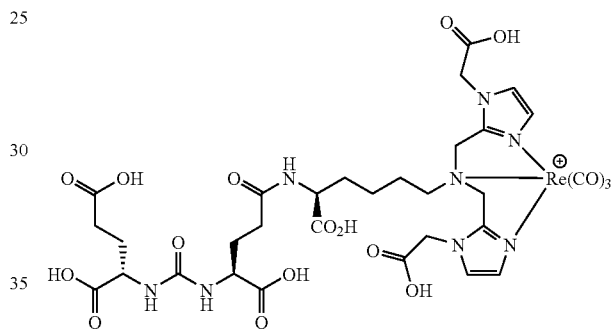

Step 1. (S)-di-tert-butyl 2-(3-((S)-1-tert-butoxy-5-(2,5-dioxopyrrolidin-1-yloxy)-1,5-dioxopentan-2-yl)ureido)pentanedioate

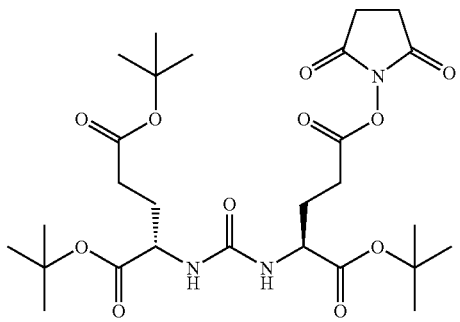

A solution of (S)-5-tert-butoxy-4-(3-((S)-1,5-di-tert-butoxy-1,5-dioxopentan-2-yl)ureido)-5-oxopentanoic acid (Kularatne, S. A.; et. al. *Mol. Pharmaceutics,* 2009, 6, 790-800) (164 mg, 0.336 mmol), N,N'-disuccinimidyl carbonate (128 mg, 0.50 mmol) and pyridine (0.10 mL) in CH$_3$CN (5.0 mL) was stirred at rt for overnight. Solvent was removed under reduced pressure to give a residue, which was purified by biotage eluting with 10% to 70% EtOAc in hexanes to afford (S)-di-tert-butyl 2-(3-((S)-1-tert-butoxy-5-(2,5-dioxopyrrolidin-1-yloxy)-1,5-dioxopentan-2-yl)ureido)pentanedioate (190 mg, 97%) as a white solid.

Step 2. (2S,7S,11S)-2-(4-(bis((1-(2-tert -butoxy-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid

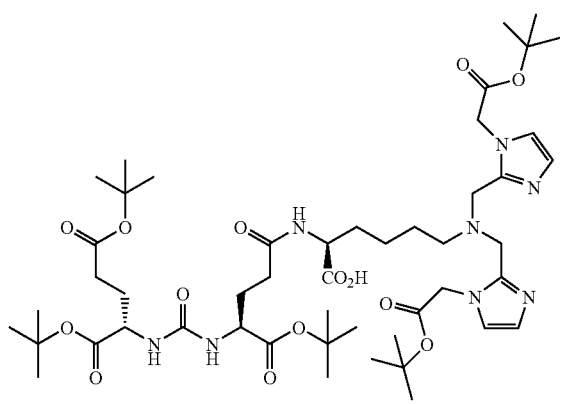

A solution of (S)-di-tert-butyl 2-(3-((S)-1-tert-butoxy-5-(2,5-dioxopyrrolidin-1-yloxy)-1,5-dioxopentan-2-yl)ureido)pentanedioate (138 mg, 0.236 mmol), (S)-2-amino-6-(bis((1-(2-tert-butoxy-2-oxoethyl)-1H-imidazol-2-yl)methyl)amino)hexanoic acid (127 mg, 0.237 mmol) and DIPEA (0.50 mL) in DMF (1.0 mL) was stirred at rt for overnight. The Solvent was removed under reduced pressure to give a residue, which was purified by biotage eluting with 1% to 50% MeOH in DCM to afford (2S,7S,11S)-2-(4-(bis((1-(2-tert-butoxy-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid (203 mg, 86%) as a white solid. $^1$H NMR (400 MHz, CDCl$_3$) 7.40 (brs, 1 H), 6.99 (s, 2 H), 6.79 (s, 2 H), 6.12 (brs, 1 H), 5.62 (brs, 1 H), 4.67-4.28 (m, 7 H), 3.68 (d, J=14.0 Hz, 2 H), 3.62 (d, J=14.0 Hz, 2 H), 2.62-2.53 (m, 2H), 2.34-2.02 (m, 8 H), 1.83-1.42 (m, 51 H); MS (ESI), 503.5 (M/2+H)$^+$.

Step 3. [Re(CO)$_3$][(7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid] (225)

A solution of ((2S,7S,11S)-2-(4-(bis((1-(2-tert-butoxy-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid (45 mg, 0.0448 mmol) and [NEt$_4$]$_2$[Re(CO)$_3$Br$_3$] (45 mg, 0.058 mmol) in MeOH (5 mL) at a pressure tube was stirred at 90° C. for 4 hrs. The solvent was evaporated to give a residue, which was directly used for next step. A solution of the above product in TFA (2.0 mL)/DCM (3.0 mL) was stirred at room temperature for overnight. The solvent was evaporated to give a crude product, which was purified by HPLC to give [Re(CO)$_3$][(7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid] (30 mg, 67% over 2 steps) as a white solid. $^1$H NMR (400 MHz, DMSO-d$_6$) 8.14 (d, J=7.2 Hz, 1 H), 7.19 (d, J=0.8 Hz, 2 H), 7.05 (d, J=1.2 Hz, 2 H), 6.37-6.34 (m, 2 H), 4.85 (s, 4 H), 4.58 (dd, J=16.4, 2.8 Hz, 2 H), 4.40 (dd, J=16.0, 2.8 Hz, 2 H), 4.22-4.04 (m, 3 H), 3.65 (t, J=7.6 Hz, 2 H), 2.25-1.32 (m, 16 H); MS (ESI), 995.3 M$^+$.

Example 11

[Re(CO)$_3$][(7S,12S,16S)-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-9,14-dioxo-2,8,13,15-tetraazaoctadecane-7,12,16,18-tetracarboxylic acid]

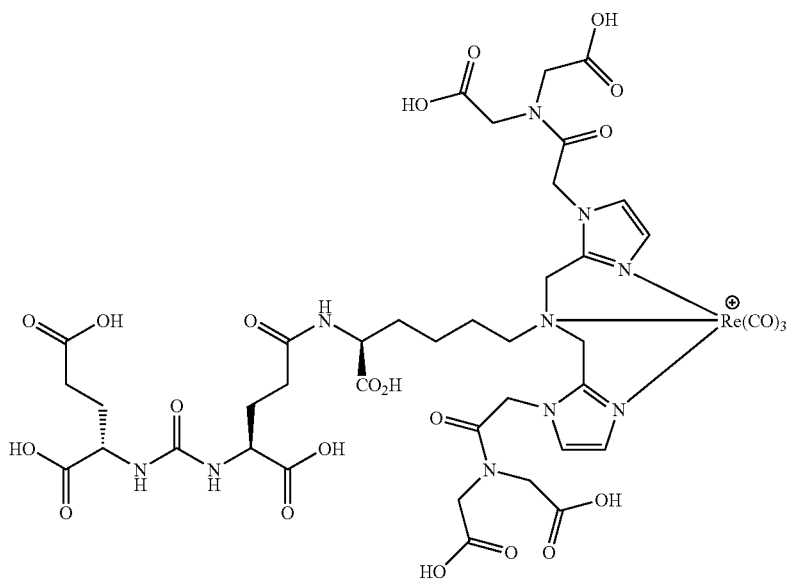

Step 1. (S)-2-amino-6-(bis((1-(2-(bis(2-tert-butoxy-2-oxoethyl)amino)-2-oxoethyl)-1H-imidazol-2-yl)methyl)amino)hexanoic acid

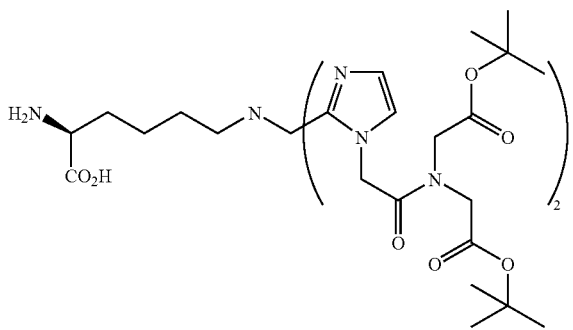

A solution of 2-(((9H-fluoren-9-yl)methoxy)carbonylamino)-6-(bis((1-(2-(bis(2-tert-butoxy-2-oxoethyl)amino)-2-oxoethyl)-1H-imidazol-2-yl)methyl)amino)hexanoic acid (190 mg, 0.173 mmol) and piperidine (0.50 mL) in DMF (0.50 mL) was stirred at room temperature for 1 hrs. The solvent was evaporated under reduced pressure to give a crude product. The crude product was purified by Biotage SP4 with a gradient method of 5-50% methanol in DCM to give (S)-2-amino-6-(bis((1-(2-(bis(2-tert-butoxy-2-oxoethyl)amino)-2-oxoethyl)-1H-imidazol-2-yl)methyl)amino)hexanoic acid (0.120 g, 79%). $^1$H NMR (400 MHz, DMSO-$d_6$). 6.92 (s, 2 H), 6.76 (s, 2 H), 5.01 (s, 4 H), 4.32 (s, 2 H), 4.31 (s, 2 H), 3.92 (s, 4 H), 3.44 (s, 4 H), 3.01-2.99 (m, 1 H), 2.30 (t, J=7.2 Hz, 2 H), 1.60-1.57 (m, 2 H), 1.43 (s, 18 H), 1.35 (m, 18 H). 1.30-1.12 (m, 4 H); MS (ESI), 439.4 (M/2+H)$^+$.

Step 2. (2S,7S,11S)-2-(4-(bis((1-(2-(bis(2-tert-butoxy-2-oxoethyl)amino)-2-oxoethyl)-1H-imidazol-2-yl)methyl)amino)butyl)-7,11-bis(tert -butoxycarbonyl)-16,16-dimethyl-4,9,14-trioxo-15-oxa-3,8,10-triazaheptadecan-1-oic acid A solution of (S)-di-tert-butyl 2-(3-((S)-1-tert-butoxy-5-(2,5-dioxopyrrolidin-1-yloxy)-1,5-dioxopentan-2-yl)ureido) pentanedioate (82 mg, 0.14 mmol), ((S)-2-amino-6-(bis((1-(2-(bis(2-tert-butoxy-2-oxoethyl)amino)-2-oxoethyl)-1H-imidazol-2-yl)methyl)amino)hexanoic acid (98 mg, 0.11 mmol) and DIPEA (0.50 mL) in DMF (2.0 mL) was stirred at rt for overnight. The Solvent was removed under reduced pressure to give a residue, which was purified by biotage eluting with 1% to 40% MeOH in DCM to afford (2S,7S,11S)-2-(4-(bis((1-(2-(bis(2-tert -butoxy-2-oxoethyl)amino)-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid (125 mg, 84%) as a white solid. MS (ESI), 674.6 (M/2+H)$^+$.

Step 3. [Re(CO)$_3$][(7S,12S,16S)-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-9,14-dioxo-2,8,13,15-tetraazaoctadecane-7,12,16,18-tetracarboxylic acid] (226)

A solution of (2S,7S,11S)-2-(4-(bis((1-(2-(bis(2-tert-butoxy-2-oxoethyl)amino)-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid (54 mg, 0.040 mmol) and [NEt$_4$]$_2$[Re(CO)$_3$Br$_3$] (47 mg, 0.060 mmol) in MeOH (5 mL) at a pressure tube was stirred at 90° C. for 4 hrs. The solvent was evaporated to give a residue, which was directly used for next step. A solution of the above product in TFA (2.0 mL)/DCM (3.0 mL) was stirred at room temperature for overnight. The solvent was evaporated to give a crude product, which was purified by HPLC to give the title compound (44.8 mg, 91% over 2 steps) as a white solid. $^1$H NMR (400 MHz, DMSO-$d_6$) 8.17 (d, J=7.6 Hz, 1 H), 7.11 (d, J=1.2 Hz, 2 H), 7.03 (d, J=1.2 Hz, 2 H), 6.37-6.33 (m, 2 H), 5.02 (s, 4 H), 4.40-3.98 (m, 15 H), 3.65 (t, J=7.6 Hz, 2 H), 2.25-1.32 (m, 14 H); MS (ESI), 613.3 (M+H)/2$^+$.

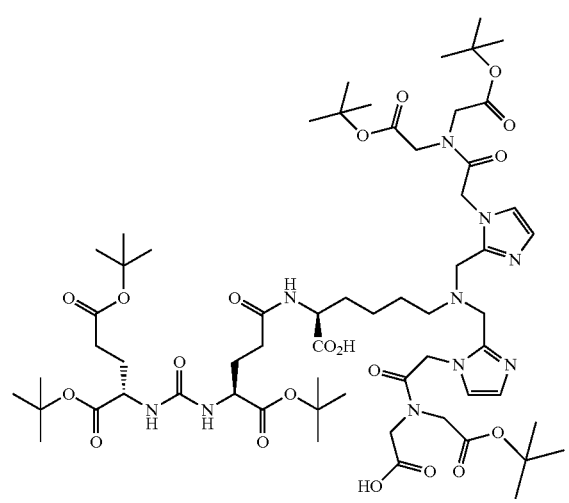

Additional compounds prepared by the above methods, with appropriate reagent selection include Examples 14-20, below.

Example 12
(7S,22S,26S)-9,16,24-trioxo-1-(quinolin-2-yl)-2-(quinolin-2-ylmethyl)-2,8,17,23,25-pentaazaoctacosane-7,22,26,28-tetracarboxylic acid
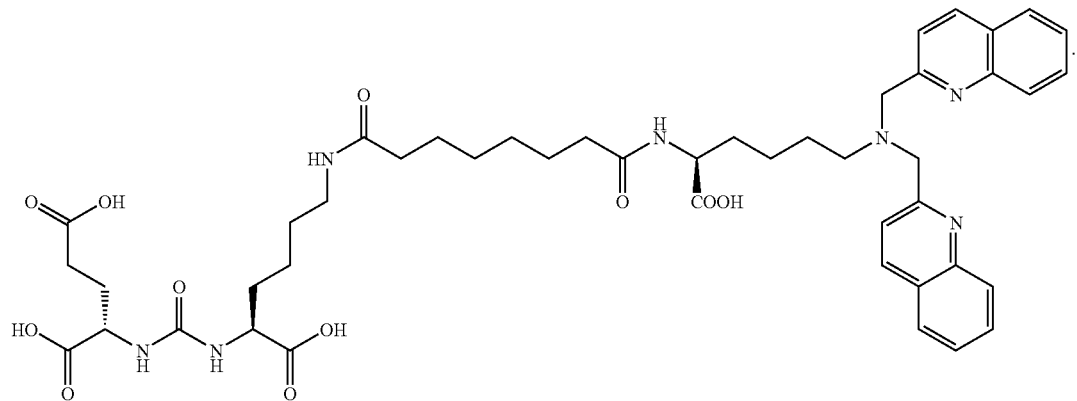
Example 13
(7S,22S,26S)-9,16,24-trioxo-1-(pyridin-2-yl)-2-(pyridin-2-ylmethyl)-2,8,17,23,25-pentaazaoctacosane-7,22,26,28-tetracarboxylic acid
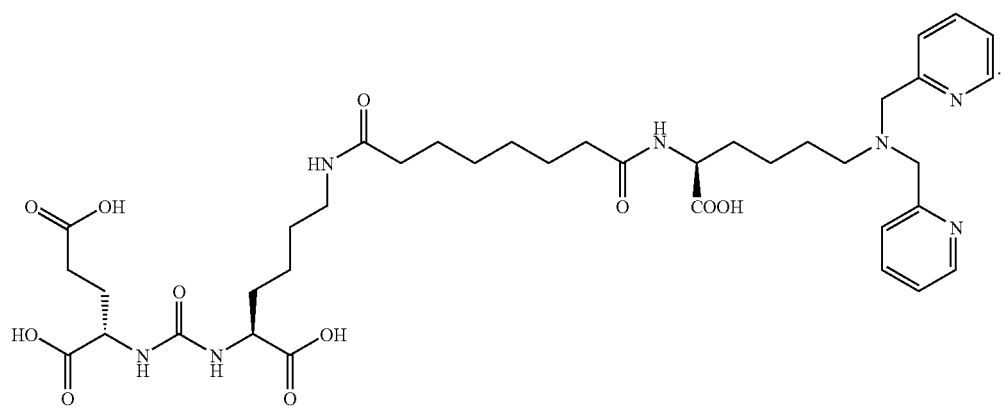

Example 14
(22S,26S)-9,16,24-trioxo-2-(pyridin-2-ylmethyl)-2,8,17,23,25-pentaazaoctacosane-1,7,22,26,28-pentacarboxylic acid
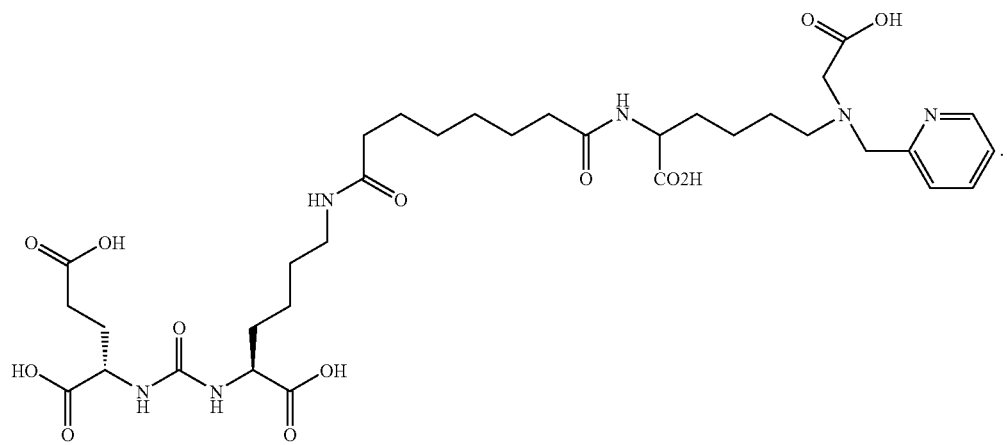
Example 15
(7S,22S,26S)-1-(1-(carboxymethyl)-1H-imidazol-2-yl)-2-((3-(carboxymethyl)-3H-pyrrol-2-yl)methyl)-9,16,24-trioxo-2,8,17,23,25-pentaazaoctacosane-7,22,26,28-tetracarboxylic acid
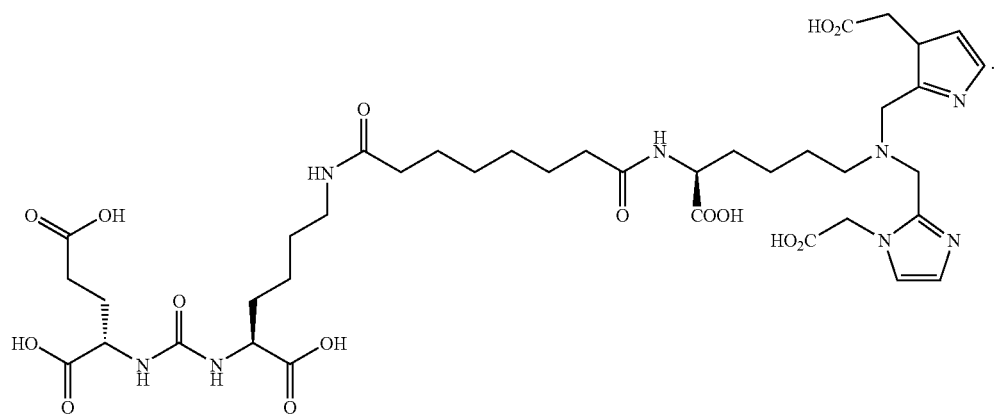

Example 16

(19S,23S)-1-(1-(carboxymethyl)-1H-imidazol-2-yl)-
2-((1-(carboxymethyl)-1H-imidazol-2-yl)methyl)-
13,21-dioxo-2,14,20,22-tetraazapentacosane-19,23,
25-tricarboxylic acid

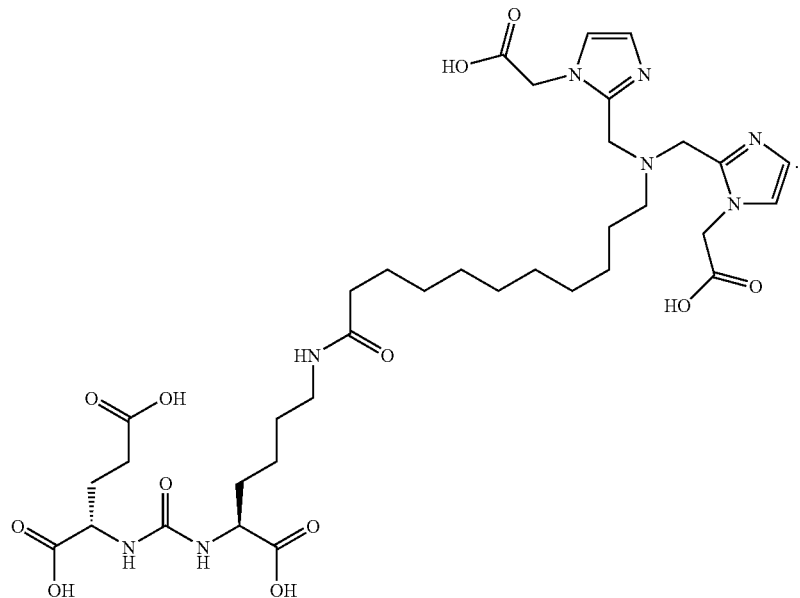

Example 17

(7S,11S,26S)-26-(4-(bis((1-methyl-1H-imidazol-2-
yl)methyl)amino)butyl)-7,11-bis(tert-butoxycarbo-
nyl)-2,2-dimethyl-4,9,17,24-tetraoxo-3-oxa-8,10,16,
25-tetraazaheptacosan-27-oic acid

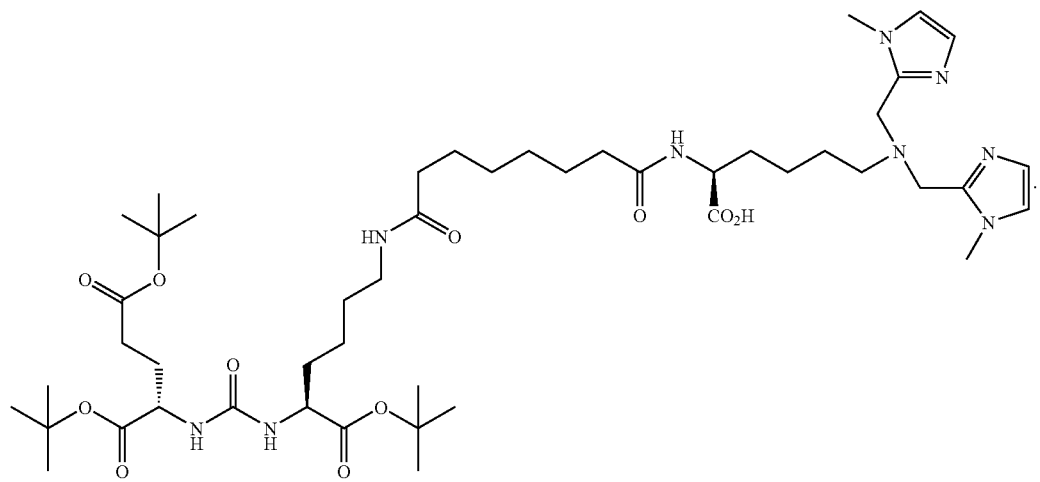

Other compounds may be prepared incorporating a chelator based upon 1,4,7,10-tetraazacyclododecane-1,4,7,10-tetraacetic acid (DOTA). Such DOTA-based chelators may be used for the cheation of a imaging metals including, but not limited to yttrium, lutetium, gallium, and indium. The DOTA-based chelators may be prepared as outlined above, exploiting one of the acid groups of DOTA to link to the other R-groups. Exemplary DOTA-based compounds include, but are not limited to, where M is Y, Lu, Ga, or In; and n is from 0 to 20:

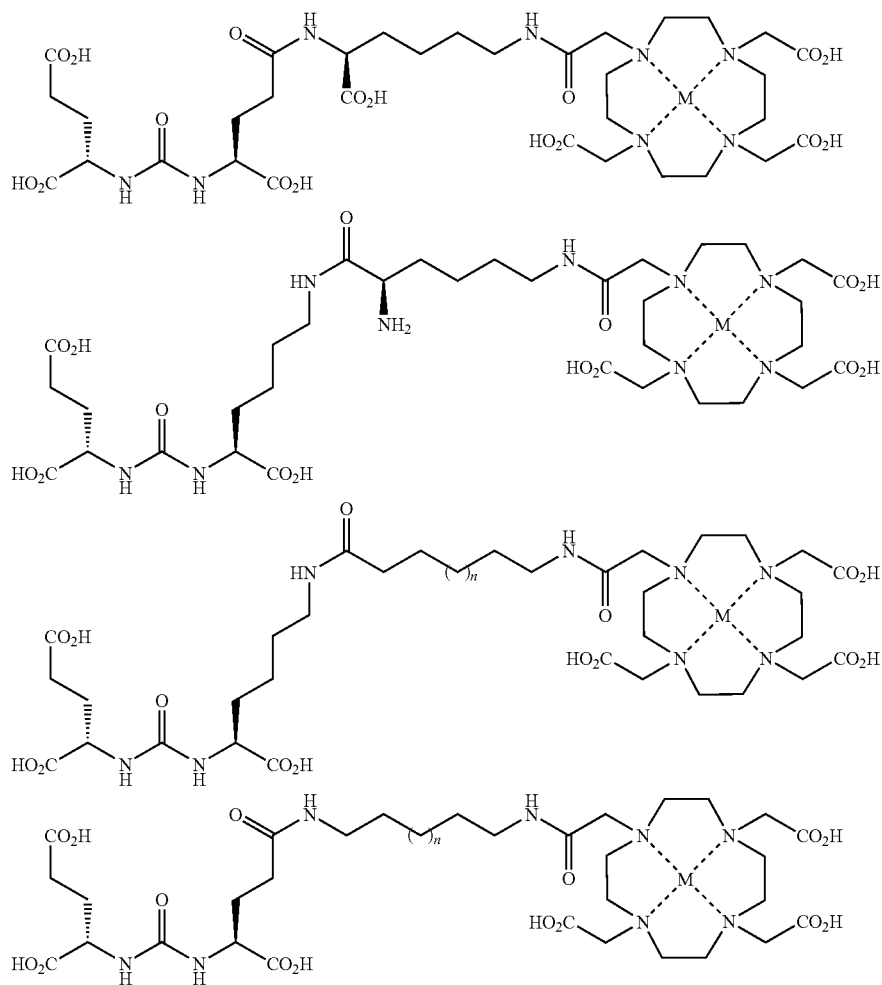
Example 18
Re(CO)$_3$ complex of (7S,22S,26S)-1-(1-methyl-1H-imidazol-2-yl)-2-((1-methyl-1H-imidazol-2-yl)methyl)-9,16,24-trioxo-2,8,17,23,25-pentaazaoctacosane-7,22,26,28-tetracarboxylic acid.
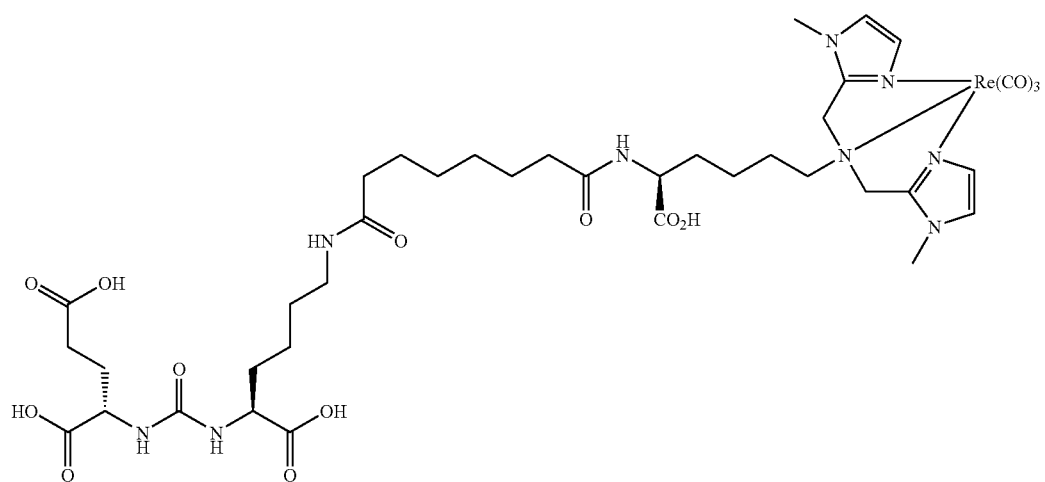

A solution of (S)-di-tert-butyl 2-(3-((S)-1-tert-butoxy-6-(8-(2,5-dioxopyrrolidin-1-yloxy)-8-oxooctanamido)-1-oxohexan-2-yl)ureido)pentanedioate (0.356 g, 0.48 mmol), the compound of Compound 13 (0.16 g, 0.48 mmol) and DIPEA (1.0 mL) in DMF (5.0 mL) was stirred at room temperature for overnight. The solvent was evaporated to give a residue, which was purified by Biotage eluting with DCM/MeOH to give (7S,11S,26S)-26-(4-(bis((1-methyl-1H-imidazol-2-yl)methyl)amino)butyl)-7,11-bis(tert-butoxycarbonyl)-2,2-dimethyl-4,9,17,24-tetraoxo-3-oxa-8,10,16,25-tetraazaheptacosan-27-oic acid (81 mg, 18%). MS (ESI), 481 (M/2+H)$^+$.

A solution of (7S,11S,26S)-26-(4-(bis((1-methyl-1H-imidazol-2-yl)methyl)amino)butyl)-7,11-bis(tert-butoxycarbonyl)-2,2-dimethyl-4,9,17,24-tetraoxo-3-oxa-8,10,16,25-tetraazaheptacosan-27-oic acid (72 mg, 0.075 mmol) and [NEt$_4$]$_2$[Re(CO)$_3$Br$_3$] (72 mg, 0.094 mmol) in MeOH (4 mL) at a pressure tube was stirred at 95° C. for 4 hrs. The solvent was evaporated to give a residue, which was directly used for next step. A solution of the above product in TFA/DCM was stirred at room temperature for overnight. The solvent was evaporated to give a crude product, which was purified by HPLC to give [Re(CO)$_3$][(7S,22S,26S)-1-(1-methyl-1H-imidazol-2-yl)-2-((1-methyl-1H-imidazol-2-yl)methyl)-9,16,24-trioxo-2,8,17,23,25-pentaazaoctacosane-7,22,26,28-tetracarboxylic acid] (4.0 mg) as a white solid. $^1$H NMR (400 MHz, DMSO-d$_6$) 8.08 (d, J=8.0 Hz, 1 H), 7.72 (t, J=5.4 Hz, 1 H), 7.24 (d, J=1.2 Hz, 2 H), 7.05 (d, J=1.2 Hz, 2 H), 6.31 (d, J=8.4 Hz, 1 H), 6.28 (d, J=8.0 Hz, 1 H), 4.69 (d, J=16.8 Hz, 2 H), 4.54 (d, J=16.8 Hz, 2 H), 4.28-4.23 (m, 1 H), 4.11-4.03 (m, 2 H), 3.78 (s, 6 H), 2.97-2.92 (m, 2 H), 2.26-2.20 (m, 2 H), 2.11 (t, J=7.2 Hz, 2 H), 1.99 (t, J=7.6 Hz, 2 H), 1.90-1.20 (m, 24 H); MS (ESI), 531.8 (M/2+H)$^+$.

Other complexes of the compounds of Formula I with rhenium, technetium, or other metal chelated complexes may be prepared by the above exemplified methods. Due to the lanthanide contraction, rhenium and technetium have a similar size and reactivity. As such, because rhenium has a number of stable isotopes that are not radioactive, the rhenium complexes make good synthetic and testing models for the behavior of the corresponding radioactive technetium complexes. Thus, where rhenium complexes are provided by way of example, the technetium complexes may also be prepared, and vice versa.

The examples following in Table 1 were, or are, prepared by the above methods, either isolated, or in situ as described above with respect to protected groups:

TABLE 1

Additional Example Compounds and Chelate Complexes Prepared By The Methods Exemplified In Compounds 1-11, By Appropriate Reagent Selection.

| Ex. Cmpd. | R | e | Z | f | W | g | NR$^a$R$^b$ |
|---|---|---|---|---|---|---|---|
| 19 | H | 4 | — | 0 | — | 0 | DIMA |
| 20 | H | 4 | -NH-C(O)-CH(CH$_3$)- | 6 | -C(O)-NH-CH(COOH)- | 4 | DQK |
| 21 | H | 4 | -NH-C(O)-CH(CH$_3$)- | 6 | -C(O)-NH-CH(COOH)- | 4 | M-DQK |
| 22 | H | 4 | -NH-C(O)-CH(CH$_3$)- | 6 | -C(O)-NH-CH(COOH)- | 4 | DPK |
| 23 | H | 4 | -NH-C(O)-CH(CH$_3$)- | 6 | -C(O)-NH-CH(COOH)- | 4 | M-DPK |
| 24 | Bu$^t$ | 4 | -NH-C(O)-CH(CH$_3$)- | 6 | -C(O)-NH-CH(COOH)- | 4 | PAMA |

TABLE 1-continued

Additional Example Compounds and Chelate Complexes Prepared By The
Methods Exemplified In Compounds 1-11, By Appropriate Reagent Selection.

| Ex. Cmpd. | R | e | Z | f | W | g | NR$^a$R$^b$ |
|---|---|---|---|---|---|---|---|
| 25 | H | 4 | -NH-C(O)- | 6 | -C(O)-NH-CH(COOH)- | 4 | PAMA |
| 26 | H | 4 | -NH-C(O)- | 6 | -C(O)-NH-CH(COOH)- | 4 | M-PAMA |
| 27 | Bu$^t$ | 4 | -NH-C(O)- | 6 | -C(O)-NH-CH(COOH)- | 4 | t-Bu-PAMA |
| 28 | H | 4 | -NH-C(O)- | 6 | -C(O)-NH-CH(COOH)- | 4 | PAMA |
| 29 | Bu$^t$ | 4 | -NH-C(O)- | 6 | -C(O)-NH-CH(COOH)- | 4 | t-Bu-DCMI |
| 30 | H | 4 | -NH-C(O)- | 6 | -C(O)-NH-CH(COOH)- | 4 | DCMI |
| 31 | H | 4 | -NH-C(O)- | 6 | -C(O)-NH-CH(COOH)- | 4 | M-DCMI |
| 32 | H | 4 | — | 0 | — | 0 | M-DCMI |
| 33 | H | 4 | -NH-C(O)- | 10 | — | 0 | DCMI |
| 34 | H | 4 | -NH-C(O)- | 10 | — | 0 | M-DCMI |

TABLE 1-continued

Additional Example Compounds and Chelate Complexes Prepared By The
Methods Exemplified In Compounds 1-11, By Appropriate Reagent Selection.

| Ex. Cmpd. | R | e | Z | f | W | g | NR$^a$R$^b$ |
|---|---|---|---|---|---|---|---|
| 35 | H | 4 | —NHC(O)— | 10 | — | 0 | M-DCMI |
| 36 | Bu$^t$ | 4 | —NHC(O)— | 6 | —C(O)NH—CH(COOH)— | 4 | DIMA |
| 37 | H | 4 | —NHC(O)— | 6 | —C(O)NH—CH(COOH)— | 4 | M-DIMA |
| 38 | H | 4 | —NHC(O)— | 10 | — | 0 | M-DIMA |
| 39 | H | 4 | —NHC(O)— | 6 | —C(O)NH— | 6 | PAMA |
| 40 | H | 4 | —NHC(O)— | 5 | — | 0 | M-DCMI |
| 41 | H | 4 | —NHC(O)— | 6 | —C(O)NH— | 6 | M-DPK |
| 42 | H | 4 | —NHC(O)— | 10 | 0 | 0 | M-CIMAA |
| 43 | H | 4 | —NHC(O)— | 10 | 0 | 0 | t-Bu-CIMAA |

TABLE 1-continued

Additional Example Compounds and Chelate Complexes Prepared By The Methods Exemplified In Compounds 1-11, By Appropriate Reagent Selection.

| Ex. Cmpd. | R | e | Z | f | W | g | NR$^a$R$^b$ |
|---|---|---|---|---|---|---|---|
| 44 | Bu$^t$ | 4 | —NHC(O)— | 10 | — | 0 | t-Bu-TIM |
| 45 | H | 4 | —NHC(O)— | 10 | — | 0 | M-TIM |
| 46 | H | 4 | —NHC(O)— | 0 | —CH$_2$CH$_2$OCH$_2$CH$_2$OCH$_2$CH$_2$— | 0 | M-DCMI |
| 47 | H | 4 | —NHC(O)— | 0 | —CH$_2$CH$_2$OCH$_2$CH$_2$OCH$_2$CH$_2$— | 2 | M-DCMI |
| 48 | H | 4 | —NHC(O)— | 0 | —CH(NH$_2$)— | 4 | M-DCMI |
| 49 | H | 4 | —NHC(O)— | 0 | —CH(NH$_2$)— | 4 | M-TIM |
| 50 | Bu$^t$ | 4 | —NHC(O)— | 0 | —CH(NH$_2$)— | 4 | t-Bu-CIMAA |
| 51 | Bu$^t$ | 4 | —NHC(O)— | 0 | —CH(NHFmoc)— | 4 | t-Bu-CIMAA |
| 52 | H | 4 | —NHC(O)— | 0 | —CH(NH$_2$)— | 3 | M-TIM |
| 53 | H | 4 | — | 0 | — | 0 | M-PAMA |

TABLE 1-continued

Additional Example Compounds and Chelate Complexes Prepared By The Methods Exemplified In Compounds 1-11, By Appropriate Reagent Selection.

| Ex. Cmpd. | R | e | Z | f | W | g | NR$^a$R$^b$ |
|---|---|---|---|---|---|---|---|
| 54 | H | 4 | —NH—C(O)— | 0 | —CH(NHFmoc)— | 4 | DOTA |
| 55 | Bu$^t$ | 4 | —NH—C(O)— | 0 | —CH(NHFmoc)— | 4 | DOTA |
| 56 | — | 4 | —NH—C(O)— | 0 | —CH(NHFmoc)— | 4 | M-DOTA |
| 57 | — | 4 | —NH—C(O)— | 0 | —CH(NH$_2$)— | 4 | M-DOTA |
| 58 | Bu$^t$ | 2 | —C(O)NH—CH(CO$_2$H)— | 0 | — | 4 | DCMI |
| 59 | H | 2 | —C(O)NH—CH(CO$_2$H)— | 0 | — | 4 | M-DCMI |
| 60 | Bu$^t$ | 2 | —C(O)NH—CH(CO$_2$H)— | 0 | — | 4 | t-Bu-TIM |
| 61 | H | 2 | —C(O)NH—CH(CO$_2$H)— | 0 | — | 4 | M-TIM |
| 62 | Bu$^t$ | 2 | —C(O)NH—CH(CO$_2$H)— | 4 | — |  | DOTA |

TABLE 1-continued

Additional Example Compounds and Chelate Complexes Prepared By The
Methods Exemplified In Compounds 1-11, By Appropriate Reagent Selection.

| Ex. Cmpd. | R | e | Z | f | W | g | $NR^aR^b$ |
|---|---|---|---|---|---|---|---|
| 63 | H | 2 | (structure with NH-C(O)-CH(CO$_2$H)-) | 4 | — | | M-DOTA |
| 64 | Bu$^t$ | 4 | (structure with NH-C(O)-CH(NH$_2$)-) | 4 | — | | DOTA |
| 65 | | 4 | (structure with NH-C(O)-CH(NH$_2$)-) | 4 | — | | M-DOTA |
| 66 | Bu$^t$ | 4 | NHC(O)(CH$_2$)$_n$ | n | — | | DOTA |
| 67 | H | 4 | NHC(O)(CH$_2$)$_n$ | n | — | | M-DOTA |
| 68 | Bu$^t$ | 2 | C(O)NH(CH$_2$)$_n$ | n | — | | DOTA |
| 69 | H | 2 | C(O)NH(CH$_2$)$_n$ | n | — | | M-DOTA |

Notes:
Abbreviations in the above table with respect to the $NR^aR^b$ group correspond to the following structures:

| Abbreviation | Structure |
|---|---|
| DOTA | (DOTA macrocycle structure) |

| Abbreviation | Structure |
|---|---|
| M-DOTA | 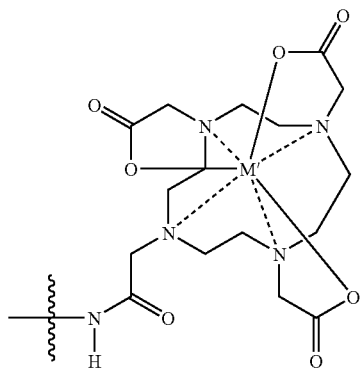 |
| DCMI | 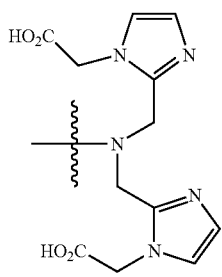 |
| t-Bu-DCMI | 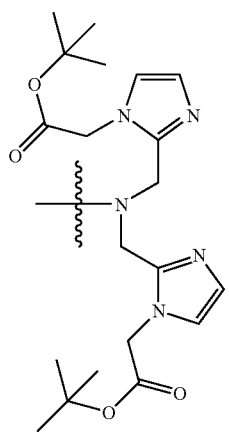 |
| M-DCMI | 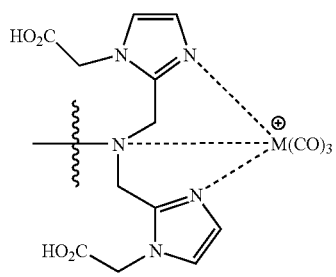 |

| Abbreviation | Structure |
|---|---|
| t-Bu-TIM | 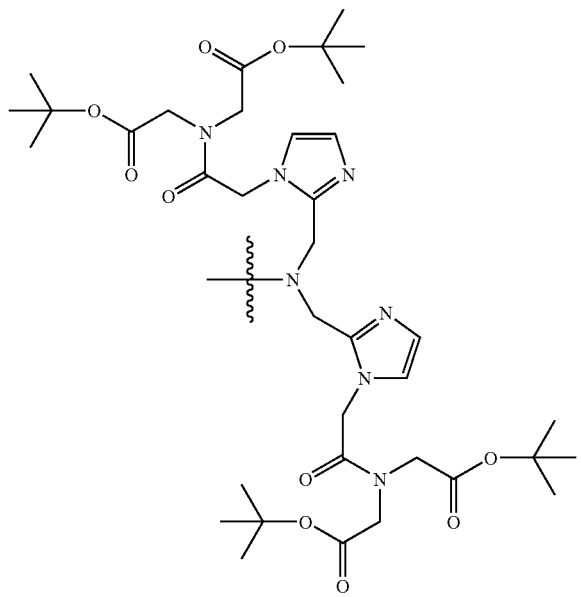 |
| M-TIM | 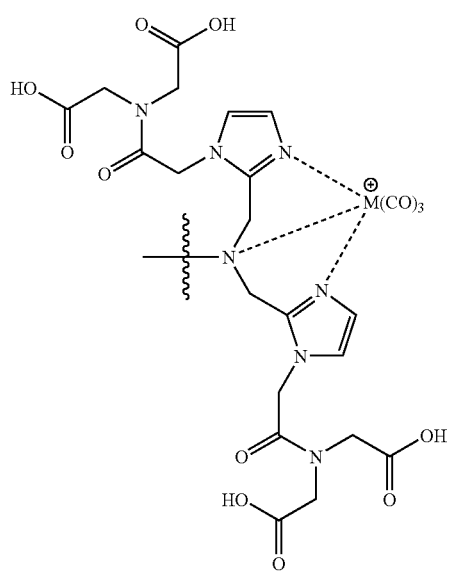 |
| PAMA | 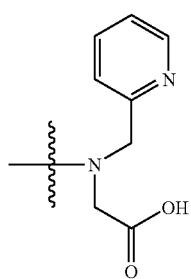 |

| Abbreviation | Structure |
|---|---|
| M-PAMA | 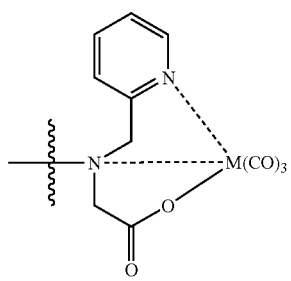 |
| DPK | 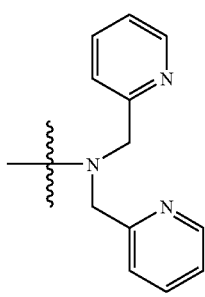 |
| M-DPK | 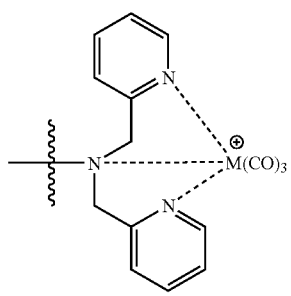 |
| DIMA | 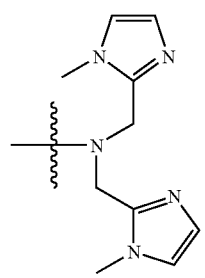 |
| M-DIMA | 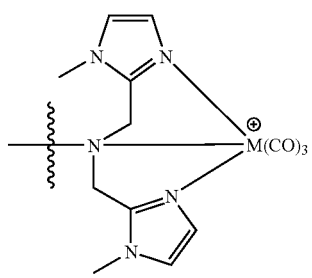 |

-continued
| Abbreviation | Structure |
|---|---|
| DQK | 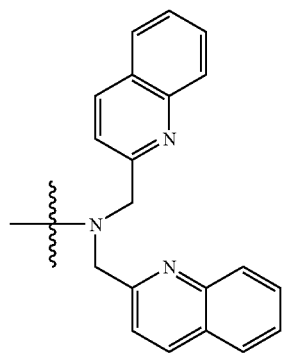 |
| M-DQK | 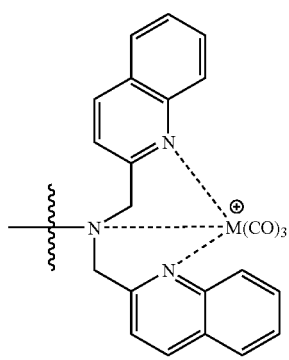 |
| t-Bu-CIMAA | 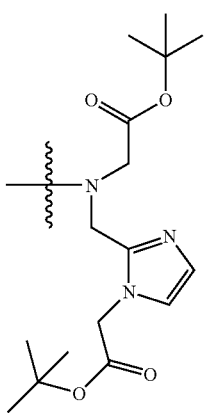 |
| M-CIMAA | 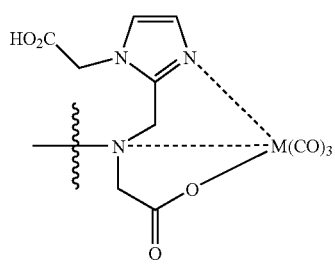 |

General Biology

The newly prepared analogs of the general structure 5 were screened in a human prostate cancer cell binding assay at a concentration of 3 nM using PSMA positive(+), LnCap cells. The results of this screening demonstrated to us whether the compounds exhibited specific binding to PSMA (+) cells. Compounds that exhibited specific binding to PSMA (+) cells where further evaluated in a competitive binding assay against the known inhibitor of PSMA, N—[N—[(S)-1,3-dicarboxypropyl]carbamoyl]-S-3-iodo-L-tyrosine (DCIT), and $IC_{50}$ values were calculated.

In Vitro Preliminary Screening

LNCaP and PC3 human prostate cancer cells were obtained from American Type Culture Collection, Rockville, Md. LNCaP cells were maintained in RPMI-1640 medium supplemented with 10% fetal bovine serum (FBS). Binding of the radiolabeled compound and competition with cold derivatives to LNCaP cells was performed according known procedures with appropriate modifications. Cells were plated in 12-well plates at approximately $4 \times 10^5$ cells/well and incubated for 48 hours in a humidified incubator at 37° C./5% carbon dioxide prior to addition of compound. Each Glu-urea-X derivative was prepared and diluted in serum-free cell culture medium containing 0.5% bovine serum albumin (BSA) in combination with 3 nM $^{123}$I DCIT (known inhibitor). Total binding was determined by incubating $^{123}$I-DCIT without test compound. Plates were incubated at room temperature for 1 hour. Cells were removed from the plates and transferred to Eppendorff tubes. Samples were micro centrifuged for 15 seconds at 10K×g. The medium was aspirated and the pellet was washed twice by dispersal in fresh assay medium followed by micro-centrifugation. Cell binding of $^{123}$I DCIT was determined by counting the cell pellet in an automated gamma counter. Nonspecific binding was determined as the counts associated with the cells after incubating with 2 uM nonradiolabeled compound or 2-phosphonomethyl-pentanedioic acid (PMPA). The key control compounds are depicted in the figure below.

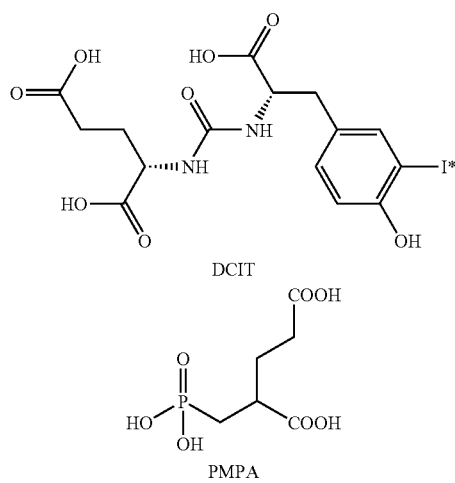

DCIT

PMPA

Biological Assay

The tissue biodistribution results, were consistent with the in-vitro data, and demonstrated significant uptake in the LNCaP (PSMA positive) tumors. The results also displayed a high degree of specificity with very little activity in the PC3 (PSMA negative) tumors.

The biological assessment using N—[N—[(S)-1,3-dicarboxypropyl]carbamoyl]-S-3-iodo-L-tyrosine (I-131-DCIT) verses "cold" complexes proved to be a rapid first screen, followed by dose curves to determine accurate $IC_{50}$ values. The lead series of compounds that exhibited IC50 values <50 nM. In vivo data of the lead series demonstrated high affinity, with 3% ID/g accumulating in the LNCaP tumors, and high specificity with the LNCaP-to-PC3 ratio exceeding 15 to 1.

The NAALADase Assays

The binding of NAAG is determined PSMA is determined as follows: (a) Preparation of the Reaction Mixture: the Reaction Mixture is Prepared by Combining LNCaP cell lysate (200 μg) with 600 uL Reaction buffer (Reaction Buffer: 50 mM Tris-HCl, pH 7.4, 20 mM $CoCl_2$, 32 mM NaCl). The mixture is allowed to pre-incubate at 37° C. for 3 min prior to use. (b) Preparation of radio-labeled NAAG solution: The radio-labeled NAAG stock is prepares by diluting 1 μl of a 100 mM stock to 100 μl using the Reaction Buffer (1 mM). (c) Assay: The assay is conducted by adding 6 μL of 1 mM NAAG (for 1 μM final conc) spiked with 1,000,000 CPM of $^3$H-NAAG (100 μL of 1 mM NAAG+10 μL of 3H-NAAG (10 μCi)), to the reaction mixture. For competitive binding studies add PMPA [ . . . what concentration . . . ] and incubate the resultant solution for 30 min 37° C. The reaction is stopped at specific time points by removing 100 uL of the reaction-mix and adding an equal volume of ice cold 0.25 M $KH_2PO_4$, pH 4.3. Approximately one-half of the buffered mixture is loaded onto a 250 mg AG 50W-X4 cation exchange column (200-400 mesh, $H^+$ form, swell resin with DI H2O prior to use). The loaded column is washed with 500 μL 1:1 Rxn Buffer/ $0.25MKH_2PO_4$ and eluted with 3M KCl (1.5 mL). The concentration of radiolabel bound to the column is determined using a scintillation counter and 100 μL of the eluent (diluted 1:6) to minimize quenching.

Therapeutic Treatments

Compounds of the present can be used to inhibit NAALADase for therapeutic treatments. Diseases that could be receptive to NAALADase treatment include painful and sensory diabetic neuropathy, neuronal damage and prostate cancer, schizophrenia, colorectal cancer, inflammation, amyotrophic lateral sclerosis, or diabetic neuropathy. The present compounds can also be used an analgesic. Guidance for the modeling of such therapeutic treatments can be found in Goodman & Gilman's The Pharmacological Basis of Therapeutics, McGraw Hill, 10 edition, 2001, Pharmaceutical Preformulation and Formulation: A Practical Guide from Candidate Drug Selection to Commercial Dosage Form, CRC, 2001 and Handbook of Pharmaceutical Excipients, AphA Publications, 5 edition, 2005.

In the figures, several compounds are referenced for the purposes of comparison. Those comparison compounds and their structures are provided below:

| Comp. Ex. No. | Structure |
|---|---|
| 1 | 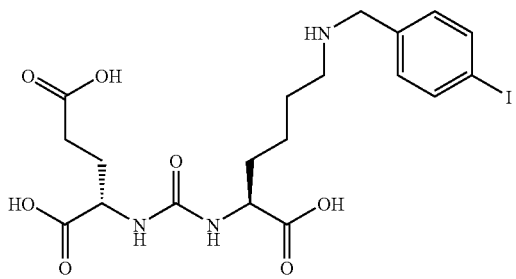 |
| 2 | 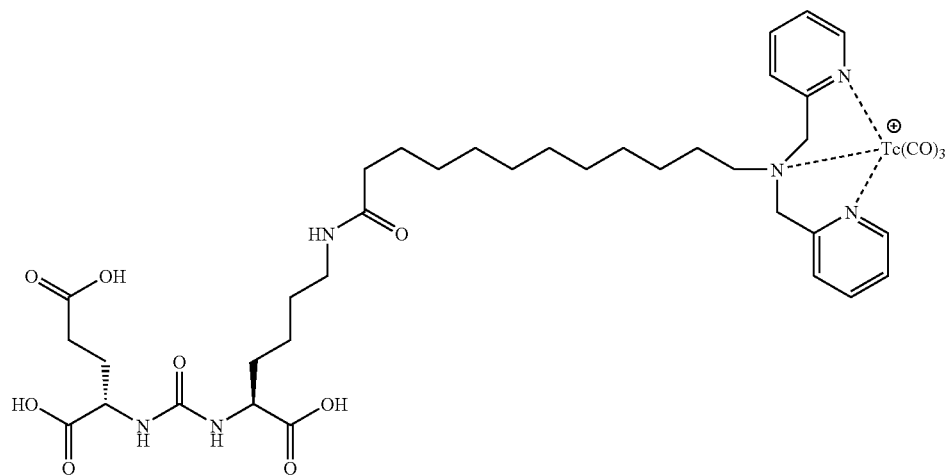 |
| 3 | 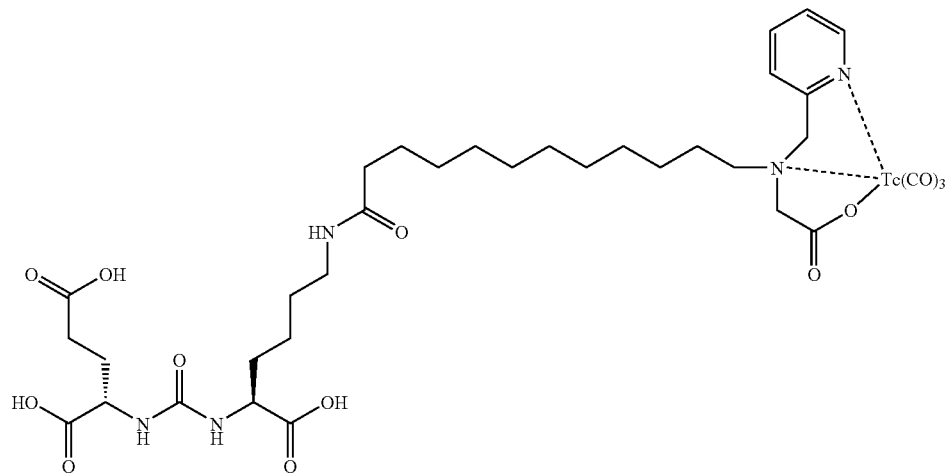 |

-continued

| Comp. Ex. No. | Structure |
|---|---|
| 4 | 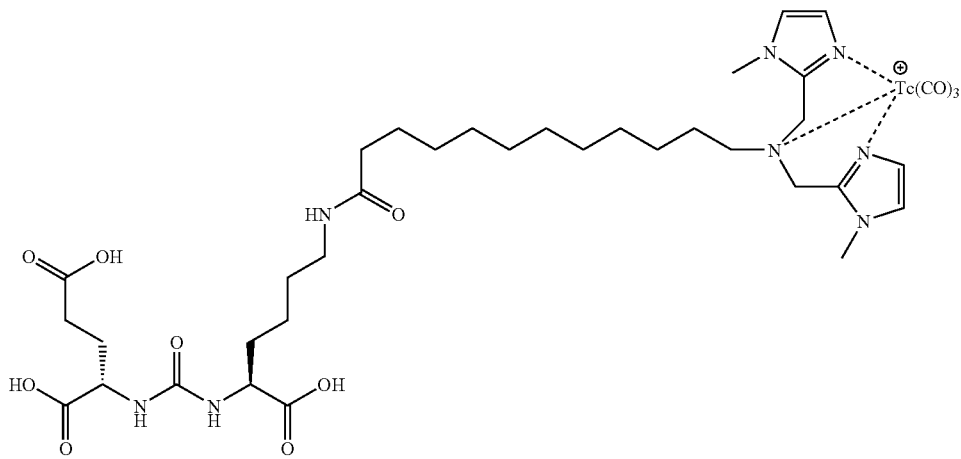 |
| 5 | 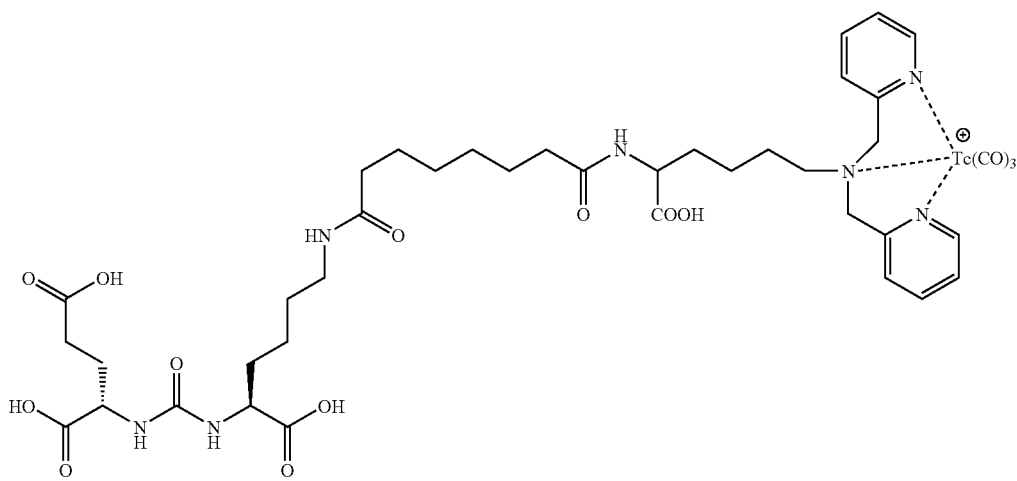 |
| 6 | 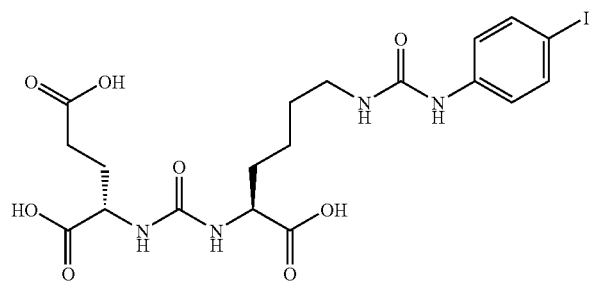 |

Tissue Distribution of Exemplary Radiopharmaceuticals

Figure 6:
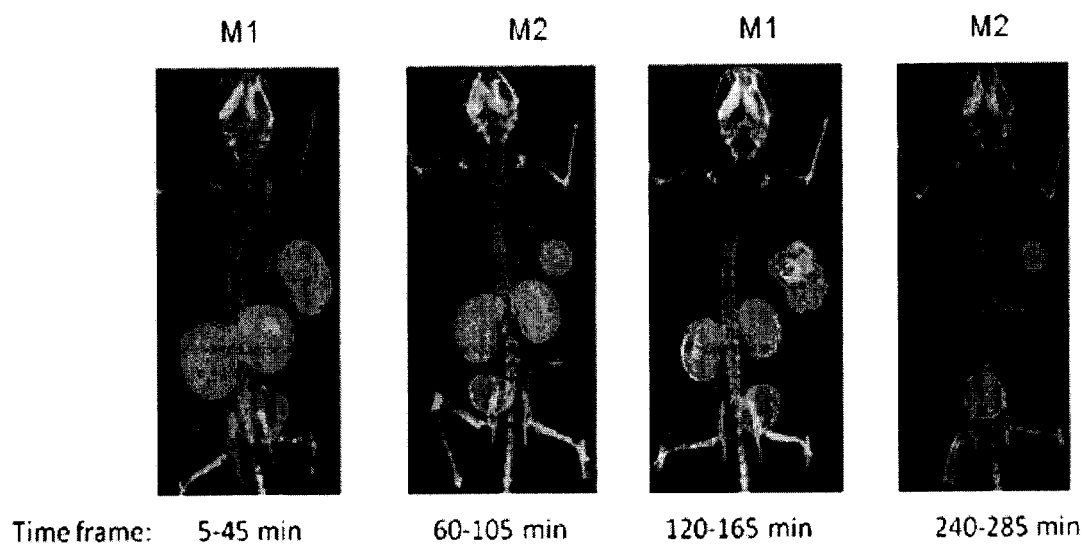
FIG. 6 is an image illustrating the tissue biodistribution for a $^{99m}$Tc complex of the compound of Example 6 in LNCaP Xenograft mice at various time intervals, and according to some embodiments.

A number of the compounds and complexes prepared herein were evaluated for tissue distribution, and in some cases in comparison to comparative compounds. FIGS. 1, 3, 4, and 5 present some of this data graphically. FIG. 6 is a radioimage illustrating the tissue biodistribution for a $^{99m}$Tc complex of the compound of Example 6.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, including the first and last number listed for the range.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A compound of Formula I, a pharmaceutically acceptable salt thereof:

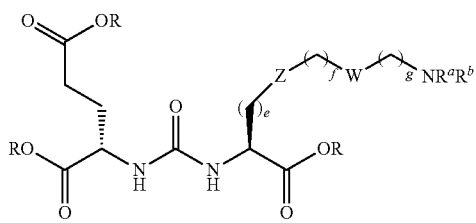

wherein
R is H, an ammonium ion, an alkylammonium ion, an alkaline earth metal ion, a rare earth metal ion, or an alkyl group;
W is a bond, —NHC(O)—, —CH($NH_2$)—, —NH—C(O)—NH—, —C(O)—NH—, —C(O)—NH—CH(COOH)—, —O—($CH_2$)$_n$—O—($CH_2$)$_n$-, —($CH_2$)$_n$O($CH_2$)$_n$O($CH_2$)$_n$-, —CH(NHFmoc)-;
Z is a bond, —CO(O)—, —NH—, —NHC(O)—, —NH—C(O)—NH—, —NH—C(O)—($CH_2$)$_n$-, —NH—C(O)—CH($NH_2$)—, —C(O)—NH—CH(COOH)—; or —NH—C(O)—$C_6H_4$-($CH_2$)$_n$—NH—;

$NR^aR^b$ is a chelator group of Formula:

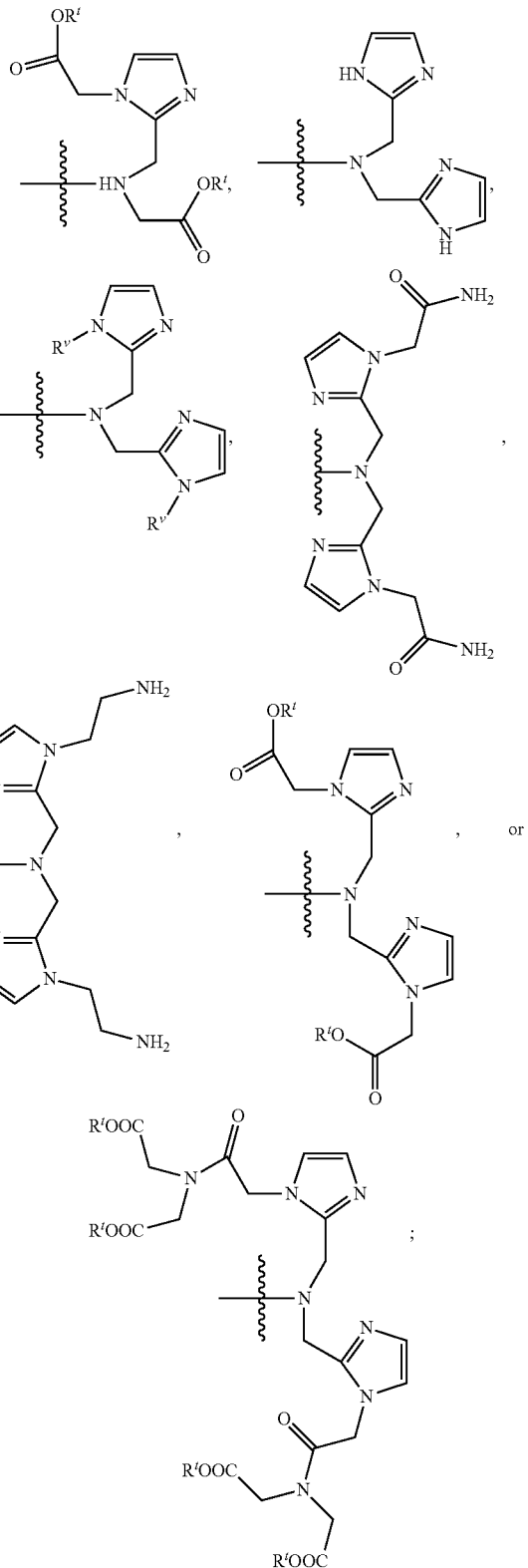

$R^t$ is H, a $C_1$-$C_8$ alkyl group, an ammonium ion, an alkylammonium ion, or an alkali or alkaline earth metal ion;
$R^v$ is alkyl;
e is an integer from 0 to 15;
f is an integer from 0 to 15;

g is an integer from 0 to 15; and n is an integer from 0 to 10.

2. The compound of claim 1, wherein R$^v$ is methyl, ethyl, n-propyl, iso-propyl, n-butyl, iso-butyl, or tert-butyl.

3. The compound of claim 2, wherein R$^v$ is methyl.

4. The compound of claim 1, wherein each R$^t$ is independently H or tert-butyl.

5. The compound of claim 4, wherein R$^t$ is H.

6. The compound of claim 1, wherein is e is an integer from 0 to 4, f is an integer from 0 to 12, and g is an integer from 0 to 6.

7. The compound of claim 1, wherein W is —C(O)—NH—.

8. The compound of claim 1 that is:

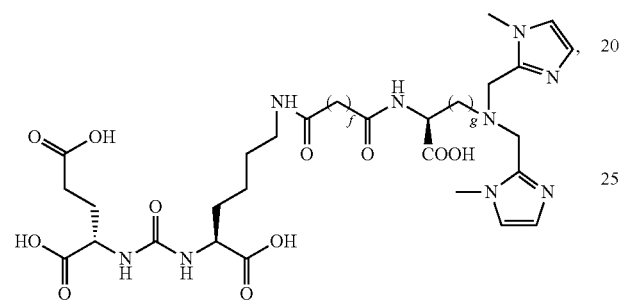

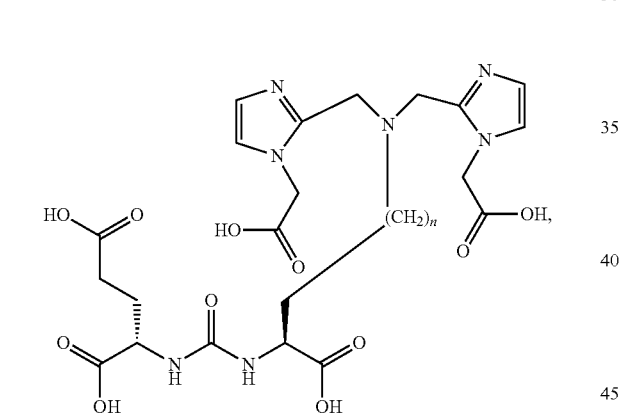

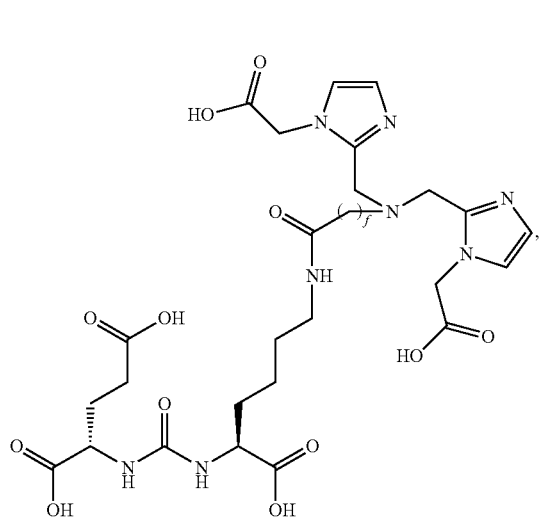

-continued

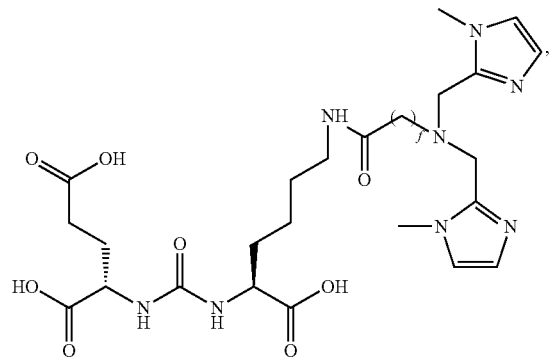

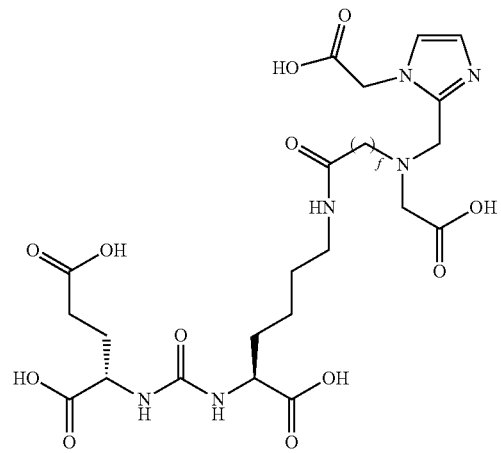

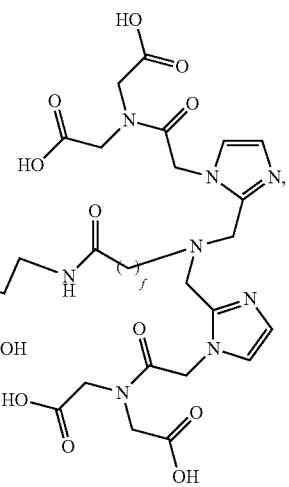

121
-continued

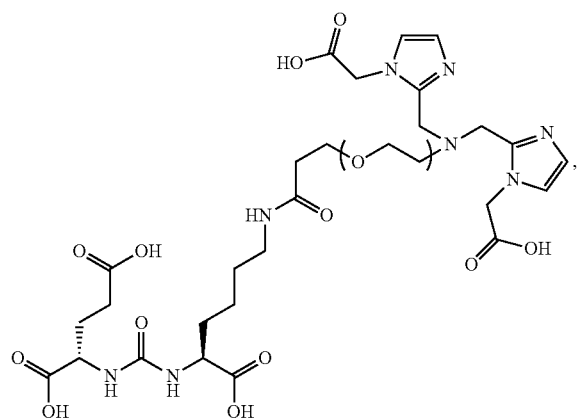

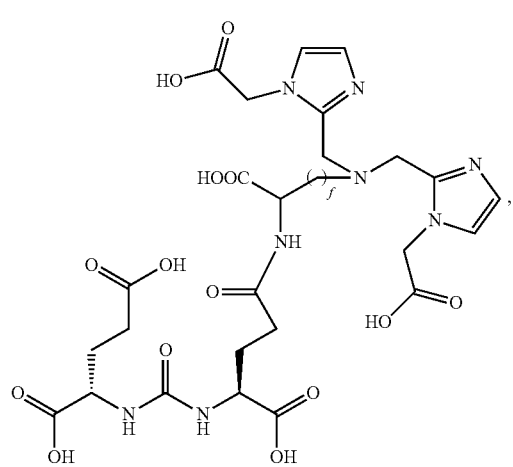

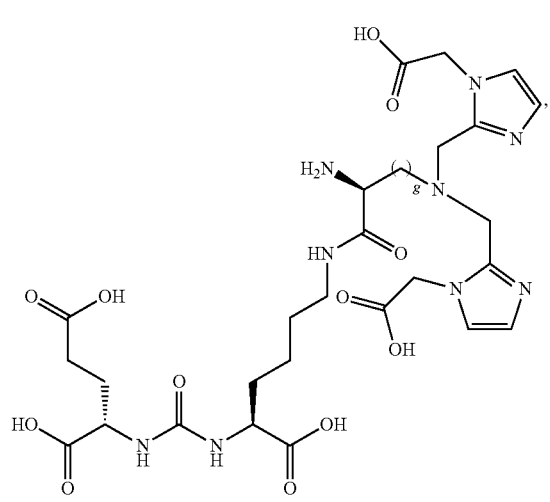

122
-continued

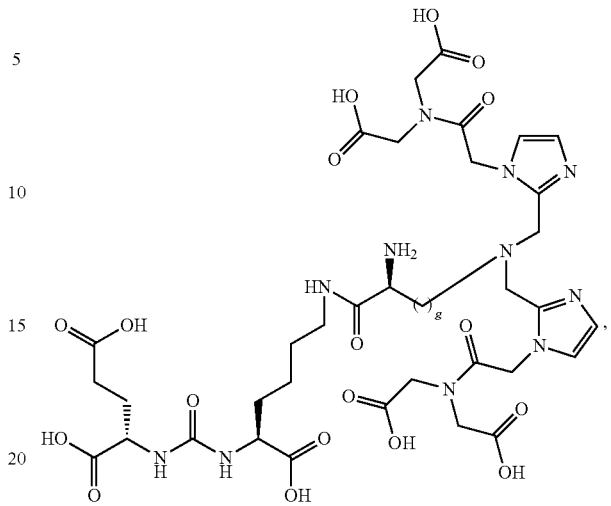

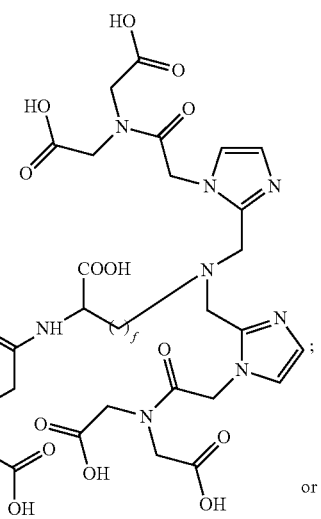

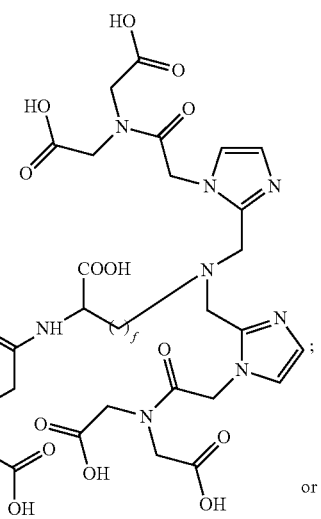

or a pharmaceutically acceptable salt thereof;

e is an integer from 0 to 10;

f is an integer from 0 to 12;

g is an integer from 0 to 12; and n is an integer from 0 to 10.

9. The compound of claim 1, wherein Z is —NH—C(O)—.

10. The compound of claim 1, wherein Z is —C(O)—NH—CH(COOH)—.

11. The compound of claim 1, wherein Z is —NH—C(O)—CH(NH$_2$)—.

12. A complex comprising, a metal and the compound of claim 1.

13. The complex of claim 12, wherein the metal is Re, Tc, Y, Lu, Ga, In or Cu.

14. The complex of claim 12, wherein the metal is a radionuclide.

15. The complex of claim 14, wherein the metal is technetium-99 m, rhenium-186, or rhenium-188.

16. The complex of claim 12 that is:
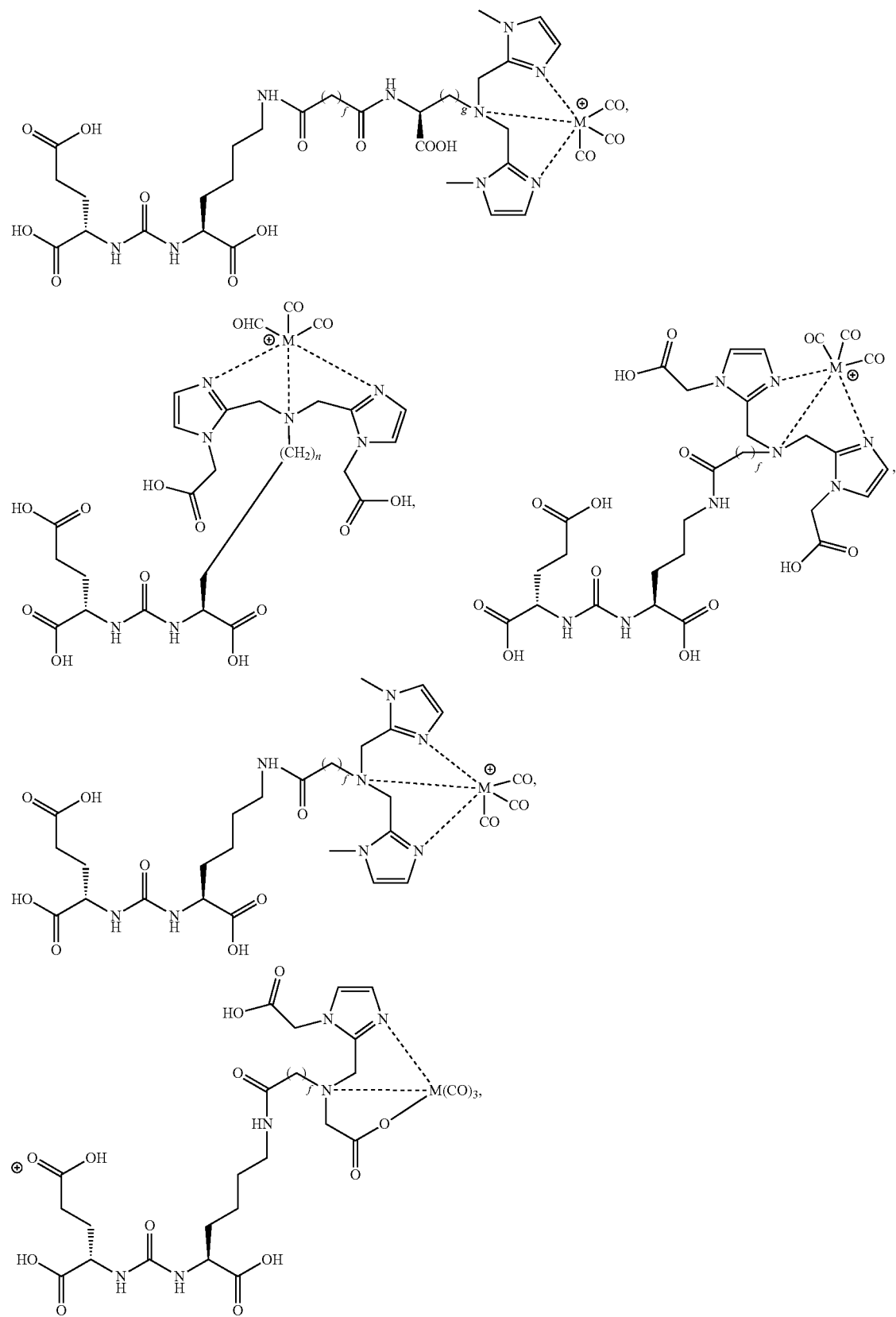

-continued
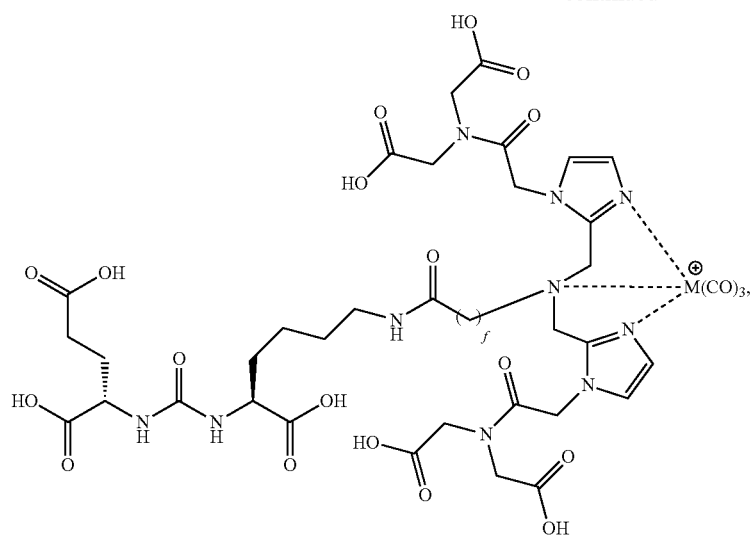
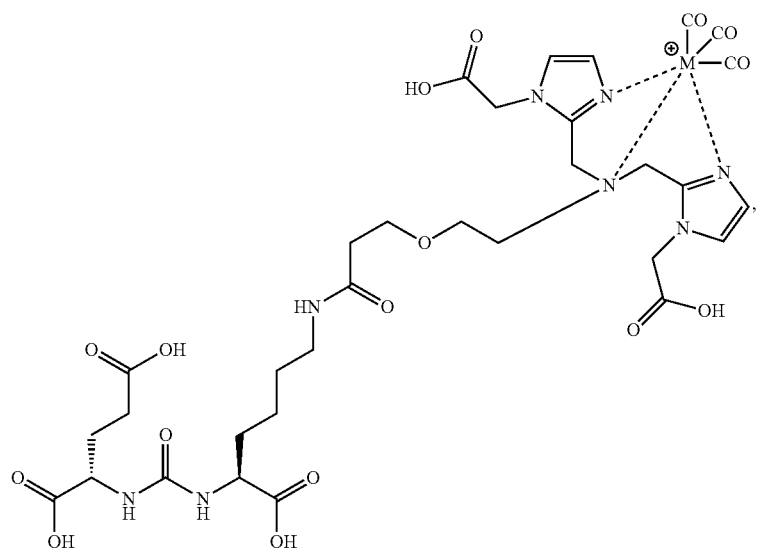
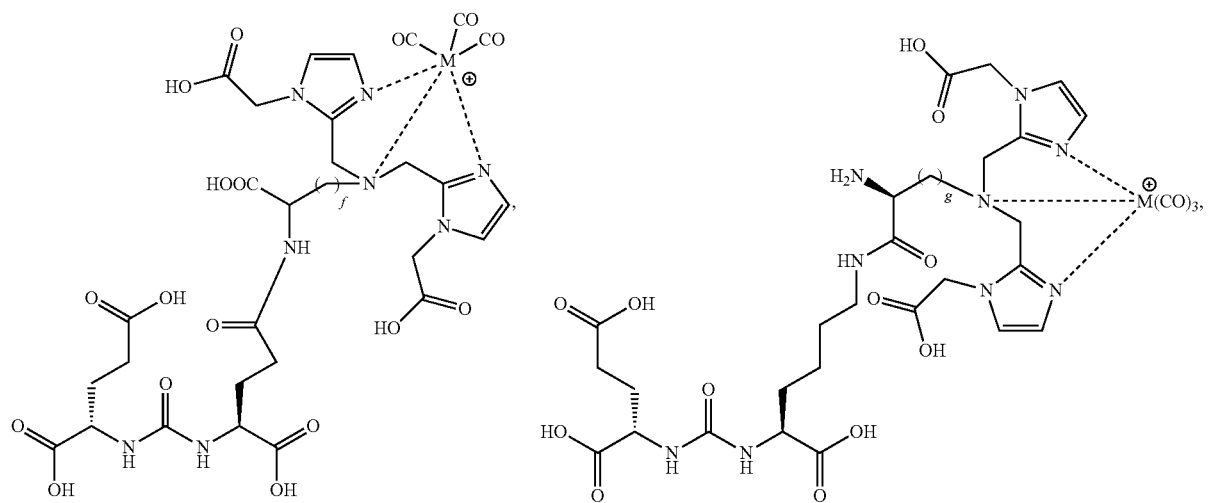

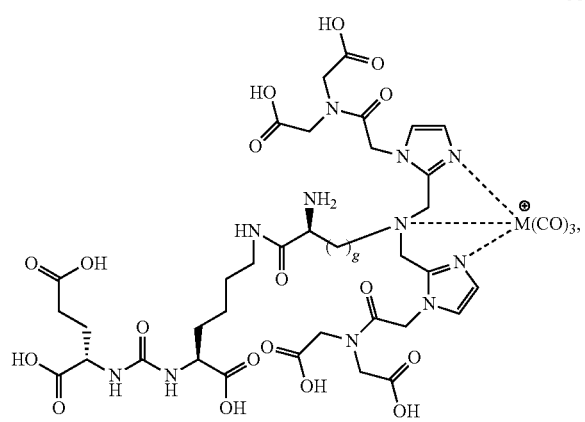

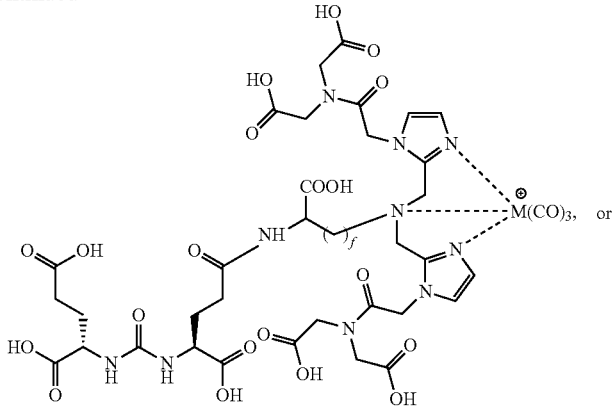

a pharmaceutically acceptable salt thereof;
M is Re, Tc, Y, Lu, Ga, In or Cu;
e is an integer from 0 to 10;
f is an integer from 0 to 12;
g is an integer from 0 to 12; and
n is an integer from 0 to 10.

17. A pharmaceutical formulation, comprising the compound according to any one of the preceding claims, or a pharmaceutically acceptable salt thereof, and a pharmaceutically acceptable excipient.

18. A method of imaging a region in a patient, comprising the steps of: administering to a patient a diagnostically effective amount of a compound of any one of the preceding claims, or a pharmaceutically acceptable salt thereof, and obtaining an image of the region of the patient.

19. A method of imaging tissue selected from spleen tissue, kidney tissue, and PSMA-expressing tumor tissue, including contacting the tissue with a complex comprising a radioactive metal and a compound comprising a group of formula:

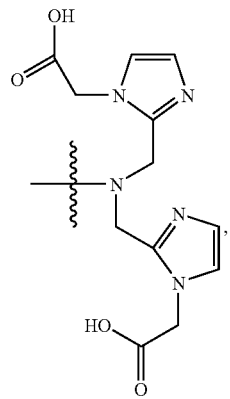

a pharmaceutically acceptable salt thereof.

20. The method of claim 19, wherein the tissue is PSMA-expressing tumor tissue.

* * * * *

UNITED STATES PATENT AND TRADEMARK OFFICE
CERTIFICATE OF CORRECTION

| | |
|---|---|
| PATENT NO. | : 8,211,401 B2 |
| APPLICATION NO. | : 12/631337 |
| DATED | : July 3, 2012 |
| INVENTOR(S) | : John W. Babich et al. |

Page 1 of 1

It is certified that error appears in the above-identified patent and that said Letters Patent is hereby corrected as shown below:

IN THE SPECIFICATION

Column 25, line 35, please delete "compound of Example 8" and replace with -- compound of Example 7 --.

Column 25, line 38, please delete "compound of Example 7" and replace with -- compound of Example 6 --.

Signed and Sealed this
Nineteenth Day of August, 2014

Michelle K. Lee
*Deputy Director of the United States Patent and Trademark Office*